US012780934B2

(12) United States Patent
Padler-Karavani et al.

(10) Patent No.: US 12,780,934 B2

(45) Date of Patent: Nov. 3, 2026

(54) ANTIBODIES TO CANCER GLYCOSYLATION AND USES THEREOF

(71) Applicants: YEDA RESEARCH AND DEVELOPMENT CO. LTD., Rehovot (IL); RAMOT AT TEL-AVIV UNIVERSITY LTD., Tel Aviv (IL)

(72) Inventors: Vered Padler-Karavani, Tel Aviv (IL); Ron Diskin, Rehovot (IL); Sarel Fleishman, Rehovot (IL); Aliza Borenstein Katz, Rehovot (IL); Shira Warszawski, Rehovot (IL); Ron Amon, Tel Aviv (IL)

(73) Assignees: YEDA RESEARCH AND DEVELOPMENT CO. LTD., Rehovot (IL); RAMOT AT TEL-AVIV UNIVERSITY LTD., Tel Aviv (IL)

( * ) Notice: Subject to any disclaimer, the term of this patent is extended or adjusted under 35 U.S.C. 154(b) by 584 days.

(21) Appl. No.: 18/261,149

(22) PCT Filed: Jan. 11, 2022

(86) PCT No.: PCT/IL2022/050044

§ 371 (c)(1),
(2) Date: Jul. 12, 2023

(87) PCT Pub. No.: WO2022/153298

PCT Pub. Date: Jul. 21, 2022

(65) Prior Publication Data

US 2025/0297027 A1 Sep. 25, 2025

Related U.S. Application Data

(60) Provisional application No. 63/136,298, filed on Jan. 12, 2021.

(51) Int. Cl.

*A61P 35/00* (2006.01)
*C07K 16/28* (2006.01)
*A61K 39/00* (2006.01)

(52) U.S. Cl.

CPC .......... *C07K 16/2896* (2013.01); *A61P 35/00* (2018.01); *A61K 2039/505* (2013.01); *C07K 2317/33* (2013.01); *C07K 2317/622* (2013.01); *C07K 2317/92* (2013.01)

(58) Field of Classification Search

CPC ............ C07K 16/2896; C07K 2317/33; C07K 2317/622; C07K 2317/92; A61P 35/00; A61K 2039/505

USPC ........................................................ 424/133.1

See application file for complete search history.

(56) References Cited

U.S. PATENT DOCUMENTS

| | | | |
|---|---|---|---|
| 4,036,945 A | 7/1977 | Haber | |
| 4,331,647 A | 5/1982 | Goldenberg | |
| 4,471,057 A | 9/1984 | Koprowski | |
| 4,816,567 A | 3/1989 | Cabilly | |
| 4,946,778 A | 8/1990 | Ladner | |
| 5,189,178 A | 2/1993 | Galardy | |
| 5,239,078 A | 8/1993 | Galardy | |
| 5,545,806 A | 8/1996 | Lonberg | |
| 5,545,807 A | 8/1996 | Surani | |
| 5,569,825 A | 10/1996 | Lonberg | |
| 5,625,126 A | 4/1997 | Lonberg | |
| 5,633,425 A | 5/1997 | Lonberg | |
| 5,661,016 A | 8/1997 | Lonberg | |
| 9,045,528 B2 | 6/2015 | Florian | |
| 9,133,274 B2 | 9/2015 | Himmler | |
| 2023/0174664 A1 * | 6/2023 | Padler-Karavani .......................... | C07K 16/2896 424/135.1 |

FOREIGN PATENT DOCUMENTS

| | | | |
|---|---|---|---|
| WO | 9402610 | A1 | 2/1994 |
| WO | 9503832 | A1 | 2/1995 |
| WO | 2015053871 | A2 | 4/2015 |
| WO | 2016005969 | A1 | 1/2016 |
| WO | 2016057890 | A1 | 4/2016 |
| WO | 2017017673 | A2 | 2/2017 |
| WO | 2021105988 | A1 | 6/2021 |
| WO | 2021105989 | A1 | 6/2021 |

OTHER PUBLICATIONS

Martin et al., (1989) Modeling antibody hypervariable loops: a combined algorithm. Proc Natl Acad Sci U S A 86(23):9268-9272.
McCoy et al., (2007) Phaser crystallographic software. J Appl Crystallogr 40(Pt 4):658-674.
Mhashilkar et al., (1995) Inhibition of HIV-1 Tat-mediated LTR transactivation and HIV-1 infection by anti-Tat single chain intrabodies. EMBO J 14(7): 1542-1551.
Morrison (1994) Immunology. Success in specification. Nature 368(6474): 812-813.
Munkley and Elliott (2016) Hallmarks of glycosylation in cancer. Oncotarget 7(23): 35478-35489.
Muthana and Gildersleeve (2014) Glycan microarrays: powerful tools for biomarker discovery. Cancer Biomark 14(1):29-41.
Neuberger (1996) Generating high-avidity human Mabs in mice. Nat Biotechnol 14(7): 826.
Orlandi et al., (1989) Cloning immunoglobulin variable domains for expression by the polymerase chain reaction. Proc Natl Acad Sci U S A 86(10): 3833-3837.

(Continued)

*Primary Examiner* — Yan Xiao

(74) *Attorney, Agent, or Firm* — Ballard Spahr LLP

(57) ABSTRACT

The present invention provides isolated monoclonal antibodies that specifically bind to Sialyl Lewis A (SLeA) glycan, fragments thereof and humanized version of said antibodies or fragments, as well as conjugates thereof. The invention further provides chimeric antigen receptors comprising said antibodies or fragments and cells, such as T cells comprising same. The invention further provides pharmaceutical compositions comprising all of the above agents and use of said agents and compositions for diagnosing and treating cancer characterized by overexpression of SLeA.

20 Claims, 15 Drawing Sheets

Specification includes a Sequence Listing.

(56) References Cited

OTHER PUBLICATIONS

Pack et al., (1993) Improved bivalent miniantibodies, with identical avidity as whole antibodies, produced by high cell density fermentation of Escherichia coli. Biotechnology (N Y) 11(11): 1271-1277.
Padler-Karavani et al., (2012) Cross-comparison of protein recognition of sialic acid diversity on two novel sialoglycan microarrays. J Biol Chem 287(27): 22593-22608.
Padler-Karavani (2014) Aiming at the sweet side of cancer: aberrant glycosylation as possible target for personalized- medicine. Cancer Lett 352(1): 102-112.
Passerini et al., (2007) Interchangeability of measurements of CA 19-9 in serum with four frequently used assays: an update. Clin Chem Lab Med 45(1): 100-104.
Paul and Padler-Karavani (2018) Evolution of sialic acids: Implications in xenotransplant biology. Xenotransplantation 25(6): e12424.
Porter (1959) The hydrolysis of rabbit y-globulin and antibodies with crystalline papain. Biochem J 73(1): 119-126.
Presta (1992) Antibody engineering. Current Opinion in Structural Biology 2(4): 593-596.
Re et al., (2012) Conformational flexibility of N-glycans in solution studied by REMD simulations. Biophys Rev 4(3): 179-187.
Richardson and Marasco (1995) Intracellular antibodies: development and therapeutic potential. Trends Biotechnol 13(8): 306-310.
Richardson et al., (1995) Phenotypic knockout of the high-affinity human interleukin 2 receptor by intracellular single-chain antibodies against the alpha subunit of the receptor. Proc Natl Acad Sci U S A 92(8): 3137-3141.
Riechmann et al., (1988) Reshaping human antibodies for therapy. Nature 332(6162): 323-327.
Sadelain et al., (2013) The basic principles of chimeric antigen receptor design. Cancer Discov 3(4): 388-398.
Safdari et al., (2013) Antibody humanization methods—a review and update. Biotechnol Genet Eng Rev 29: 175-186.
Sawada et al., (2011) Human monoclonal antibodies to sialyl-Lewis (CA19.9) with potent CDC, ADCC, and antitumor activity. Clin Cancer Res 17(5): 1024-1032.
Shaheen et al., (1996) Targeting human immunodeficiency virus type 1 reverse transcriptase by intracellular expression of single-chain variable fragments to inhibit early stages of the viral life cycle. J Virol 70(6): 3392-3400.
Siegel et al., (2019) Cancer statistics, 2019. CA Cancer J Clin 69(1): 7-34.
Ugorski and Laskowska (2002) Sialyl Lewis(a): a tumor-associated carbohydrate antigen involved in adhesion and metastatic potential of cancer cells. Acta Blochim Pol 49(2): 303-311.
Verhoeyen et al., (1988) Reshaping human antibodies: grafting an antilysozyme activity. Science 239(4847): 1534-1536.
Waldmann (2019) Human Monoclonal Antibodies: The Benefits of Humanization. In: Steinitz, M. (eds) Human Monoclonal Antibodies. Methods in Molecular Biology, vol. 1904. Humana Press, New York, NY. pp. 1-10.
Ward et al., (1989) Binding activities of a repertoire of single immunoglobulin variable domains secreted from *Escherichia coli*. Nature 341(6242): 544-546.
Warszawski et al., (2019) Optimizing antibody affinity and stability by the automated design of the variable light-heavy chain interfaces. PLoS Comput Biol 15(8): e1007207.
Wrammert et al., (2008) Rapid cloning of high-affinity human monoclonal antibodies against influenza virus. Nature 453(7195): 667-671.
Weitzenfeld et al., (2019) Antibodies targeting sialyl Lewis A mediate tumor clearance through distinct effector pathways. J Clin Invest 129(9): 3952-3962.
Werge et al., (1990) Intracellular immunization. Cloning and intracellular expression of a monoclonal antibody to the p21ras protein. FEBS Lett 274(1-2): 193-198.
Whitlow and Filpula (1991) Single-chain Fv proteins and their fusion proteins. Methods 2(2): 97-105.
Winter and Milstein (1991) Man-made antibodies. Nature 349(6307): 293-299.
Adams et al., (2010) PHENIX: a comprehensive Python-based system for macromolecular structure solution. Acta Crystallogr D Biol Crystallogr 66(Pt 2): 213-221.
Ahmadzadeh et al., (2014) Antibody humanization methods for development of therapeutic applications. Monoclon Antib Immunodiagn Immunother 33(2): 67-73.
Amon et al., (2018) A combined computational-experimental approach to define the structural origin of antibody recognition of sialyl-Tn, a tumor-associated carbohydrate antigen. Sci Rep 8(1): 10786.
Amon et al., (2020) Directed Evolution of Therapeutic Antibodies Targeting Glycosylation in Cancer. Cancers (Basel) 12(10): 2824.
Ballehaninna and Chamberlain (2011) Serum CA 19-9 as a Biomarker for Pancreatic Cancer-A Comprehensive Review. Indian J Surg Oncol 2(2): 88-100.
Ballehaninna and Chamberlain (2012) The clinical utility of serum CA 19-9 in the diagnosis, prognosis and management of pancreatic adenocarcinoma: An evidence based appraisal. J Gastrointest Oncol 3(2): 105-119.
Beerli et al., (1994) Intracellular expression of single chain antibodies reverts ErbB-2 transformation. J Biol Chem 269 (39): 23931-23936.
Blocca et al., (1994) Intracellular immunization with cytosolic recombinant antibodies. Biotechnology (N Y) 12(4): 396-399.
Bird et al., (1988) Single-chain antigen-binding proteins. Science 242(4877): 423-426.
Blanas et al., (2018) Fucosylated Antigens in Cancer: An Alliance toward Tumor Progression, Metastasis, and Resistance to Chemotherapy. Front Oncol 8: 39.
Boerner et al., (1991) Production of antigen-specific human monoclonal antibodies from in vitro-primed human splenocytes. J Immunol 147(1): 86-95.
Borenstein-Katz et al., (2021) Biomolecular Recognition of the Glycan Neoantigen CA19-9 by Distinct Antibodies. J Mol Biol 433(15): 167099. With Supplementary information.
Boyiadzis et al., (2018) Chimeric antigen receptor (CAR) T therapies for the treatment of hematologic malignancies: clinical perspective and significance. J Immunother Cancer 6(1): 137.
Brudno et al., (2020) Safety and feasibility of anti-CD19 Car T cells with fully human binding domains in patients with B-cell lymphoma. Nat Med. Author manuscript; available in PMC Jan. 4, 2021. Published in final edited form as: Nat Med. Feb. 2020; 26(2): 270-280.
Carison (1993) A new use for intracellular antibody expression: inactivation of human immunodeficiency virus type 1. Proc Natl Acad Sci U S A 90(16): 7427-7428.
Chen et al., (1994) Combined intra- and extracellular immunization against human immunodeficiency virus type 1 infection with a human anti-gp120 antibody. Proc Natl Acad Sci U S A 91(13): 5932-5936.
Chen et al., (1994) Intracellular antibodies as a new class of therapeutic molecules for gene therapy. Hum Gene Ther 5(5): 595-601.
Chothia et al., (1989) Conformations of immunoglobulin hypervariable regions. Nature 342(6252): 877-883.
Cohen and Varki (2010) The sialome—far more than the sum of its parts. OMICS 14(4): 455-464.
Cole et al., (1984) Human monoclonal antibodies. Mol Cell Biochem 62(2): 109-120.
Cote et al., (1983) Generation of human monoclonal antibodies reactive with cellular antigens. Proc Natl Acad Sci U S A 80(7): 2026-2030.
Deshane et al., (1994) Intracellular single-chain antibody directed against erbB2 down-regulates cell surface erbB2 and exhibits a selective anti-proliferative effect in erbB2 overexpressing cancer cell lines. Gene Ther 1(5): 332-337. Abstract.
Dong et al., (2018) Periostin and CA242 as potential diagnostic serum biomarkers complementing CA19.9 in detecting pancreatic cancer. Cancer Sci 109(9): 2841-2851.
Duan et al., (1994) Potent inhibition of human immunodeficiency virus type 1 replication by an intracellular anti-Rev single-chain antibody. Proc Natl Acad Sci U S A 91(11): 5075-5079.

(56) References Cited

OTHER PUBLICATIONS

Emsley et al., (2010) Features and development of Coot. Acta Crystallogr D Biol Crystallogr 66(Pt 4): 486-501.
Engle et al., (2019) The glycan CA19-9 promotes pancreatitis and pancreatic cancer in mice. Science 364(6446): 1156-1162.
Fishwild et al., (1996) High-avidity human IgG kappa monoclonal antibodies from a novel strain of minilocus transgenic mice. Nat Biotechnol 14(7): 845-851.
Gietz and Schiestl (2007) Frozen competent yeast cells that can be transformed with high efficiency using the LIAc/SS carrier DNA/PEG method. Nat Protoc 2(1): 1-4.
Giudicelli et al., (2006) IMGT/LIGM-DB, the IMGT comprehensive database of immunoglobulin and T cell receptor nucleotide sequences. Nucleic Acids Res 34(Database issue): D781-D784.
Hoogenboom and Winter (1992) By-passing immunisation. Human antibodies from synthetic repertoires of germline VH gene segments rearranged in vitro. J Mol Biol 227(2): 381-388.
Houghton et al., (2017) Preloading with Unlabeled CA19.9 Targeted Human Monoclonal Antibody Leads to Improved PET Imaging with 89Zr-5B1. Mol Pharm 14(3): 908-915.
Huston et al., (1988) Protein engineering of antibody binding sites: recovery of specific activity in an anti-digoxin single-chain Fv analogue produced in *Escherichia coli.* Proc Natl Acad Sci U S A 85(16): 5879-5883.
Inbar et al., (1972) Localization of antibody-combining sites within the variable portions of heavy and light chains. Proc Natl Acad Sci U S A 69(9): 2659-2662.
Jahan et al., (2019) Trefoil factor(s) and CA19.9: A promising panel for early detection of pancreatic cancer. EBioMedicine 42: 375-385.
Jones et al., (1986) Replacing the complementarity-determining regions in a human antibody with those from a mouse. Nature 321(6069): 522-525.
Kabsch (2010) Integration, scaling, space-group assignment and post-refinement. Acta Crystallogr D Biol Crystallogr 66(Pt 2): 133-144.
Kannagi et al., (2004) Carbohydrate-mediated cell adhesion in cancer metastasis and angiogenesis. Cancer Sci 95(5): 377-384.
Kletter et al., (2015) Exploring the specificities of glycan-binding proteins using glycan array data and the GlycoSearch software. Methods Mol Biol. Author manuscript; available in PMC Jul. 22, 2015. Published in final edited form as: Methods Mol Biol. 2015; 1273: 203-214.
Köhler and Milstein (1975) Continuous cultures of fused cells secreting antibody of predefined specificity. Nature 256 (5517): 495-497.
Koprowski et al., (1979) Colorectal carcinoma antigens detected by hybridoma antibodies. Somatic Cell Genet 5(6): 957-971.
Kozbor et al., (1985) Specific immunoglobulin production and enhanced tumorigenicity following ascites growth of human hybridomas. J Immunol Methods 81(1): 31-42.
Langereis et al., (2015) Complexity and Diversity of the Mammalian Slalome Revealed by Nidovirus Virolectins. Cell Rep 11(12): 1966-1978.
Larrick and Fry (1991) PCR amplification of antibody genes. Methods 2(2): 106-110.
Lonberg and Huszar (1995) Human antibodies from transgenic mice. Int Rev Immunol 13(1): 65-93.
Lonberg et al., (1994) Antigen-specific human antibodies from mice comprising four distinct genetic modifications. Nature 368(6474): 856-859.
MacCallum et al., (1996) Antibody-antigen interactions: contact analysis and binding site topography. J Mol Biol 262(5): 732-745.
Makabe et al., (2008) Thermodynamic consequences of mutations in vernier zone residues of a humanized anti- human epidermal growth factor receptor murine antibody, 528. J Biol Chem 283(2): 1156-1166.
Marasco et al., (1998) Intracellular antibodies against HIV-1 envelope protein for AIDS gene therapy. Hum Gene Ther 9(11): 1627-1642.
Marks et al., (1991) By-passing immunization. Human antibodies from V-gene libraries displayed on phage. J Mol Biol 222(3): 581-597.
Marks et al., (1992) By-passing immunization: building high affinity human antibodies by chain shuffling. Biotechnology (N Y) 10(7): 779-783.

* cited by examiner

SLe$^a$βProNH$_2$

Fig. 16
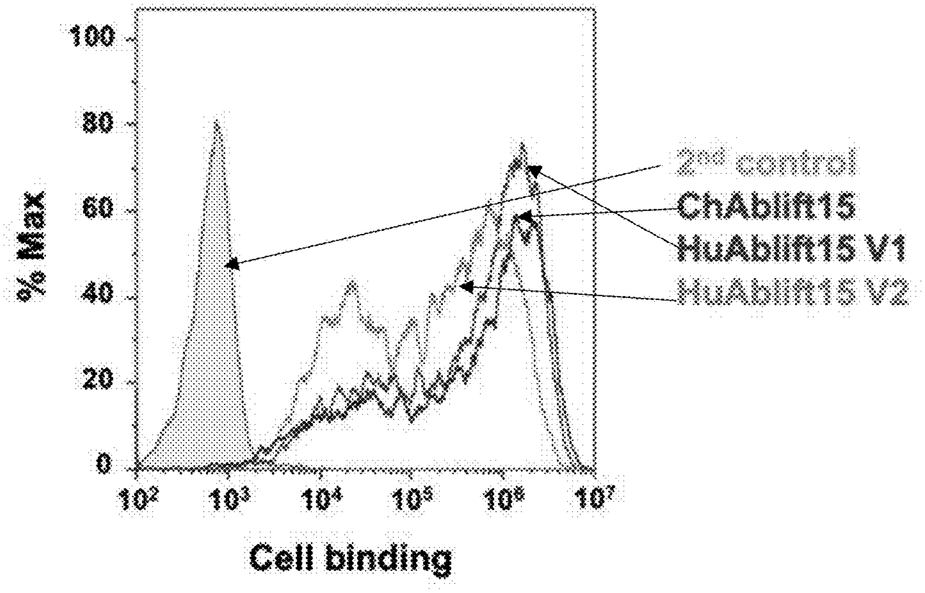
Fig. 17A
Fig. 17B
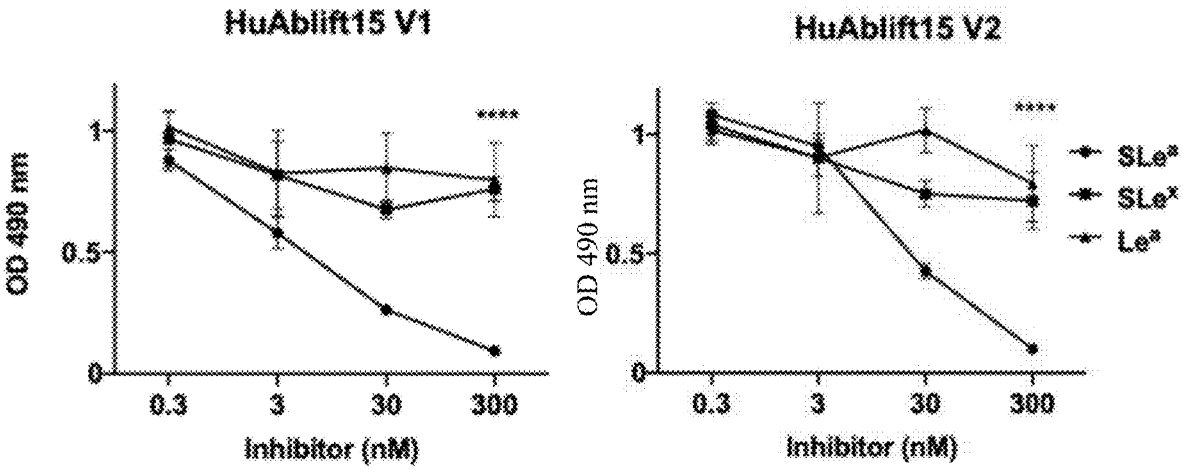

Figure 19C

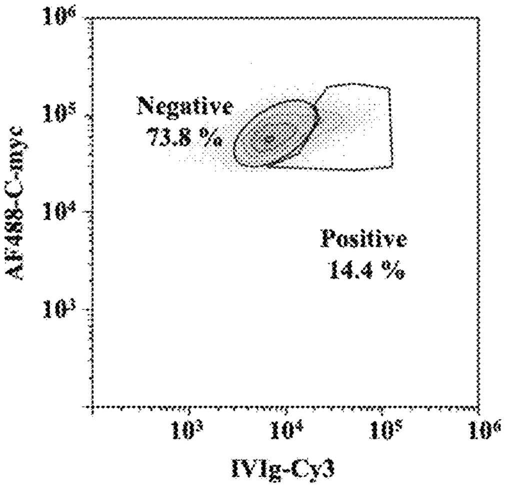

Figure 19D

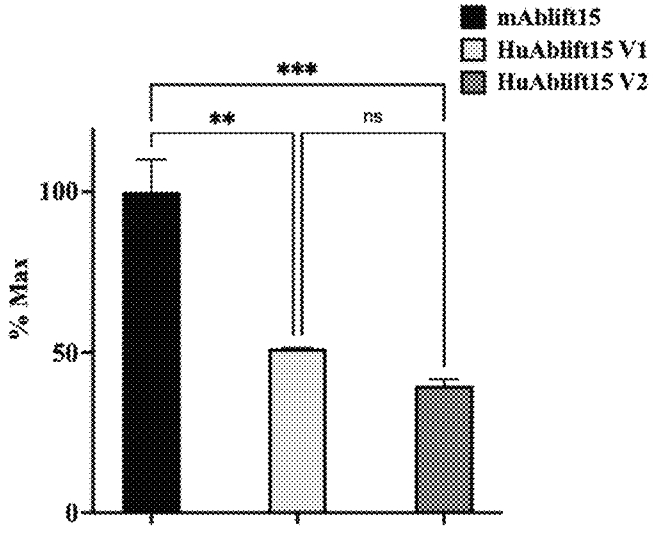

Fig. 20A

VH

```
Native      EVKLEESGGGLVQPGGSMKLSCAASGFTFSDAWMDWVRQSPEKGLEWVAEIGNKGNNHAT    60
Ablift2     EVKLEESGGGLVQPGGSMKLSCAASGFTFSDAWMDWVRQSPEKGLEWVAEIGNKGNNHAT    60
Ablift15    EVKLEESGGGLVQPGGSMKLSCAASGFTFSDAWMDWVRQSPEKGLEWVAEIGNKGNNHAT    60
            ************************************************************

Native      YYAESVKGRFTVSRDDSKSRVYLQMNSLRVEDTGTYYCTTRFAYWGQGTLVTVSA    115
Ablift2     YYAESVKGRFTVSRDDSKSRVYLQMNSLRVEDTGTYYCVVRFAYWGQGTLVTVSA    115
Ablift15    YYAESVKGRFTVSRDDSKSRVYLQMNSLRVEDTGTYYCAVRFAFWGQGTLVTVSA    115
            **************************************..***:***********
```

Fig. 20B

VL

```
Native      DIKMTQSPSSMYASLGERVTITCKASQDINSYLSWFQQKPGKSPKTLIYRANRLVDGVPS    60
Ablift2     DIKMTQSPSSMYASLGERVTITCKASQDINSYLSWFQQKPGKPPKTLIYRANRLVAGVPS    60
Ablift15    DIKMTQSPSSMYASLGERVTITCKASQDINSYLSWFQQKPGKPPKTLIYRANRLVPGVPS    60
            ****************************************** ************ ****

Native      RFSGSGSGQDYSLTISSLEYEDMGIYYCLQYDEFPRTFGGGTKLEIK    107
Ablift2     RFSGSGSGQDYSLTISSLEYEDMGIYWCLQYDEFPRTWGGGTKLEIK    107
Ablift15    RFSGSGSGQDYSLTISSLEYEDMGIYWCLQYDEFPRTWGGGTKLEIK    107
            **************************:**********:*********
```

ANTIBODIES TO CANCER GLYCOSYLATION AND USES THEREOF

The sequence listing in ASCII text file format of 38,961 bytes in size, created on Feb. 6, 2024, with the file name "2024-02-08SequenceListing padler6," filed in the U.S. Patent and Trademark Office on even date herewith, is hereby incorporated herein by reference.

FIELD OF THE INVENTION

The present invention relates to monoclonal antibodies to a glycoside Sialyl Lewis A known to be overexpressed in several cancers, fragments thereof and conjugates thereof, as well as chimeric antigen receptors, comprising same, cells comprising any of the above, compositions and uses thereof.

BACKGROUND OF THE INVENTION

Cancer manifests with a multifaceted loss of healthy cellular pathways resulting in a display of altered genes and proteins, in return, these altered macromolecules can serve as markers for diagnosing and targeting cancer. Aberrant glycosylation in cancer, although less targeted in therapies, has a significant presence. Disrupted enzymatic pathways of glycan synthesis in cancerous cells result in an altered glycan display with respect to glycans compositions synthesized and incorporated. Since glycans are involved in many cellular pathways including, among others, cell adhesion, cell communication, and migration, the outcome of altered glycosylation can result in many of the notorious cancerous phenotypes. To illustrate, the up-regulation of fucosyltransferases is frequent in many cases of cancers and is linked to cancer cell proliferation, immune evasion, angiogenesis, as well as metastasis. This altered profile of glycosylation, characteristic of cancerous cells is suggested to be a universal aspect of cancer.

Carbohydrate antigen 19-9 (CA19-9) also known as Sialyl Lewis-A (SLeA; $SLe^a$) is the gold standard marker for staging and prognosis mostly of pancreatic cancer, and some other types of cancers (Ugorski et al., Acta Biochim Pol. 2002; 49:303-311 and Ballehaninna U K, Chamberlain R S., Indian J Surg Oncol. 2011; 2:88-100). CA19-9 is an aberrant tetra saccharide composed of fucose (Fuc; FUC), N-acetylglucosamine (GlcNAc; NAG), galactose (Gal; GAL) and the termini sialic acid (Sia; SIA) which can be found on the surface of cancer cells as well as circulating in the blood. CA19-9 ($SLe^a$) tetrasaccharide stems from an incomplete synthesis of the normal glycan disialyl-$Le^a$. While both $SLe^a$ and disialyl-$Le^a$ are generated via the same metabolic pathway, reduction or loss of expression of the α2-6-sialyltransferase (ST6GalNAc VI) during malignancy shifts the pathway towards expression of the cancer antigen $SLe^a$ (FIG. 1). CA19-9 is also present in other cancer types with the majority being of gastrointestinal origin. A recent study in a mouse model indicated CA19-9 to be an active driver of pancreatitis leading to pancreatic cancer by that assigning an active role for CA19-9 as opposed to a standby marker. Importantly, monoclonal antibodies (mAbs) targeting CA19-9 were able to reverse pancreatitis in this mouse model, establishing CA19-9 as a prime target for cancer therapy, and high affinity antibodies against this target showed improved cancer cell binding and cytotoxicity (Amon et al., Cancers 2020, 12 (10), 2824).

Targeting CA19-9 for cancer staging and prognosis is currently commonly performed with mAb 1116NS19.9 (Koprowski, H. et al. Somatic Cell Genet. 5, 957-971 (1979). Despite being an important cancer marker, the molecular basis for CA19-9 recognition by antibodies is unknown. MAb 1116NS19.9 is a selective binder for CA19-9 and the common component of commercial kits for staging, and prognosis of pancreatic cancer. MAb 5b1 is another selective binder of CA19-9, obtained from human blood monocytes of CA19-9 immunized individuals and therefore a fully human Ab. MAb 5b1 and its conjugated forms suitable for radioimmunotherapy and PET imaging are currently in clinical trials for diagnosing and treating CA19-9 positive malignancies. Houghton et al., Mol. Pharm. 14, 908-915 (2017). WO 2021105988 relates to monoclonal antibodies and functional fragments thereof that specifically bind to SLeA carbohydrate antigen with high specificity and selectivity. The invention further provides compositions comprising the antibodies or fragments thereof as well as uses of the antibodies, fragments and compositions. WO2021105989 refers to chimeric antigen receptors (CARs) that specifically recognize and bind to SLeA carbohydrate antigen with high specificity and selectivity. The invention further provides lymphocytic cells, such as T cells, comprising said CARs, compositions comprising said cells or CARs as well as uses thereof.

There is a continuous need for development of novel and effective therapeutic agents targeting SLeA glycan which is expressed in many cancer types. Such agents could potentially be used for the treatment and diagnostics of a wide range of cancer types.

SUMMARY OF THE INVENTION

The present invention provides in one aspect an isolated monoclonal antibody (mAb) or a fragment thereof that specifically binds to Sialyl Lewis A glycan (SLeA), wherein the mAb or the fragment comprises an antigen binding domain comprising a heavy-chain variable domain (VH) and a light-chain variable domain (VL) each comprising three complementarity determining regions (CDRs) and four framework domains (FR), wherein the VH-CDR 1 and 2 comprise amino acid sequences SEQ ID NOs: 3 and 4, respectively, VH-CDR 3 comprises an amino acid sequence selected from SEQ ID NO: 5 and 9; VL-CDRs 1 and 3 comprise amino acid sequences SEQ ID NOs: 6 and 12, respectively; and VL-CDR 2 comprises an amino acid sequence selected from SEQ ID NO: 10 and SEQ ID NO: 11. According to some embodiments, the VH-FR3 comprises an amino acid sequence selected from SEQ ID NO: 13 and 14; and VL-FR2 and VL-FR3 comprise amino acid sequences SEQ ID NOs: 15 and 16, respectively.

According to some embodiments, the isolated mAb or a fragment thereof comprises a VH and VL domain comprising amino acid sequences SEQ ID NO: 1 and SEQ ID NO: 2, respectively, wherein (i) the VH comprises at least one substitution at a position selected from position 99, 100 and 104; and (ii) the VL comprises a substitution at positions 56 and 98 and at least one additional amino acid substitution at a position selected from positions 43 and 87, wherein the substitution in VH at positions 99 and 100, if present, is each for Val, Ala, Leu or Ile; the substitution in VH at position 104, if present, is for Phe or Trp; the substitution in VL at position 43, if present, is for Pro, the substitution in VL at position 56 is for Val or Ala, the substitution in VL at positions 87, if present, is for Trp, and the substitution in VL at position 98 is each for Trp.

According to some embodiments, the isolated mAb or a fragment thereof comprises a VH comprising an amino acid sequence selected from SEQ ID NO: 17 and 19 and the VL comprises an amino acid sequence selected from SEQ ID NO: 18 and 20, or a functional analog thereof having at least 90% sequence identity to the sequences and no substitution is introduced into CDRs, into positions 99 and 100 of VH and into positions 43 and 87 of VL.

According to some embodiments, the isolated mAb or a fragment thereof comprises a VH comprising amino acid SEQ ID NO: 17 and a VL comprising amino acid sequence SEQ ID NO: 18, or a functional analog thereof having at least 90% sequence identity to the sequences and no substitution is introduced into CDRs, into positions 99 and 100 of SEQ ID NO: 17 and into positions 43 and 87 of SEQ ID NO: 18.

According to some embodiments, the fragment is a single chain variable fragment (scFv). According to some embodiments the scFv comprises amino acid sequences SEQ ID NO: 17 and SEQ ID NO: 18 or a functional analog thereof having at least 90% sequence identity to said sequence. According to some embodiments, the scFv comprises amino acid sequence SEQ ID NO: 21 or a functional analog thereof having at least 90% sequence identity to said sequence. According to some embodiments, the scFv comprises amino acid sequences SEQ ID NO: 19 and SEQ ID NO: 20, or amino acid sequence SEQ ID NO: 22, or an analog thereof having at least 90% sequence identity to said sequence.

According to some embodiments, the isolated mAb or the fragment thereof exhibits an increased affinity to CA19-9 as compared to an antibody comprising amino acid sequences SEQ ID NOs: 1 and 2. According to some embodiments, the isolated mAb or the fragment thereof has $K_D$ of from 1 to 30 nM.

According to some embodiments, the isolated mAb or the fragment thereof is humanized. According to some embodiments, the humanized antibody or the fragment comprises a VH domain comprising an amino acid sequence selected from SEQ ID NO: 17 and SEQ ID NO: 1 and a VL domain comprising amino acid sequence SEQ ID NO:18, wherein from 10 to 26 amino acid residues in the framework regions in VH and in VL are further substituted and wherein the substituted amino acids are not at positions 99 and 100 of the VH and not at positions 43 and 87 of the VL. According to some embodiments, the humanized antibody or the fragment comprises a VH domain comprising an amino acid sequence selected from SEQ ID NO: 23 and 25 and the VL comprising amino acid sequence SEQ ID NO: 24. According to some embodiments, the humanized antibody fragment is scFv. According to some embodiments, the humanized antibody fragment comprises an amino acid sequence selected from SEQ ID NO: 26 and 27. According to some embodiments, the humanized antibody or the fragment comprises a VH domain comprising an amino acid sequence SEQ ID NO: 19 and a VL domain comprising an amino acid sequence SEQ ID NO: 20, wherein from 10 to 26 amino acid residues in the framework regions in VH and in VL are further substituted and wherein the substituted amino acids are not at positions 99 and 100 of the VH and not at positions 43 and 87 of the VL. According to some embodiments, the humanized antibody or the fragment has KD of from 1 to 90 nM.

According to another aspect, the present invention provides a conjugate of the isolated monoclonal antibody or the fragment of the present invention.

According to another aspect, the present invention provides a chimeric antigen receptor (CAR) comprising the mAb, the fragment thereof, the humanized mAb or the fragment thereof of the present invention. According to some embodiments, the CAR comprises one of the following (i) a VH and VL comprising amino acid sequences SEQ ID NO: 17 and 18, respectively; (ii) a VH and VL comprising amino acid sequences SEQ ID NO: 19 and 20, respectively; (iii) a VH and VL comprising amino acid sequences SEQ ID NO: 23 and 24, respectively; (iv) a VH and VL comprising amino acid sequences SEQ ID NO: 25 and 24, respectively; (v) a single chain variable fragment (scFv) comprising an amino acid sequence selected from SEQ ID NO: 21 and 22; (vi) a humanized scFv comprising an amino acid sequence selected from SEQ ID NO: 26 and 27; or (vii) an analog of any one of (i)-(vi) having at least 90% sequence identity to the sequence and no substitution is introduced into CDRs, into positions 99 and 100 of VH and into positions 43 and 87 of VL.

According to some embodiments, the CAR of the present invention comprises a transmembrane domain (TM domain), one or more costimulatory domains, and an activation domain. According to some embodiments, the CAR is characterized by at least one of (i) the TM domain is a TM domain of a receptor selected from CD28 and CD8, or an analog thereof having at least 85% amino acid identity to the original sequence; (ii) the costimulatory domain is selected from a costimulatory domain of a protein selected from CD28, 4-1BB, OX40, iCOS, CD27, CD80, CD70, an analog thereof having at least 85% amino acid identity to the original sequence, and any combination thereof; (iii) the antigen binding domain is linked to the TM domain via a spacer; (iv) the activation domain is selected from FcRy and CD3-ζ activation domains; or (v) further comprising a leading peptide.

According to another aspect, the present invention provides a nucleic acid molecule encoding at least one chain of the monoclonal antibody or fragment thereof of the present invention, or at least one chain of the humanized mAb or fragment thereof of the present invention, or the CAR of the present invention, or a conservative variant of said nucleic acid molecule having at least 90% sequence identity to said sequence.

According to some embodiments, the nucleic acid molecule encodes at least one amino acid sequence selected from SEQ ID NOs: 17-27. According to some embodiments, the nucleic acid molecule comprises at least one nucleic acid sequence selected from SEQ ID NOs: 30-39.

According to another aspect, the present invention provides a nucleic acid construct comprising the nucleic acid molecule of the present invention, operably linked to a promoter.

According to another aspect, the present invention provides a vector comprising the nucleic acid molecule or the nucleic acid construct of the present invention.

According to another aspect, the present invention provides a cell comprising at least one of (i) the mAb or the fragment thereof of the present invention, (ii) the humanized mAb or fragment of the present invention, (iii) the CAR of the present invention, (iv) the nucleic acid molecule of the present invention, (v) the nucleic acid construct of the present invention, or (vi) the vector of the present invention. According to some embodiments, the cell expresses or is capable of expressing the CAR of the present invention. According to some embodiments, the cell is selected from a T cell and a natural killer (NK) cell. According to some embodiments, the cell is selected from T cells comprising the CAR of the present invention.

According to another aspect, the present invention provides a composition comprising at least one of the followings: (i) the isolated mAb or the fragment thereof of the present invention, (ii) the humanized mAb or fragment of the present invention, (iii) the CAR of the present invention, (iv) the conjugates of the present invention, or (v) a plurality of cells of the present invention, and a carrier. According to some embodiments, the composition is a pharmaceutical composition and the carrier is pharmaceutically acceptable. Thus, according to one aspect, the present invention provides a pharmaceutical composition comprising at least one of the followings: (i) the isolated mAb or the fragment thereof of the present invention, (ii) the humanized mAb or fragment of the present invention, (iii) the CAR of the present invention, (iv) the conjugates of the present invention, or (v) a plurality of cells of the present invention, and a pharmaceutically acceptable carrier. According to some embodiments, the pharmaceutical composition comprises a plurality of T cells comprising the CAR of the present invention and a pharmaceutically acceptable carrier. According to some embodiments, the pharmaceutical composition comprises a plurality of T cells comprising a nucleic acid molecule of the present invention encoding the CAR of the present invention and a pharmaceutically acceptable carrier.

According to some embodiments, the pharmaceutical composition of the present invention is for use in treating cancer. According to some embodiments, the cancer is characterized by overexpression of SleA glycan. According to some embodiments, the cancer is selected from pancreatic, breast, lung, ovarian, colon, stomach, oropharyngeal cancer, squamous cell carcinoma, head and neck and gallbladder cancer. According to some embodiments, the cancer is selected from lung adenocarcinoma, pancreatic adenocarcinoma, colon adenocarcinoma, Her-2 negative breast carcinoma and pharynx squamous cell carcinoma.

According to some embodiments, the composition of the present invention is for use in quantification of SLeA in the sample comprising contacting a sample with the monoclonal antibodies or antibody fragments or the conjugate of the present invention, and assessing the amount of SLeA in the sample, and optionally comparing the amount of SLeA in the sample to a reference. According to some embodiments, the composition of the present invention is for use in diagnosing or monitoring cancer progression or treatment comprising contacting a biological sample of the subject with the monoclonal antibodies or antibody fragments or the conjugate of the present invention, and assessing the amount of SLeA in the sample, and optionally comparing the amount of SLeA in the sample to a reference, wherein the cancer overexpresses SLeA glycan. According to some embodiments, the use is diagnosing cancer and comprising comparing the assessed amount of SLeA in the sample to a threshold or to a reference, wherein the reference is the level of SLeA in the sample of healthy subjects, and wherein the amount of the SLeA in the sample above the reference or the threshold is indicative of the CA19-9+ malignancy. According to some embodiments, the use comprises monitoring cancer progression or cancer treatment and the reference is a level of SLeA in the previous sample of the subject, and a decrease in the amount of SLeA in comparison to the reference is indicative of amelioration of cancer.

According to another aspect, the present invention provides a method for treating cancer in a subject in need thereof comprising administering to said subject a therapeutically effective amount of at least one of the followings: isolated monoclonal antibodies or fragments thereof of the present invention, the conjugates of the present invention, the CAR of the present invention, the cells of the present invention or the pharmaceutical composition of the present invention.

According to another aspect, the present invention provides a method for diagnosing or monitoring cancer in a subject, the method comprises contacting a biological sample of the subject with the monoclonal antibodies or antibody fragments or the conjugate of the present invention, preferably under conditions allowing immunocomplexes formation, and assessing the amount of SLeA in the sample, wherein the cancer overexpresses SLeA glycan.

According to some embodiments, the method for diagnosing cancer comprises comparing the assessed amount of SLeA in the sample to a threshold or to a reference, wherein the reference is the level of SLeA in the sample of healthy subjects, and wherein the amount of the SLeA in the sample above the reference or the threshold is indicative of the CA19-9+ malignancy.

According to some embodiments, the method for monitoring cancer comprises monitoring the progression or monitoring cancer treatment, wherein the method comprises comparing the amount of SLeA in the sample to the reference being the level of SLeA in the previous sample of the subject, and a decrease in the amount of SLeA in comparison to the reference is indicative of amelioration of cancer.

According to some embodiments, following diagnosis, the method further comprises recommendations for treatment of the cancer. According to some embodiments, following diagnosis, the method further comprises treatment of the cancer.

According to another aspect, the present invention provides a kit for diagnosing or monitoring cancer in a subject, wherein the kit comprises the monoclonal antibodies or the conjugate of the present invention and means for detecting the amount of the antibodies, antibody fragments or conjugates thereof that formed complexes with SLeA present in a biological sample of the subject, thereby detecting the amount or level of SLeA in the biological sample. According to some embodiments, the kit comprises instructions for use.

BRIEF DESCRIPTION OF THE DRAWING

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 7 show that the scFv-Ablift-YSD clone is specific to $SLe^a$ and have a higher affinity than the scFv-Native-YSD.

FIG. 12 shows amino acid multiple sequence alignment (MSA) of the mouse-derived Ablift15 antibody (mAblift15) and its humanized versions.

FIG. 16 shows binding of chimeric and humanized full-length antibodies against cancer cells. Binding of chimeric (blue) and humanized (red and green) of Ablift15 IgGs to $SLe^a$-expressing WiDr cancer cells was examined by FACS at 5 ng/μL. Representative of two independent experiments.

FIG. 17 shows specificity of the full-length HuAblift15 V1 (FIG. 17A) and HuAblift15 V2 (FIG. 17B) IgGs examined by ELISA inhibition assay against coated $SLe^a$-PAA-biotin, after pre-incubation of the antibody with specific ($SLe^a$) or non-specific glycans ($SLe^x$ and $Le^a$). ****p<0.001.

FIG. 20 shows amino acid multiple sequence alignment (MSA) of the mouse-derived Ablift antibodies (mAblift2 and mAblift15) and the original sequence from which they were derived (Native) FIG. 20A-VH domain and FIG. 20B-VL domain.

DETAILED DESCRIPTION OF THE INVENTION

Figure 1:
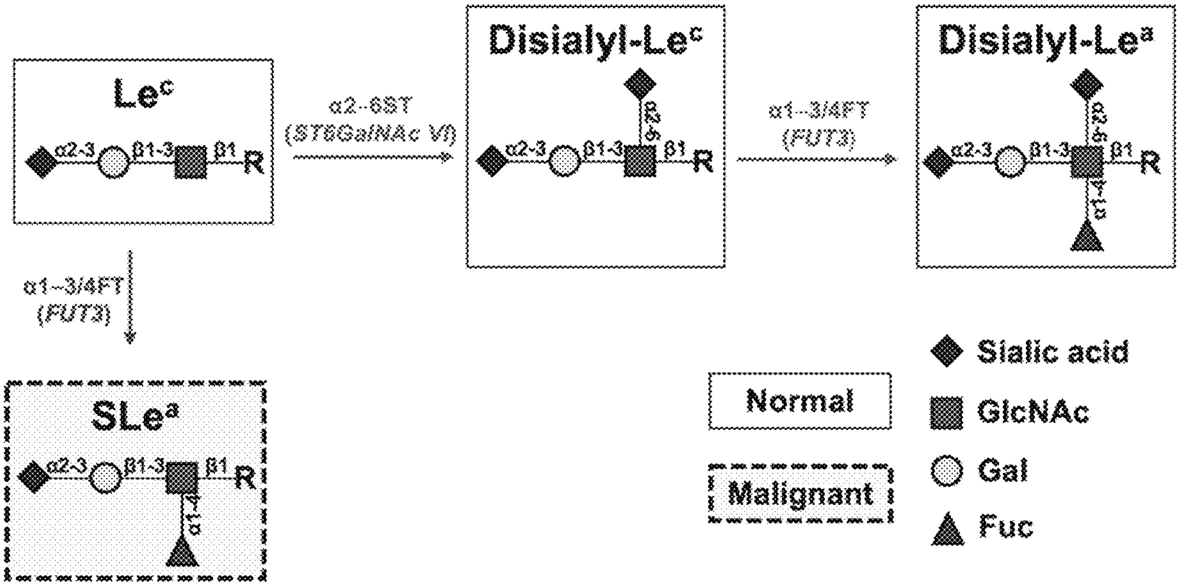
FIG. 1 shows the pathway leading to the expression of the cancer glycan CA19-9 versus the normal glycan disialyl-$Le^a$. In cases of epigenetic silencing of α2-6-sialyltransferase which is prevalent in cancer, there is an accumulation of CA19-9 in affected tissue.

Unless otherwise defined, all technical and/or scientific terms used herein have the same meaning as commonly understood by one of ordinary skill in the art to which the invention pertains. In case of conflict, the patent specification, including definitions, will control. Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present invention, in some embodiments thereof, relates to antibodies to cancer glycosylation and uses thereof.

Using high-resolution structural data of two monoclonal antibodies: Ab 1116NS19.9 and Ab 5b1 each bound to CA19-9 (SleA), the inventors of the present application found that both antibodies target practically the same low-energy conformer of CA19-9 utilizing distinct binding mechanisms. Using the structural data of Ab 1116NS19.9 and rational design, several modified antibodies (Abs) were prepared. Some of these modified Abs reached a 10-fold enhanced affinity, improved cancer cell binding and cytotoxicity. Besides rationalizing the CA19-9 recognition, the present data suggest a potential enhanced tool for improving diagnosis and treatment of cancer overexpressing SleA, such as pancreatic cancer.

According to one aspect, the present invention provides a monoclonal antibody (mAb) or a fragment thereof that specifically binds to Sialyl Lewis A glycan (SLeA), wherein the mAb or the fragment comprises an antigen binding domain comprising a heavy-chain variable domain (VH) and a light-chain variable domain (VL) each comprising three complementarity determining regions (CDRs) and four framework domains (FR), wherein the VH-CDR 1 and 2 comprise amino acid sequences SEQ ID NOs: 3 and 4, respectively, VH-CDR 3 comprises an amino acid sequence selected from SEQ ID NO: 5 and 9; VL-CDRs 1 and 3 comprise amino acid sequences SEQ ID NOs: 6 and 12, respectively; and VL-CDR 2 comprises an amino acid sequence selected from SEQ ID NO: 10 and SEQ ID NO: 11. According to any one of the aspects and embodiments of the present invention, the mAb or the fragment is an isolated. Thus, the present invention provides an isolated mAb and fragments thereof.

According to any one of the embodiments of the application, any embodiment referring to "an isolated monoclonal antibody (mAb) or a fragment thereof" encompasses also separate embodiment referring to "an isolated monoclonal antibody" and a separate embodiment referring to "a fragment". Thus, each one of such embodiments may be drafted separately for the mAb and for fragment and each such separate embodiment is encompassed by the application.

According to some embodiments, the isolated monoclonal antibody (mAb) or a fragment thereof comprises a VH and VL each comprising three CDRs, wherein VH-CDR 1, 2 and 3 comprise or consist of amino acid sequences SEQ ID NOs: 3, 4 and 5, respectively and VL-CDR 1, 2 and 3 comprise or consist of amino acid sequences SEQ ID NOs 6, 10 and 12, respectively.

According to some embodiments, the isolated monoclonal antibody (mAb) or a fragment thereof comprises a VH and VL each comprising three CDRs, wherein VH-CDR 1, 2 and 3 comprise or consist of amino acid sequences SEQ ID NOs: 3, 4 and 9, respectively, and VL-CDR 1, 2 and 3 comprise or consist of amino acid sequences SEQ ID NOs 6, 11 and 12, respectively.

According to some embodiments, the isolated mAb or the fragment thereof comprises VH-FR3 comprising amino acid sequence SEQ ID NO: 13. According to some embodiments, the isolated mAb or the fragment comprises VH-FR3 comprising amino acid sequence SEQ ID NO: 14. According to another embodiment, the isolated mAb or the fragment comprises VL-FR2 comprising amino acid sequences SEQ ID NO: 15. According to another embodiment, the isolated mAb or the fragment comprises VL-FR3 comprising amino acid sequence SEQ ID NOs: 16.

According to some embodiments, the isolated mAb or the fragment comprises VH-FR3 comprising an amino acid sequence selected from SEQ ID NO: 13 and 14; and VL-FR2 and VL-FR3 comprising amino acid sequences SEQ ID NOs: 15 and 16, respectively.

According to some embodiments, the isolated monoclonal antibody (mAb) or a fragment thereof comprises a VH and VL each comprising three CDRs and four framework domains (FR), wherein VH-CDR 1, 2 and 3 comprise or consist of amino acid sequences SEQ ID NOs: 3, 4 and 5, respectively, VL-CDR 1, 2 and 3 comprise or consist of amino acid sequences SEQ ID NOs: 6, 10 and 12, respectively, VH-FR3 comprising or consisting of amino acid sequence SEQ ID NO: 13; and VL-FR2 and VL-FR3 comprising or consisting of amino acid sequences SEQ ID NOs: 15 and 16, respectively.

According to some embodiments, the isolated monoclonal antibody (mAb) or a fragment thereof comprises a VH and VL comprising three CDRs, wherein VH-CDR 1, 2 and 3 comprise or consist of amino acid sequences SEQ ID NOs: 3, 4 and 9, respectively and VL-CDR 1, 2 and 3 comprise or consist of amino acid sequences SEQ ID NOs: 6, 11 and 12, VH-FR3 comprising or consisting of amino acid sequence SEQ ID NO: 14; and VL-FR2 and VL-FR3 comprising or consisting of amino acid sequences SEQ ID NOs: 15 and 16, respectively.

Considering that some of the antibodies of the present invention are modifications of Ab 1116NS19.9 having a VH and VL domain comprising amino acid sequence SEQ ID NOs: 1 and 2, respectively, in some embodiments, the reference is made to positions of the amino acids in these sequences.

According to some examples, the present invention provides an isolated antibody comprising an amino acid sequence of a light chain (VL) as set forth in SEQ ID NO: 2 and a heavy chain (VH) as set forth in SEQ ID NO: 1, wherein at least one of the VL and the VH comprises at least one amino acid substitution selected from the group consisting of:

| | |
|---|---|
| Position 43 in VL | substitution to Pro or a conservative substitution thereof; |
| Position 56 in VL | substitution to Val, Pro or a conservative substitution thereof; |
| Position 87 in VL | substitution to Trp or a conservative substitution thereof; |
| Position 98 in VL | substitution to Trp or a conservative substitution thereof; |
| Position 35 in VH | substitution to Asp or a conservative substitution thereof; |
| Position 93 in VH | Substitution to Val, Ala or a conservative substitution thereof; |

-continued

| | |
|---|---|
| Position 94 in VH | substitution to Val or a conservative substitution thereof; |
| Position 98 in VH | substitution to Tyr, Phe or a conservative substitution thereof; and |

wherein the antibody binds carbohydrate antigen 19-9 (CA19-9). According to some embodiments, the isolated antibody further comprises a substitution at position 35 of the VH to D or a conservative substitution thereof. According to some embodiments of the invention, the at least one amino acid substitution comprises at least three amino acid substitutions.

According to some embodiments of the invention, the at least one amino acid substitution comprises at least four amino acid substitutions. According to some embodiments of the invention, the at least one amino acid substitution comprises at least five amino acid substitutions. According to some embodiments of the invention, the at least one amino acid substitution is at the VL and VH. According to some embodiments of the invention, the at least one amino acid substitution is at VL Y87 and alternatively or additionally F98. According to some embodiments of the invention, the at least one amino acid substitution is at positions 43, 56, 87 and 98 of the VL and 35, 93, 94 and optionally 98 of the VH. In the above examples, the numbering of the amino acids is according to KABAT system, which may be different from the sequential numbering of amino acids in the amino acid sequence of an antibody. In this case, the KABAT numbering for VL corresponds to sequential numbering. However, the KABAT numbering for VH does not correspond to sequential plain numbering. Thus, amino acid positions 35, 93, 94 and 98 according to KABAT in SEQ ID NO: 1 correspond to positions 35, 99, 100 and 104 of the plain sequence SEQ ID NO: 1.

In the present application, unless explicitly stated, the numbering refers to sequential numbering, i.e. the position of the amino acid in the plain amino acid sequence.

According to some embodiments, the present invention provides an isolated monoclonal antibody (mAb) or a fragment thereof that specifically binds to Sialyl Lewis A glycan (SLeA), wherein the mAb or the fragment comprises an antigen binding domain comprising a VH domain comprising amino acid sequence SEQ ID NO: 1 and a VL domain comprising an amino acid sequence SEQ ID NO: 2, wherein each of the VH and VL domains comprises three CDRs and four framework domains (FR), and wherein VH-CDR3 comprises an amino acid Phe, Tyr or Trp at position 104 of SEQ ID NO: 1, the VL-CDR2 comprises an amino acid selected from Pro, Ala, Val, Leu and Ile at position 56 of SEQ ID NO: 2 and VL-CDR3 comprises amino acid Trp at position 98 of SEQ ID NO: 2. According to some embodiments, the VH-CDR3 comprises an amino acid Tyr at position 104 of SEQ ID NO: 1, the VL-CDR2 comprises an amino acid Ala at position 56 of SEQ ID NO: 2 and VL-CDR3 comprises amino acid Trp at position 98 of SEQ ID NO: 2. According to some embodiments, the VH-CDR3 comprises an amino acid Tyr at position 104 of SEQ ID NO: 1, the VL-CDR2 comprises an amino acid Pro at position 56 of SEQ ID NO: 2 and VL-CDR3 comprises amino acid Trp at position 98 of SEQ ID NO: 2.

According to some embodiments, the isolated mAb or the fragment further comprises a substitution at position 99 of SEQ ID NO: 1 for an amino acid selected from Ala, Val, Leu and Ile. According to one embodiment, the substitution at positions 99 of SEQ ID NO: 1 for an amino acid Ala. According to one embodiment, the substitution at positions 99 of SEQ ID NO: 1 is for an amino acid Val.

According to some embodiments, the isolated mAb or the fragment further comprises a substitution at positions 100 of SEQ ID NO: 1 for an amino acid selected from Ala, Val, Leu and Ile. According to one embodiment, the substitution at positions 100 of SEQ ID NO: 1 for amino acid Val.

According to some embodiments, the isolated mAb or the fragment further comprises a substitution at position 43 of SEQ ID NO: 2 for Pro.

According to some embodiments, the isolated mAb or the fragment further comprises a substitution at position 87 of SEQ ID NO: 2 for Trp.

According to some embodiments, the isolated mAb or the fragment further comprises 2, 3, o 4 substitutions selected from (i) substitution at positions 99 of SEQ ID NO: 1 for an amino acid selected from Ala and Val; (ii) substitution at positions 100 of SEQ ID NO: 1 for amino acid Val; (iii) substitution at positions 43 of SEQ ID NO: 2 for Pro; and (iv) substitution at positions 87 of SEQ ID NO: 2 for Trp.

According to some embodiments, the present invention provides an isolated mAb or a fragment thereof that specifically binds to SLeA, wherein the mAb or the fragment comprises an antigen binding domain comprising a VH domain comprising an amino acid sequence SEQ ID NO: 1 and a VL domain comprising an amino acid sequence SEQ ID NO: 2, wherein (i) the VH comprises at least one amino acid substitution at a position selected from 99, 100 and 104; and (ii) the VL comprises at least one amino acid substitution at a position selected from 43, 56, 87 and 98; wherein the substitution in VH at positions 99 and 100 is each for Val, Ala or a conservative substitution thereof; the substitution in VH at position 104 is for Phe or Trp; the substitution in VL at position 43 is for Pro, the substitution in VL at position 43 is for Pro, Val or a conservative substitution thereof, and the substitution in VL at positions 87 and 98 is each for Trp.

According to one embodiment, the mAb or the fragment comprises a VH and VL domain comprising amino acid sequences SEQ ID NO: 1 and SEQ ID NO: 2, respectively, wherein (i) the VH comprises at least one substitution at a position selected from position 99, 100 and 104; and (ii) the VL comprises a substitution at positions 56 and 98 and at least one additional amino acid substitution at a position selected from positions 43 and 87, wherein the substitution in VH at positions 99 and 100, if present, is each for Val, Ala, Leu or Ile; the substitution in VH at position 104, if present, is for Phe or Trp; the substitution in VL at position 43, if present, is for Pro, the substitution in VL at position 56 is for Val or Ala, the substitution in VL at positions 87, if present, is for Trp, and the substitution in VL at position 98 is each for Trp. According to another embodiment, the mAb or the fragment comprises an antigen binding domain comprising a VH and VL domains comprising amino acid sequences SEQ ID NO: 1 and SEQ ID NO: 2, respectively, wherein (i) the VH comprises at least one substitution at a position selected from position 99, 100 and 104; and (ii) the VL comprises a substitution at positions 56 and 98 and at least one additional amino acid substitution at a position selected from positions at 43 and 87, wherein the substitution in VH at positions 99 and 100 is each for Val, Ala, Leu or Ile; the substitution in VH at position 104 is for Phe or Trp; the substitution in VL at position 43 is for Pro, the substitution in VL at position 56 is for Val or Ala, and the substitution in VL at positions 87 and 98 is each for Trp.

The terms "Sialyl Lewis A glycan", "SLea", SLeA", "CA19-9" and "SLeA" are used herein interchangeably and refer to Siaα2-3Galβ1-3 [Fucα-4]GlcNAc tetrasaccharide carbohydrate also known as antigen 19-9 (CA19-9), and having the structure as presented in structure I and schematically presented in FIG. 1. This tetrasaccharide can be conjugated to different underlying structures such as carbohydrate(s), protein, lipid, synthetic linker(s) or scaffold(s).

Structure I

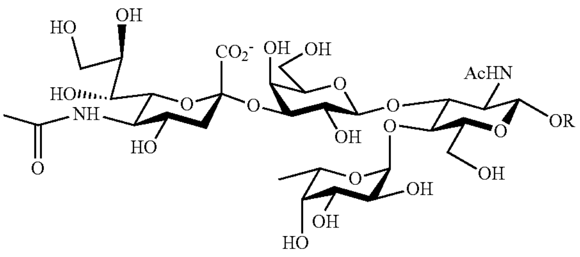

The terms "antibody", "antibodies" and "Ab" are used here interchangeably in the broadest sense and include monoclonal antibodies (including full length or intact monoclonal antibodies), polyclonal antibodies, multivalent antibodies, multi-specific antibodies (e.g., bi-specific antibodies), and antibody fragment long enough to exhibit the desired biological activity.

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (Fragment crystalline) domains. The term "antigen binding portion", "antigen binding region", "antigen binding site" and "antigen binding domain" are used herein interchangeably and refer to one or more fragments of an antibody that retain the ability to specifically bind to an antigen. The antigen binding domains, Fab, include regions where the polypeptide sequence varies. The term $F(ab')_2$ represents two Fab' arms linked together by disulfide bonds. The central axis of the antibody is termed the Fc fragment. Each heavy chain has at one end a variable domain (VH) followed by a number of constant domains (CH). Each light chain has a variable domain (VL) at one end and a constant domain (CL) at its other end, the light chain variable domain being aligned with the variable domain of the heavy chain and the light chain constant domain being aligned with the first constant domain of the heavy chain (CH1). The variable domains of each pair of light and heavy chains form the antigen-binding site. The domains of the light and heavy chains have the same general structure and each domain comprises four framework regions, whose sequences are relatively conserved, joined by three hyper-variable domains known as complementarity determining regions (CDRs). These domains contribute to the specificity and affinity of the antigen-binding site. The isotype of the heavy chain (gamma, alpha, delta, epsilon or mu) determines immunoglobulin class (IgG, IgA, IgD, IgE or IgM, respectively). The light chain is either of two isotypes (kappa (κ) or lambda (λ)) found in all antibody classes. The term "paratope" refers to the antigen binding site of an antibody or fragment thereof.

The terms "monoclonal antibody" and "mAb" are used herein interchangeably and refer to an antibody obtained from a population of substantially homogeneous antibodies, i.e., the individual antibodies comprising the population are identical except for possible naturally occurring mutations that may be present in minor amounts. Monoclonal antibodies (mAbs) are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring the production of the antibody by any particular method. mAbs may be obtained by methods known to those skilled in the art. For example, the monoclonal antibodies to be used in accordance with the present invention may be made by the Hybridoma method or may also be isolated from phage antibody libraries. As used herein, the term "epitope" refers to any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

The terms "fragment", "functional fragment" and "antibody fragment" are used herein interchangeably and refer to only a portion of an intact antibody, generally including an antigen-binding site of the intact antibody and thus retaining the ability to bind antigen. The term refers to the antibody as well as to the analog or variant of said antibody. The antibody fragment according to the teaching of the present invention is a function fragment, i.e. preserves the function of the intact antibody. Examples of antibody fragment encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 1989, 341, 544-546) which consists of a VH domain; (vii) isolated CDR regions; (viii) $F(ab')_2$ fragments, a bivalent fragment including two Fab' fragments linked by a disulphide bridge at the hinge region; (ix) single chain antibody molecules (e.g. single chain Fv; scFv) (Bird et al., Science 1988, 242, 423-426; and Huston et al., PNAS (USA) 1988, 85, 5879-5883); (x) "diabodies" with two antigen binding sites, comprising a heavy chain variable domain (VH) connected to a light chain variable domain (VL) in the same polypeptide chain; (xi) "linear antibodies" comprising a pair of tandem Fd segments (VH-CH1-VH-CH1) which, together with complementary light chain polypeptides, form a pair of antigen binding regions. According to a specific embodiment, the antibody fragments include, but are not limited to, single chain, Fab, Fab' and $F(ab')_2$ fragments, Fd, Fcab, Fv, dsFv, scFvs, diabodies, minibodies, nanobodies, Fab expression library or single domain molecules such as VH and VL that are capable of binding to an epitope of the antigen in an HLA restricted manner. According to some embodiments, the fragment is a scFv.

The terms "light chain variable region", "vL" and "VL" are used herein interchangeably and refer to a light chain variable region of an antibody capable of binding to SLeA glycan. The terms "heavy chain variable region", "vH" and "VH" are used herein interchangeably and refer to a heavy chain variable region of an antibody capable of binding to SLeA glycan.

As used herein, the term "CDR" refers to the complementarity determining region within antibody variable sequences. There are three CDRs in each one of the variable regions of the heavy chain and the light chain, which are designated CDR1, CDR2 and CDR3 (or specifically VH CDR1, VH CDR2, VH CDR3, VL CDR1, VL CDR2, and VL CDR3), for each of the variable regions. Determination of CDR sequences from antibody heavy and light chain variable regions can be made according to any method known in the art, including but not limited to the methods known as KABAT, Chothia and IMGT. The selected set of CDRs may include sequences identified by more than one method, namely, some CDR sequences may be determined using KABAT and some using IMGT. According to one embodiment, the CDRs are defined using KABAT method.

As used herein, the terms "framework", "framework region" or "framework sequence" refer to the remaining sequences of a variable region minus the CDRs. Because the exact definition of a CDR sequence can be determined by different systems, the meaning of a framework sequence is subject to correspondingly different interpretations. The six CDRs also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represent two or more of the four sub-regions constituting a framework region.

According to some embodiments, the antibody fragment is a single chain variable fragment (scFv) being a composite polypeptide having antigen binding capabilities and comprising amino acid sequences homologous or analogous to the variable regions of an immunoglobulin light and heavy chain i.e. linked VH-VL, VL-VH or single chain Fv (scFv).

According to some embodiments, the terms "antibody" or "antibodies" collectively refer to intact antibodies, i.e. humanized monoclonal antibodies (mAbs) and analogs thereof, as well as proteolytic fragments thereof, such as the Fab or $F(ab')_2$ fragments and scFv.

The terms "binds specifically" or "specific for" with respect to an antigen-binding domain of an antibody or of a fragment thereof refers to an antigen-binding domain which recognizes and binds to a specific antigen, but does not substantially recognize or bind other molecules, e.g. in a sample or in vivo. The term encompasses that the antigen-binding domain binds to its antigen with high affinity and binds other antigens with low affinity. An antigen-binding domain that binds specifically to an antigen from one species may bind also to that antigen from another species. This cross-species reactivity is not contrary to the definition of that antigen-binding domain as specific.

The term "isolated", when applied to a nucleic acid or protein (such as antibody or fragment thereof), denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

According to any one of the aspects and embodiments of the invention, when referring to antibody or fragment thereof, the terms "comprising the amino acid sequence set forth in SEQ ID NO: X", "comprising SEQ ID NO: X" and "having SEQ ID NO: X" are used herein interchangeably. The terms "consisting of the amino acid sequence set forth in SEQ ID NO: X", "consisting of SEQ ID NO: X" and "of SEQ ID NO: X" are used herein interchangeably.

The same rule holds for nucleic acid sequence. Thus, the terms "nucleic acid comprising the nucleic acid sequence set forth in SEQ ID NO: X", "nucleic acid comprising SEQ ID NO: X" and "nucleic acid having SEQ ID NO: X" are used herein interchangeably. The terms "nucleic acid consisting of the nucleic acid sequence set forth in SEQ ID NO: X", "nucleic acid consisting of SEQ ID NO: X" and "nucleic acid of SEQ ID NO: X" are used herein interchangeably.

The terms "comprising", "comprise(s)", "include(s)", "having", "has" and "contain(s)," are used herein interchangeably and have the meaning of "consisting at least in part of". When interpreting each statement in this specification that includes the term "comprising", features other than that or those prefaced by the term may also be present. Related terms such as "comprise" and "comprises" are to be interpreted in the same manner. The terms "have", "has", having" and "comprising" also encompass the meaning of "consisting of" and "consisting essentially of", and may be substituted by these terms. Thus, according to any aspect or embodiment of the present invention, the statement such as VH or VL comprising amino acid sequence X has also the meaning that the VH or VL consists of amino acid sequence X.

The term "conservative substitution" as used herein denotes the replacement of an amino acid residue by another, without altering the overall conformation and biological activity of the peptide, including, but not limited to, replacement of amino acid with one having similar properties (such as, for example, polarity, hydrogen bonding potential, acidic, basic, shape, hydrophobic, aromatic, and the like). Amino acids with similar properties are well known in the art. For example, according to one table known in the art, the following six groups each contain amino acids that are conservative substitutions for one another: (1) Alanine (A), Serine(S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W).

According to some embodiments, the present invention provides a monoclonal antibody (mAb) or a fragment thereof that specifically binds to SLeA, comprising a VH domain comprising amino acid SEQ ID NO: 17 and the VL comprising amino acid sequence SEQ ID NO: 18. In some embodiments and examples of the invention, such an antibody is referred to as Ablift15.

According to some embodiments, the present invention provides a monoclonal antibody (mAb) or a fragment thereof that specifically binds to SLeA, comprising a VH domain comprising amino acid SEQ ID NO: 19 and the VL comprising amino acid sequence SEQ ID NO: 20. In some embodiments and examples of the invention, such an antibody is referred to as Ablift2.

According to some embodiments, the present invention provides a monoclonal antibody (mAb) or a fragment thereof that specifically binds to SLeA, comprising a VH domain comprising amino acid SEQ ID NO: 17 and the VL comprising amino acid sequence SEQ ID NO: 20. According to some embodiments, the present invention provides a monoclonal antibody (mAb) or a fragment thereof that specifically binds to SLeA, comprising a VH domain comprising amino acid SEQ ID NO: 19 and the VL comprising amino acid sequence SEQ ID NO: 18. According to some embodiments, the present invention further provides a functional analog of said antibodies or fragment thereof comprising at least 90% sequence identity to said antibodies or fragment thereof, wherein no substitution is introduced into CDRs, into positions 99 and 100 of the sequence of the VH domain and into positions 43 and 87 of the VL domains. Thus, according to such embodiments, the analog does not comprise further substitutions in CDRs, in positions 99 and 100 of the sequence of the VH domain and in positions 43 and 87 of the VL domains. The terms "analog" and "functional analog" refer to such antibodies or fragments thereof which differ by one or more amino acid alterations (e.g., substitutions, additions or deletions of amino acid residues) from the original sequence. According to one embodiment, the analog has about 90% to about 99%, about 91% to about 98% or about 92% to about 96%, or about 93% to 95% sequence identity to the original peptide. According to some embodiments, the functional analog has 90, 91, 92, 93, 94, 95, 96, 97, 98, or 99% sequence identity to the original sequence.

According to some embodiments, the present invention provides a functional analog of the monoclonal antibody (mAb) or a fragment of the present invention, wherein the analog comprises a VH comprising an amino acid sequence having at least 90% sequence identity to amino acid SEQ ID NO: 17 and a VL comprising an amino acid sequence having at least 90% sequence identity to amino acid SEQ ID NO: 18, wherein no substitution is introduced into CDRs, into positions 99 and 100 of SEQ ID NO: 17 and into positions 43 and 87 of SEQ ID NO: 18. According to some embodiments, the present invention provides a functional analog of the monoclonal antibody (mAb) or a fragment of the present invention, wherein the analog comprises a VH comprising an amino acid sequence having at least 90% sequence identity to amino acid SEQ ID NO: 17 and a VL comprising an amino acid sequence having at least 90% sequence identity to amino acid SEQ ID NO: 19, wherein no substitution is introduced into CDRs, into positions 99 and 100 of SEQ ID NO: 20 and into positions 43 and 87 of SEQ ID NO: 20. According to some embodiments, no substitution is introduced into positions 35 of the VH sequence, e.g of SEQ ID NO: 17 or 19.

According to some embodiments, the present invention provides a fragment of the monoclonal antibody of the present invention. According to some embodiments, the fragment is a single chain variable fragment (scFv). According to some embodiments, the present invention provides a scFv comprising a VH comprising amino acid sequences SEQ ID NO: 17 and a VL comprising amino acid sequences SEQ ID NO: 18. According to some embodiments, the scFv is a functional analog of such scFv. According to some embodiments, the scFv comprises a VH comprising an amino acid sequence having at least 90% sequence identity to amino acid SEQ ID NO: 17 and a VL comprising an amino acid sequence having at least 90% sequence identity to amino acid SEQ ID NO: 18, wherein no substitution is introduced into CDRs, into positions 99 and 100 of SEQ ID NO: 17 and into positions 43 and 87 of SEQ ID NO: 18. According to some embodiments, the VH and VL are linked by a peptide linker. The terms "linker" or "spacer" relate to any peptide capable of connecting two domains of the scFv or two distinguishable sections of the scFv such as variable domains with its length depending on the kinds of variable domains to be connected. According to some embodiments, the linker comprises an amino acid sequence comprising from 1 to 10 repetitions of amino acid sequence SEQ ID NO: 68. According to some embodiment, the linker comprises 2, 3, or 4 repetitions of amino acid sequence SEQ ID NO: 68. According to some embodiments, the scFv comprises or consists of amino acid sequence SEQ ID NO: 21. According to another embodiment, the scFv is a functional analog having at least 90% sequence identity to amino acid SEQ ID NO: 21 and wherein no substitution is introduced into CDRs, into positions 99 and 100 of the amino acid sequence corresponding to SEQ ID NO: 17 and into positions 43 and 87 of the amino acid sequence corresponding to SEQ ID NO: 18.

According to some embodiments, the present invention provides a fragment of the monoclonal antibody of the present invention. According to some embodiments, the fragment is a single chain variable fragment (scFv). According to some embodiments, the present invention provides a scFv comprising a VH comprising amino acid sequences SEQ ID NO: 19 and a VL comprising amino acid sequences SEQ ID NO: 20. According to some embodiments, the scFv is a functional analog of such scFv. According to some embodiments, the scFv comprises a VH comprising an amino acid sequence having at least 90% sequence identity to amino acid SEQ ID NO: 19 and a VL comprising an amino acid sequence having at least 90% sequence identity to amino acid SEQ ID NO: 20, wherein no substitution is introduced into CDRs, into positions 99 and 100 of SEQ ID NO: 19 and into positions 43 and 87 of SEQ ID NO: 20. According to some embodiments, the VH and VL are linked by a peptide linker. According to some embodiments, the linker comprises an amino acid sequence comprising from 1 to 10 repetitions of amino acid sequence SEQ ID NO: 68. According to some embodiment, the linker comprises 2, 3, or 4 repetitions of amino acid sequence SEQ ID NO: 68. According to some embodiments, the scFv comprises or consists of amino acid sequence SEQ ID NO: 22. According to another embodiment, the scFv is a functional analog having at least 90% sequence identity to amino acid to SEQ ID NO: 22 and wherein no substitution is introduced into CDRs, into positions 99 and 100 of amino acid sequence corresponding to SEQ ID NO: 17 and into positions 43 and 87 of the amino acid sequence corresponding to SEQ ID NO: 18.

According to any one of the embodiments of the present invention, the isolated mAb or the fragment of the present invention exhibits an increased affinity to SLeA (CA19-9) as compared to the antibody comprising SEQ ID NOs: 1 and 2, as determined e.g. by surface plasmon resonance (SPR) or ELISA assay. According to some embodiments of the invention, the increased affinity is from 2 to 12, from 4 to 10, from 5 to 9 or from 6 to 8 fold higher than that of the wild type (WT) antibody or a fragment thereof. According to other embodiments of the invention, the antibody exhibits similar glycan binding specificity as that of WT antibody comprising SEQ ID NOs: 1 and 2. According to some embodiments, the isolated mAb or the fragment has KD from 1 to 30 nM.

According to any one of the above embodiments, the isolated mAb or the fragment of the present invention binds SLeA glycan with an equilibrium dissociation constant (KD) of about 0.01 to 100 nM. According to one embodiment, the mAb or the fragment of the present invention binds SLeA glycan with an equilibrium dissociation constant (KD) of about 0.05 to 80 nM, about 0.075 to 60 nM. According to one embodiment, the mAb or the fragment of the present invention binds SLeA glycan with an equilibrium dissociation constant (KD) of about 0.1 to 30 nM. According to some embodiment, the mAb or the fragment of the present invention binds SLeA glycan with an equilibrium dissociation constant (KD) of about 0.1 to 20 nM. According to one embodiment, the mAb or the fragment of the present invention binds SLeA glycan with an equilibrium dissociation constant (KD) of about 0.1 to 10 nM. According to some embodiments, the scFv of the present invention has KD of from 1 to 25 nM. According to some embodiments, the mAb of the present invention has KD of from 0.01 to 5 nM. According to some embodiments, the mAb of the present invention has KD of from 0.01 to 30 nM. According to some embodiments, the mAb of the present invention has KD of from 0.05 to 30 nM. According to some embodiments, the mAb of the present invention has KD of from 1 to 20 nM. According to some embodiments, the mAb of the present invention has KD of from 2 to 10 nM.

The term "$K_D$" and "apparent KD", as used herein, is intended to refer to the dissociation constant of a particular antibody-antigen interaction. KD is calculated by ka/kd. The term "kon" or "ka", as used herein, is intended to refer to the on rate constant for association of an antibody to the antigen to form the antibody/antigen complex. The term "koff" or "kd", as used herein, is intended to refer to the off rate constant for dissociation of an antibody from the antibody/antigen complex.

According to some embodiments, the inhibitions constant (Ki) of the isolated mAb of the present invention or of the fragment thereof is from 30 to 500 nM, from 40 to 300 nM, from 50 to 200 nM or from 50 to 150 nM.

According to some embodiments, the mAb or the fragment of the present invention is a chimeric antibody or fragment.

According to some embodiments, the isolated mAb the fragment thereof of the present invention is humanized mAb or fragment.

The term "humanized antibodies" refers to antibodies from non-human species (e.g. murine antibodies) which amino acid sequences have been modified to increase their similarity to antibody variants produced naturally in humans. The process of "humanization" is usually applied to monoclonal antibodies developed for administration to humans, and performed when the process of developing a specific antibody involves generation in a non-human immune system (such as in mice). The protein sequences of antibodies produced in this way are distinct from antibodies occurring naturally in humans, and are therefore immunogenic when administered to human patients. Humanized antibodies are considered distinct from chimeric antibodies, which have protein sequences similar to human antibodies, but carry large stretches of non-human protein. The humanized antibody optimally also will comprise at least a portion of an immunoglobulin constant region (Fc), typically that of a human immunoglobulin. Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain.

In the present invention, during the humanization, framework regions of the mouse antibody specific to SLeA glycan having improved affinity to the SLeA or its analog were mutated. This was done using rational consideration of each and every site using structural modeling and experimental information. Moreover, considering that the analog of mouse antibody already had some modifications in comparison to native antibodies, these modifications were kept in order to preserve activity. In addition, some amino acids that are close to CDRs were maintained as well.

According to some embodiments, the present invention provides an isolated humanized monoclonal antibody or a fragment thereof that specifically binds to SLeA of the mAb or the fragment of the present invention.

According to some embodiments, the present invention provides a humanized monoclonal antibody or the fragment thereof that specifically binds to SLeA, comprising a VH domain comprising an amino acid sequence selected from SEQ ID NO: 17 and SEQ ID NO: 1 and a VL domain comprising amino acid sequence SEQ ID NO:18, wherein 10 or more amino acid residues in the framework regions in both VH and in VL are further substituted and wherein the substituted amino acids are not at positions 99 and 100 of the VH and not at positions 43 and 87 of the VL.

According to some embodiments, the present invention provides an isolated humanized monoclonal antibody or the fragment thereof that specifically binds to SLeA, comprising a VH domain comprising an amino acid sequence SEQ ID NO: 17 and a VL domain comprising an amino acid sequence SEQ ID NO:18, wherein 10 to 26 amino acid residues in the framework regions of VH and of VL are further substituted and wherein the substituted amino acids are not at positions 99 and 100 of the VH and not at positions 43 and 87 of the VL.

According to some embodiments, the present invention provides an isolated humanized monoclonal antibody or the fragment thereof that specifically binds to SLeA, comprising a VH domain comprising an amino acid sequence SEQ ID NO: 1 and a VL domain comprising an amino acid sequence SEQ ID NO:18, wherein 10 to 26 amino acid residues in the framework regions in VH and in VL are further substituted and wherein the substituted amino acids are not at positions 99 and 100 of the VH and not at positions 43 and 87 of the VL.

According to some embodiments, the VH comprises amino acid sequence SEQ ID NO: 17 in which from 11 to 24, from 12 to 22, from 13 to 20, from 14 to 18 or from 15 to 18 of amino acid residues in the framework regions are substituted. According to some embodiments, the VH comprises amino acid sequence SEQ ID NO: 17 in which from 11 to 24, from 12 to 22, from 13 to 20, from 14 to 18 or from 15 to 18 of amino acid residues in the framework regions are substituted. According to some embodiments, the VL comprises amino acid sequence SEQ ID NO: 18 in which from 11 to 24, from 12 to 22, from 13 to 20 or from 14 to 18 of amino acid residues in the framework regions are substituted.

According to some embodiments, the VH comprises amino acid sequence SEQ ID NO: 17 in which from 11 to 24, from 12 to 22, from 13 to 20, from 14 to 18 or from 15 to 18 of amino acid residues in the framework regions are substituted and the VL comprises amino acid sequence SEQ ID NO: 18 in which from 11 to 24, from 12 to 22, from 13 to 20 or from 14 to 18 of amino acid residues in the framework regions are substituted.

According to some embodiments, substitutions in the framework regions of VH domain are at 10 positions or more of positions 3, 5, 18, 19, 40, 42, 72, 79, 80, 81, 89, 90, 94, 95, 110, 114, 115 of SEQ ID NO: 17. According to some embodiments, substitutions in the framework regions of VH domain are at 11, 12, 13, 14, 15, 16 or 17 positions of positions 3, 5, 18, 19, 40, 42, 72, 79, 80, 81, 89, 90, 94, 95, 110, 114, 115 of SEQ ID NO: 17. According to other embodiments, substitutions in the framework regions of VL domain are at 10 positions or more of positions 3, 11, 12, 15, 17, 22, 46, 69, 71, 72, 73, 79, 80, 83, 84, 85, and 104 of SEQ ID NO: 18. According to some embodiments, substitutions in the framework regions of VL domain are at 11, 12, 13, 14, 15, 16, 17 or 18 positions of positions 3, 11, 12, 15, 17, 22, 46, 69, 71, 72, 73, 79, 80, 83, 84, 85, and 104 of SEQ ID NO: 18. According to some embodiments, substitutions in the framework regions of VH domain are at 14, 15, 16 or 17 positions of positions 3, 5, 18, 19, 40, 42, 72, 79, 80, 81, 89, 90, 94, 95, 110, 114, and 115 of SEQ ID NO: 17 and substitutions in the framework regions of VL domain are at 14, 15, 16, 17 or 18 positions of positions 3, 11, 12, 15, 17, 22, 46, 69, 71, 72, 73, 79, 80, 83, 84, 85, and 104 of SEQ ID NO: 18.

According to some embodiments, the present invention provides an isolated humanized monoclonal antibody or the fragment thereof that specifically binds to SLeA, comprising a VH domain comprising an amino acid sequence selected from SEQ ID NO: 19 and a VL domain comprising an amino acid sequence SEQ ID NO:20, wherein 10 to 26 amino acid residues in the framework regions in VH and in VL are further substituted and wherein the substituted amino acids are not at positions 99 and 100 of the VH and not at positions 43 and 87 of the VL. According to some embodiments, the substitution is the FR domains as defined in the above embodiments.

According to some embodiments, the VH of the humanized mAb or the fragment comprises amino acid sequence SEQ ID NO: 23. According to other embodiments, the VH of the humanized mAb or the fragment comprises amino acid sequence SEQ ID NO: 25. According to one embodiment, the VL of the humanized mAb or the fragment comprises amino acid sequence SEQ ID NO: 24.

According to some embodiments, the present invention provides a humanized monoclonal antibody or the fragment thereof that specifically binds to SLeA, comprising a VH domain comprising or consisting of amino acid sequence SEQ ID NO: 23 and a VL domain comprising or consisting of amino acid sequence SEQ ID NO: 24.

According to some embodiments, the present invention provides a humanized monoclonal antibody or the fragment thereof that specifically binds to SLeA, comprising a VH domain comprising or consisting of amino acid sequence SEQ ID NO: 25 and a VL domain comprising or consisting of amino acid sequence SEQ ID NO: 24.

According to some embodiments, the fragment of the humanized monoclonal antibody is scFv. According to some embodiments, the VH and VL domains are linked by a peptide linker as described in the above embodiments, e.g. by a plurality of copies of amino acid sequence SEQ ID NOL 68. According to some embodiments, the present invention provides an scFv comprising or consisting of amino acid sequence SEQ ID NO: 26. According to some embodiments, the present invention provides an scFv comprising or consisting of amino acid sequence SEQ ID NO: 27.

According to some embodiments, the humanized mAb or a fragment thereof has a similar affinity of SLeA as the mouse Ab from which they derive. According to some embodiments, the humanized mAb or a fragment thereof has an increased affinity of SLeA in comparison to the mouse Ab from which they derive. According to some embodiments, the humanized mAb or a fragment thereof has KD of from 1 to 120 nm. According to some embodiments, the humanized mAb or a fragment thereof has KD of from 1 to 80 nm. According to some embodiments, the humanized mAb or a fragment thereof has KD of from 1 to 30 nm. According to some embodiments, the humanized mAb or a fragment thereof has KD of from 3 to 10 nm. According to some embodiments, the humanized mAb or a fragment thereof has KD of from 50 to 120 nm. According to some embodiments, the humanized mAb or a fragment thereof has KD of from 50 to 90 nm.

According to some embodiments, the humanized mAb or a fragment thereof comprising a VH domain comprising or consisting of amino acid sequence SEQ ID NO: 23 and a VL domain comprising or consisting of amino acid sequence SEQ ID NO: 24 has KD of from 1 to 20 to SLeA. According to some embodiments, the humanized mAb or a fragment thereof comprising a VH domain comprising or consisting of amino acid sequence SEQ ID NO: 25 and a VL domain comprising or consisting of amino acid sequence SEQ ID NO: 24 has KD of from 50 to 90 to SLeA.

According to some embodiments, the humanized antibody or fragment thereof of the present invention has from 20 to 90% lower immunogenicity as compared to the original mouse Ab, as tested according to the teaching of the present invention. As shown in the Examples, the immunogenicity of scFv-HuAblift15-VI is about 69% of scFv-mNative, and that of scFv-HuAblift15-V2 is about 77% of scFv-mNative; scFv-HuAblift15-V1 is about 43% of scFv-mAblift15, and scFv-HuAblift15-V2 is about 58% of scFv-mAblift15. Thus according to some embodiments, the immunogenicity of the humanized antibody or fragment thereof is from 30 to 70% lower than that of the original mouse antibody. According to some embodiments, the immunogenicity of the humanized antibody or fragment thereof is from 1.5 to 5, from 1.7 to 3 lower than the original mAb, e.g. mutant mAb. Immunogenicity of humanized antibody clones can be evaluated by analysis of scFv recognition by pooled human IgG obtained from thousands of human donors (IVIg; Gamma Gard). For this purpose, IVIg was first pre-cleared from anti-yeast reactivity by serial incubations with yeast cells, then binding to scFv-expressing yeast cells was examined by FACS. Expression of scFv on yeast can be examined by mouse-anti-c-Myc and pooled human IgG binding detected with anti-human IgG, and double positive labeling of scFv-expressing yeast cells was examined. The ratio of positive/negative IVIg labeling indicate that that IVIg had reduced binding to scFv. According to some embodiments, the humanized antibody or fragment thereof of the present invention has from 40 to 90% lower immunogenicity as compared to the original mouse Ab. According to some embodiments, the humanized antibody or fragment thereof of the present invention has from 60 to 90% lower immunogenicity as compared to the original mouse Ab. According to some embodiments, the humanized antibody or fragment thereof of the present invention has from 70 to 90% lower immunogenicity as compared to the original mouse Ab.

According to any one of the above embodiments, the heavy chain constant region of the mAb or the fragment is selected from the group consisting of: human IgG1, human IgG2, human, IgG3, human IgG4, mouse IgG1, mouse IgG2a, mouse IgG2b, mouse IgG3. According to some embodiments, the light chain constant region is selected from kappa and lambda.

According to some embodiments, the isolated monoclonal antibody or a fragment thereof or of the humanized isolated monoclonal antibody or a fragment thereof of the present invention exhibits the same glycan binding specificity as that of WT antibody comprising SEQ ID NOs: 1 and 2. According to some embodiments, the isolated monoclonal antibodies, the humanized isolated monoclonal antibody or a fragment thereof exhibits cell killing activity of CA19-9+ malignancies.

According to any one of the above embodiments, the mAb or the fragments thereof, or the humanized mAb or the fragment thereof is for use in treating cancer overexpressing SLeA carbohydrate. The term "CA19-9+ malignancies" and "cancer overexpressing SLeA carbohydrate" may be used interchangeably. According to one embodiment, the cancer is selected from pancreatic, hematological, breast, ovarian, colorectal, stomach, head and neck, liver, lung, oropharyngeal cancer, squamous cell carcinoma and gallbladder cancer. According to some embodiments, the mAb or the fragments thereof, or the humanized mAb or the fragment thereof is for use in diagnostic of the cancer is a subject.

For ease the reading of the application, in some embodiments, the terms monoclonal antibodies and fragments thereof encompass also humanized monoclonal antibodies and fragments thereof.

According to another aspect, the present invention provides a conjugate of the isolated monoclonal antibody or a fragment thereof or the isolated humanized monoclonal antibody or a fragment thereof. All embodiments and definitions used in any one of the above aspects and embodiments apply and are encompassed herein as well.

The term "conjugate" as used herein refers to the association of an antibody or a fragment thereof with another moiety. According to some embodiments, the moiety is a tag or label and the conjugate comprises a label. The terms "tag" or "label" refer to a moiety which is attached, conjugated, linked or bound to, or associated with a compound such as an antibody or antibody fragment of the present invention and which may be used as a means of, for example, identifying, detecting and/or purifying the compound. Tags or labels include haemagglutinin tag, myc tag, poly-histidine tag, protein A, glutathione S transferase, Glu-Glu affinity tag, substance P, FLAG peptide, biotin and streptavidin binding peptide, enzyme, GFP, and rodamine. According to some embodiments, the label is a fluorescent label.

The term "moiety" as used herein refers to a part of a molecule, which lacks one or more atom(s) compared to the corresponding molecule. The term "moiety", as used herein, further relates to a part of a molecule that may include either whole functional groups or parts of functional groups as substructures.

According to some embodiments, the moiety is an active moiety. The term "active agent" and "active moiety" are used herein interchangeably and refer to an agent that has biological activity, pharmacologic effects and/or therapeutic utility.

According to some embodiments, the active moiety is an anti-cancer active moiety. According to some embodiments, the active moiety is an anti-cancer moiety. The term "anti-cancer", "anti-neoplastic" and "anti-tumor" when referred to a compound, an agent or a moiety are used herein interchangeably and refer to a compound, drug, antagonist, inhibitor, or modulator such as immunomodulatory having anticancer properties or the ability to inhibit or prevent the growth, function or proliferation of and/or causing destruction of cells," and in particular tumor cells. Therapeutic agents suitable in an anti-neoplastic composition for treating cancer include, but not limited to, chemotherapeutic agents, radioactive isotopes, toxins, cytokines such as interferons, immunostimulating agents, immunomodulating agents and antagonistic agents targeting cytokines, cytokine receptors or antigens associated with tumor cells. In some embodiments, an anti-cancer agent is a chemotherapeutic. Thus according to some embodiments, the present invention provides a conjugate of the mAb (including humanized mAb) of the present invention or of a fragment thereof and an anti-cancer moiety such as chemotherapeutic agents, radioactive isotopes, toxins, cytokines such as interferons, immunostimulating agents, immunomodulating agents and antagonistic agents targeting cytokines, cytokine receptors or antigens associated with tumor cells. According to another embodiment, the present invention provides a conjugate of the fragment of the mAb of the present invention and the anti-cancer moiety. According to any one of the above embodiments, the antibodies or the fragments thereof are isolated.

According to some embodiments, the present invention provides a conjugate of an isolated mAb or a fragment thereof that specifically binds to SLeA, wherein the mAb or the fragment comprises an antigen binding domain comprising a VH domain and a VL domain each comprising three CDRs and four FR domains, wherein the VH-CDR 1 and 2 comprise amino acid sequences SEQ ID NOs: 3 and 4, respectively, VH-CDR 3 comprises an amino acid sequence selected from SEQ ID NO: 5 and 9; VL-CDRs 1 and 3 comprise amino acid sequences SEQ ID NOs: 6 and 12, respectively; and VL-CDR 2 comprises an amino acid sequence selected from SEQ ID NO: 10 and SEQ ID NO: 11. According to some embodiments, the present invention provides a conjugate of a monoclonal antibody (mAb) or a fragment thereof that specifically binds to SLeA, comprising a VH domain comprising amino acid SEQ ID NO: 17 and the VL comprising amino acid sequence SEQ ID NO: 18. According to some embodiments, the present invention provides a conjugate of a monoclonal antibody (mAb) or a fragment thereof that specifically binds to SLeA, comprising a VH domain comprising amino acid SEQ ID NO: 19 and the VL comprising amino acid sequence SEQ ID NO: 20. According to some embodiments, the present invention provides a conjugate of a functional analog of said mAbs. According to some embodiments, the present invention provides a conjugate of the fragment of said mAbs. According to some embodiments, the present invention provides a conjugate of scFv comprising or consisting of SEQ ID NO: 21. According to some embodiments, the present invention provides a conjugate of scFv comprising or consisting of SEQ ID NO 22. According to some embodiments, the present invention provides a conjugate of a functional analog of said scFv as defined above. According to some embodiments, the present invention provides a conjugate of a humanized isolated monoclonal antibody or a fragment thereof of the above-defined Ab or fragments thereof. According to some embodiments, the present invention provides a conjugate of a humanized monoclonal antibody or the fragment thereof that specifically binds to SLeA, comprising a VH domain comprising or consisting of an amino acid sequence selected from SEQ ID NO: 23 and 25, and a VL domain comprising or consisting of amino acid sequence SEQ ID NO: 24. According to some embodiments, the present invention provides a conjugate of a humanized scFv comprising or consisting of an amino acid sequence selected from SEQ ID NO: 26 and 27. According to some embodiments, the conjugate comprises an anti-cancer moiety. According to other embodiments, the conjugate comprises a tag or a label. The conjugates of the present invention may be used for diagnosis and treatment.

According to some embodiments, the isolated monoclonal antibody, the humanized isolated monoclonal antibody or a fragment thereof, or the conjugate thereof is immobilized to a solid support. According to some embodiments, the humanized isolated monoclonal antibody or a fragment thereof or the conjugate thereof is attached to a detectable moiety.

According to another aspect, the present invention provides a chimeric antigen receptor (CAR) comprising the mAb or the fragment of the present invention or the humanized mAb or fragment thereof of the present invention. All embodiments and definitions used in any one of the above aspects and embodiments apply and are encompassed herein as well.

The terms "chimeric antigen receptor" or "CAR" are used herein interchangeably and refer to engineered recombinant polypeptide or receptor which are grafted onto cells and comprises at least (1) an extracellular domain comprising an antigen-binding region, e.g., a single chain variable fragment of an antibody or a whole antibody, (2) a transmembrane domain to anchor the CAR into a cell, and (3) one or more cytoplasmic signaling domains (also referred to herein as "an intracellular signaling domains"). The extracellular domain comprises an antigen binding domain (ABD) and optionally a spacer or hinge region. The antigen binding domain of the CAR targets a specific antigen. The targeting regions may comprise full length heavy chain, Fab fragments, or single chain variable fragment (scFvs).

The terms "antigen binding portion", "antigen binding domain" and "ABD" refer to one or more fragments of an antibody that retain the ability to specifically bind to an antigen. It has been shown that the antigen binding function of an antibody can be performed by fragments of a full-length antibody. Such ABD may also be bispecific, dual specific, or multi-specific formats; specifically binding to two or more different antigens. Examples of binding fragments encompassed within the term "antigen binding portion" include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb, which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). Such single chain antibodies are also intended to be encompassed within the term "antigen binding portion". In certain embodiments of the invention, scFv molecules are incorporated into a fusion protein. Other forms of single chain antibodies, such as diabodies are also encompassed. The antigen binding domain can be derived from the same species or a different species for or in which the CAR will be used. In one embodiment, the antigen binding domain is a scFv.

The term "transmembrane domain" refers to the region of the CAR, which crosses or bridges the plasma membrane. The transmembrane domain of the CAR of the invention is the transmembrane region of a transmembrane protein, an artificial hydrophobic sequence or a combination thereof. According to some embodiments, the term comprises also the transmembrane domain together with extracellular spacer or hinge region.

The term "intracellular domain" refers to the intracellular part of the CAR and may be an intracellular domain of T cell receptor or of any other receptor (e.g., TNFR superfamily member) or portion thereof, such as an intracellular activation domain (e.g., an immunoreceptor tyrosine-based activation motif (ITAM)-containing T cell activating motif), an intracellular costimulatory domain, or both.

According to some embodiments, the present invention provides a CAR comprising an antigen binding domain comprising VH and VL domains each comprising three CDRs and four FRs, wherein the VH-CDR 1 and 2 comprise amino acid sequences SEQ ID NOs: 3 and 4, respectively, VH-CDR 3 comprises an amino acid sequence selected from SEQ ID NO: 5 and 9; VL-CDRs 1 and 3 comprise amino acid sequences SEQ ID NOs: 6 and 12, respectively; and VL-CDR 2 comprises an amino acid sequence selected from SEQ ID NO: 10 and SEQ ID NO: 11. According to some embodiments, the present invention provides a CAR comprising an antigen binding domain comprising a VH domain comprising amino acid SEQ ID NO: 17 and the VL comprising amino acid sequence SEQ ID NO: 18. According to some embodiments, the present invention provides a CAR comprising an antigen binding domain comprising a VH domain comprising amino acid SEQ ID NO: 19 and the VL comprising amino acid sequence SEQ ID NO: 20. According to some embodiments, the CAR comprises an scFv of the present invention. According to some embodiments, the scFv comprises a VH domain comprising amino acid SEQ ID NO: 17 and the VL comprising amino acid sequence SEQ ID NO: 18. According to some embodiments, the scFv comprises a VH domain comprising amino acid SEQ ID NO: 19 and the VL comprising amino acid sequence SEQ ID NO: 20. According to some embodiments, the scFv comprises or consists of SEQ ID NO: 21. According to some embodiments, the scFv comprises or consists of SEQ ID NO 22. According to some embodiments, scFv is a functional analog of said scFv, as defined above. According to some embodiments, the present invention provides a CAR comprising an antigen binding domain comprising the humanized mAb of the present invention of a fragment thereof. According to some embodiments, the present invention provides a CAR comprising an antigen binding domain comprising a VH domain comprising or consisting of an amino acid sequence selected from SEQ ID NO: 23 and 25, and a VL domain comprising or consisting of amino acid sequence SEQ ID NO: 24. According to some embodiments, the present invention provides a CAR comprising a humanized scFv comprising or consisting of an amino acid sequence selected from SEQ ID NO: 26 and 27.

According to some embodiments, the CAR comprising humanized antigen binding domain has lower immunogenicity than the CAR comprising mouse antigen binding domain.

According to any one of the above embodiments, the CAR of the present invention comprises a transmembrane domain (TM domain), one or more costimulatory domains and an activation domain.

In one embodiment of the invention, the CAR includes a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154 or an analog thereof. According to one embodiment, the TM domain is a TM domain of a receptor selected from CD28 and CD8, or an analog thereof having at least 85% amino acid identity to the original sequence.

In some embodiments of the invention, the CAR comprises a costimulatory domain, e.g., a costimulatory domain comprising a functional signaling domain of a protein selected from the group consisting of OX40, CD2, CD27, CD28, CD5, ICAM-1, LFA-1 (CD11a/CD18), ICOS (CD278), 4-1BB (CD137), an analog thereof and a combination thereof. According to one embodiment, the costimulatory domain is selected from a costimulatory domain of a protein selected from CD28, 4-1BB, OX40, a functional analog thereof having at least 85% amino acid identity to the original sequence, and any combination thereof. According to some embodiments, the CAR of the present invention comprises two or more costimulatory domains. According to one embodiment, the CAR comprises costimulatory domains of CD28 and 4-1BB.

According to one embodiment, the TM domain and the costimulatory domain of the CAR are both derived from CD28.

According to some embodiments, the antigen binding domain is linked to the TM domain via a spacer.

According to any one of the above embodiments, the CAR comprises an activation domain. According to some embodiments, the activation domain is selected from FcRγ (gamma) and CD3-¿ (CD3-zetta) activation domains, or any other sequence that contains an intracellular tyrosine activating motif (ITAM). Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS") and CD66d. According to one embodiment, the activation domain is FcRγ domain.

According to some embodiments, the CAR of the present invention comprises a scFv according to any one of the above embodiments, a TM domain of a receptor selected from CD28 and CD8, a costimulatory domain selected from the domain of CD28, 4-1BB, OX40 and a combination thereof, and an activation domain is selected from FcRγ and CD3-activation domains. According to some embodiments, the CAR of the present invention comprises a scFv having an amino acid sequence selected from SEQ ID NO: 21 and 22, a TM domain of a receptor selected from CD28 and CD8, a costimulatory domain selected from the domain of CD28, 4-1BB, OX40 and a combination thereof, and an activation domain is selected from FcRγ and CD3-ζ activation domains. According to some embodiments, the CAR of the present invention comprises a scFv having an amino acid sequence selected from SEQ ID NO: 26 and 27, a TM domain of a receptor selected from CD28 and CD8, a costimulatory domain selected from the domain of CD28, 4-1BB, OX40 and a combination thereof, and an activation domain is selected from FcRγ and CD3-ζ activation domains.

The term "CD28" refers to cluster of differentiation 28 protein. In some embodiments, the CD28 is a human CD28. The term "CD8" refers to cluster of differentiation 8 protein being a transmembrane glycoprotein and serving as a co-receptor for the T cell receptor. According to one embodiment, the CD8 is a human CD8. The terms "ICOS" and "Inducible T-cell COStimulator" refer to CD278 which is a CD28-superfamily costimulatory molecule. According to one embodiment, the ICOS is a human ICOS. The term "4-1BB" refers to a CD137 protein which is a member of the tumor necrosis factor receptor family and has costimulatory activity for activated T cells. According to one embodiment, 4-1BB is a human 4-1BB. The terms "CD3ζ" and "CD3-zetta" refer to a ζ (zetta) chain of CD3 (cluster of differentiation 3) T cell co-receptor participating in activation of both the cytotoxic and helper T cells. According to one embodiment, CD3ζ comprises an immunoreceptor tyrosine-based activation motif (ITAM). According to one embodiment, the CD3ζ is human CD3ζ. CD3ζ is sometimes also referred as CD247. The term "FcRγ" refers to Fc gamma receptors, which generate signals within their cells through ITAM. These are immunoglobulin superfamily receptors that are found on various innate as well as adoptive immune cells, where the extracellular part binds IgGs the activation signal is transduced through two ITAMs located on its cytoplasmic tail.

According to any one of the above embodiments, the CAR further comprises a leading peptide. According to one embodiment, the leading peptide is located N-terminally to the ABD. The terms "leader peptide", "leading peptide", "lead peptide", "signaling peptide" and "signal peptide" are used herein interchangeable and refer to a peptide that translocates or prompts translocation of the target protein to cellular membrane.

According to any one of the above embodiments, the CAR of the present invention further comprises a tag sequence. According to some embodiments, the tag is selected haemagglutinin tag, myc tag, poly-histidine tag, protein A, glutathione S transferase, Glu-Glu affinity tag, substance P, FLAG peptide, streptavidin (strep) binding peptide and human FC tag. According to some embodiments, the tags is a strep-tag.

According to any one of the above embodiments, the CAR of the present invention is for use in treating cancer. According to any one of the above embodiments, the cancer is a cancer overexpressing SLeA glycan. According to one embodiment, the cancer is selected from hematological, breast, ovarian, pancreatic, colorectal, stomach, head and neck, liver, lung, oropharyngeal cancer, squamous cell carcinoma and gallbladder cancer. According to one embodiment, the cancer is pancreatic cancer. According to one embodiment, the cancer is a breast cancer.

According to yet another aspect, the present invention provides a nucleic acid molecule encoding at least one chain of a monoclonal antibody or fragment thereof, at least one chain of the humanized monoclonal antibody or a fragment thereof or the CAR of the present invention. According to some embodiments, the nucleic acid molecule encodes at least one amino acid comprising or consisting of an amino acid sequence selected from SEQ ID NOs: 17-27. According to some embodiments, the nucleic acid comprises or consists of at least one nucleic acid comprising a nucleic acid sequence selected from SEQ ID NOs: 30-39. According to some embodiments, the present invention provides a conservative variant of said nucleic acid.

The term "nucleic acid molecule" refers to a single stranded or double stranded sequence (polymer) of deoxyribonucleotides or ribonucleotides. The terms "nucleic acid" and "polynucleotide" are used herein interchangeably. According to some embodiments, the nucleic acid molecule is an isolated nucleic acid molecule. The term "isolated nucleic acid" as used herein denotes that the nucleic acid is essentially free of other cellular components with which it is associated in the cell. It can be, for example, a homogeneous state and may be dry or in the state of a solution, such as aqueous solution. Purity and homogeneity are typically determined using analytical chemistry techniques such as polyacrylamide gel electrophoresis or high performance liquid chromatography. The term "encoding" refers to the ability of a nucleotide sequence to code for one or more amino acids. The term does not require a start or stop codon. An amino acid sequence can be encoded in any one of six different reading frames provided by a polynucleotide sequence and its complement.

The terms "homolog" "variant", "DNA variant", "sequence variant" and "polynucleotide variant" are used herein interchangeably and refer to a DNA polynucleotide having at least 70% sequence identity to the parent polynucleotide. The variant may include mutations such as deletion, addition or substitution such that the mutations do not change the open reading frame and the polynucleotide encodes a peptide or a protein having substantially similar structure and function as a peptide or a protein encoded by the parent polynucleotide. According to some embodiments, the variants are conservative variants. The term "conservative variants" as used herein refers to variants in which a change of one or more nucleotides in a given codon position results in no alteration in the amino acid encoded at that position. Thus, the peptide or the protein encoded by the conservative variants has 100% sequence identity to the peptide or the protein encoded by the parent polynucleotide. According to some embodiments, the variant is a non-conservative variant encoding to a peptide or a protein being a conservative analog of the peptide of the protein encoded by the parent polynucleotide. According to some embodiments, the variant has at least 75%, at least 80% at least 85%, at least 90%, at least 95%, at least 98% or at least 99% sequence identity to the original nucleic acid sequence. According to one embodiment, the variant is a conservative variant. According to one embodiment, the variant is a conservative variant having at least 90% sequence identity to the original sequence.

According to another aspect, the present invention provides a nucleic acid construct comprising the nucleic acid of the present invention, operably linked to a promoter. According to some embodiments, the nucleic acid comprises or consists of one or more nucleic acid sequences selected from SEQ ID NOs: 30-39.

The terms "operably linked", "operatively linked", "operably encodes", "operably bound" and "operably associated" are used herein interchangeably and refer to the functional linkage between a promoter and nucleic acid sequence, wherein the promoter initiates transcription of RNA corresponding to the DNA sequence. A heterologous DNA sequence is "operatively associated" with the promoter in a cell when RNA polymerase which binds the promoter sequence transcribes the coding sequence into mRNA which then, in turn, is translated into the protein encoded by the coding sequence.

The term "promoter" as used herein refers to a regulatory sequence that initiates transcription of a downstream nucleic acid. The term "promoter" refers to a DNA sequence within a larger DNA sequence defining a site to which RNA polymerase may bind and initiate transcription. A promoter may include optional distal enhancer or repressor elements. The promoter may be either homologous, i.e., occurring naturally to direct the expression of the desired nucleic acid, or heterologous, i.e., occurring naturally to direct the expression of a nucleic acid derived from a gene other than the desired nucleic acid. A promoter may be constitutive or inducible. A constitutive promoter is a promoter that is active under most environmental and developmental conditions. An inducible promoter is a promoter that is active under environmental or developmental regulation, e.g., upregulation in response to xylose availability.

According to another aspect, the present invention provides a vector comprising the nucleic acid molecule or nucleic acid construct of the present invention. According to some embodiments, the nucleic acid or construct comprises or consists of a nucleic acid sequence selected from SEQ ID NOs: 30-39. The terms "vector" and "expression vector" are used herein interchangeably and refer to any viral or non-viral vector such as plasmid, virus, retrovirus, bacteriophage, cosmid, artificial chromosome (bacterial or yeast), phage, binary vector in double or single stranded linear or circular form, or nucleic acid, the sequence which is able to transform host cells and optionally capable of replicating in a host cell. The vector may be integrated into the cellular genome or may exist extra-chromosomally (e.g., autonomous replicating plasmid with an origin of replication). The vector may contain an optional marker suitable for use in the identification of transformed cells, e.g., tetracycline resistance or ampicillin resistance. A cloning vector may or may not possess the features necessary for it to operate as an expression vector. Any vector known in the art is envisioned for use in the practice of this invention. According to other embodiments, the vector is a virus, e.g. a modified or engineered virus. The modification of a vector may include mutations, such as deletion or insertion mutation, gene deletion or gene inclusion. In particular, a mutation may be done in one or more regions of the viral genome. Such mutations may be introduced in a region related to internal structural proteins, replication, or reverse transcription function. Other examples of vector modification are deletion of certain genes constituting the native infectious vector such as genes related to the virus' pathogenicity and/or to its ability to replicate. Any virus can be attenuated by the methods disclosed herein. According to some embodiments, the vector is a virus selected from lentivirus, adenovirus, modified adenovirus and retrovirus. In one particular embodiment, the vector is lentivirus. According to other embodiments, the vector is a plasmid.

According to another aspect, the present invention provides a cell comprising the monoclonal antibody or the fragment thereof, the humanized monoclonal antibody or the antibody fragment thereof, the CAR, the nucleic acid molecule, the nucleic acid construct or the vector of the present invention. According to some embodiments, the cell comprises the monoclonal antibody of the present invention. According to one embodiment, the cell comprises a fragment of the monoclonal antibody of the present invention. According to some embodiments, the cell comprises the humanized monoclonal antibody of the present invention. According to one embodiment, the cell comprises a fragment of the humanized monoclonal antibody of the present invention. According to other embodiments, the cell comprises, expresses or is capable of expressing the CAR or the present invention. According to yet another embodiment, the cell comprises the nucleic acid molecule, the nucleic acid construct or the vector of the present invention encoding the humanized monoclonal antibody or the antibody fragment thereof or the CAR of the present invention. According to some embodiments, the cell is capable of expressing the mAb, the humanized mAb, the fragment thereof, of the CAR of the present invention. According to some embodiments, a plurality of cells such as cell culture is encompassed.

According to some embodiments, the cell is selected from a bacterial, fungi such as yeast and mammalian cell. According to some embodiments, the cell is a mammalian cell. According to another embodiment, the cell is human. According to some embodiments, the cell is a leukocyte. According to some embodiments, the cell is selected from T cell and a natural killer (NK) cell. According to some embodiments, the present invention provides a T-cell genetically modified to express the CAR of the present invention.

According to some embodiment, the cells are T cells. Thus, according to some embodiments, the present invention provides T-cells comprising the CAR of the present invention. According to some embodiments, the T-cells comprise a CAR comprising the humanized mAb or the fragment thereof as described in any one of the above aspects and embodiments. All embodiments and definitions used in any one of the above aspects apply and are encompassed herein as well.

According to some embodiments, the present invention provides a cell comprising a mAb or a fragment thereof comprising a VH and VL domains each comprising three CDRs and four FRs, wherein the VH-CDR 1 and 2 comprise amino acid sequences SEQ ID NOs: 3 and 4, respectively, VH-CDR 3 comprises an amino acid sequence selected from SEQ ID NO: 5 and 9; VL-CDRs 1 and 3 comprise amino acid sequences SEQ ID NOs: 6 and 12, respectively; and VL-CDR 2 comprises an amino acid sequence selected from SEQ ID NO: 10 and SEQ ID NO: 11. According to some embodiments, the cell comprises a mAbs or fragment thereof, such as scFv, comprising a VH domain comprising amino acid SEQ ID NO: 17 and the VL comprising amino acid sequence SEQ ID NO: 18. According to some embodiments, the cell comprises a mAb or fragment thereof, such as scFv, comprising VH domain comprising amino acid SEQ ID NO: 19 and the VL comprising amino acid sequence SEQ ID NO: 20. According to some embodiments, the scFv comprises or consists of SEQ ID NO: 21 or SEQ ID NO 22. According to some embodiments, the scFv is a functional analog of said scFv, as defined above. According to some embodiments, the cell comprises a mAb or fragment thereof, such as scFv, comprising a VH domain comprising or consisting of an amino acid sequence selected from SEQ ID NO: 23 and 25, and a VL domain comprising or consisting of amino acid sequence SEQ ID NO: 24. According to some embodiments, the cell comprises humanized scFv comprising or consisting of an amino acid sequence selected from SEQ ID NO: 26 and 27. According to some embodiments, the cells are T cells. According to some embodiments, the T-cells are selected from memory, regulatory, helper or natural killer T-cells. According to some embodiments, the T cell is selected are from CD4+ T-cell and a CD8+ T-cell. According to some embodiments, the T cell are CD4+ T-cell and a CD8+ T-cell. According to some embodiments, the cells are NK cells. According to some embodiments, the cells are NK T-cells.

According to some embodiments, the present invention provides a cell comprising a CAR comprising VH and VL domains each comprising three CDRs and four FRs, wherein the VH-CDR 1 and 2 comprise amino acid sequences SEQ ID NOs: 3 and 4, respectively, VH-CDR 3 comprises an amino acid sequence selected from SEQ ID NO: 5 and 9; VL-CDRs 1 and 3 comprise amino acid sequences SEQ ID NOs: 6 and 12, respectively; and VL-CDR 2 comprises an amino acid sequence selected from SEQ ID NO: 10 and SEQ ID NO: 11. According to some embodiments, the cell comprises a mAbs or fragment thereof, such as scFv, comprising a VH domain comprising amino acid SEQ ID NO: 17 and the VL comprising amino acid sequence SEQ ID NO: 18. According to some embodiments, the cell comprises a CAR comprising VH domain comprising amino acid SEQ ID NO: 19 and the VL comprising amino acid sequence SEQ ID NO: 20. According to some embodiments, the present invention provides a cell comprising a CAR comprising an antigen binding domain comprising or consisting of SEQ ID NO: 21 or SEQ ID NO 22. According to some embodiments, the present invention provides a cell comprising a CAR comprising a VH domain comprising or consisting of amino acid sequence selected from SEQ ID NO: 23 and 25, and a VL domain comprising or consisting of amino acid sequence SEQ ID NO: 24. According to some embodiments, the present invention provides a cell comprising a CAR comprising an antigen binding domain comprising or consisting of amino acid sequence selected from SEQ ID NO: 26 and 27. According to some embodiments, the cells are T cells. According to some embodiments, the T-cells are selected from memory, regulatory, helper or natural killer T-cells. According to some embodiments, the T cell is selected are from CD4+ T-cell and a CD8+ T-cell. According to some embodiments, the T cell are CD4+ T-cell and a CD8+ T-cell. According to some embodiments, the cells are NK cells. According to some embodiments, the cells are NK T-cells.

According to some embodiments, the present invention provides a cell comprising a nucleic acid molecule, the construct or the vector encoding at least one amino acid comprising or consisting of an amino acid sequence selected from SEQ ID NOs: 17-27. According to some embodiment, the cell expresses or is capable of expressing the mAb or fragments thereof, the humanized mAbs or fragments thereof or the CAR of the present invention. According to some embodiments, the present invention provides a cell comprising a nucleic acid molecule comprising a nucleic acid sequence selected from SEQ ID NOs: 30-39. According to some embodiments, the cells are T cells. According to some embodiments, the T-cells are selected from memory, regulatory, helper or natural killer T-cells. According to some embodiments, the T cell is selected are from CD4+ T-cell and a CD8+ T-cell. According to some embodiments, the T cell are CD4+ T-cell and a CD8+ T-cell. According to some embodiments, the cells are NK cells. According to some embodiments, the cells are NK T-cells.

According to some embodiments, the present invention provides a cell culture comprising cells expressing the isolated polynucleotide of the present invention.

According to any one of the above embodiments, the cells are for use in treating cancer overexpressing SLeA carbohydrate. According to one embodiment, the cancer is selected from pancreatic, hematological, breast, ovarian, colorectal, stomach, head and neck, liver, lung, oropharyngeal cancer, squamous cell carcinoma and gallbladder cancer.

According to another aspect, the present invention provides a composition comprising the monoclonal antibody or the fragment thereof, the humanized monoclonal antibody or the antibody fragment thereof, the CAR, the conjugate or the cell comprising the mAb, humanized mAb and fragments thereof, of the present invention, and a carrier. The term "carrier" includes as a class any compound, solvent or composition useful in facilitating storage, stability, and use of the composition and its components. According to some embodiments, the composition is a pharmaceutical composition and the carrier is a pharmaceutically acceptable carrier. The term "pharmaceutical composition" as used herein refers to a composition comprising at least one active agent as disclosed herein, e.g. CAR T-cells, formulated together with one or more pharmaceutically acceptable carriers.

Formulation of the pharmaceutical composition may be adjusted according to applications. In particular, the pharmaceutical composition may be formulated using a method known in the art so as to provide rapid, continuous or delayed release of the active ingredient after administration to mammals. For example, the formulation may be any one selected from among plasters, granules, lotions, liniments, lemonades, aromatic waters, powders, syrups, ophthalmic ointments, liquids and solutions, aerosols, extracts, elixirs, ointments, fluidextracts, emulsions, suspensions, decoctions, infusions, ophthalmic solutions, tablets, suppositories, injections, spirits, capsules, creams, troches, tinctures, pastes, pills, and soft or hard gelatin capsules.

The pharmaceutical compositions of the present invention may be prepared by conventional techniques, e.g., as described in Remington: The Science and Practice of Pharmacy, 19th Ed., 1995. The compositions may be in solid, semisolid or liquid form and may further include pharmaceutically acceptable fillers, carriers or diluents, and other inert ingredients and excipients. The compositions can be administered by any suitable route, e.g., orally, intravenously, parenterally, rectally or transdermally, the oral route being preferred. The dosage will depend on the state of the patient, and will be determined as deemed appropriate by the practitioner.

The term “pharmaceutically acceptable carrier” or “pharmaceutically acceptable excipient” as used herein refers to any and all solvents, dispersion media, preservatives, antioxidants, coatings, isotonic and absorption delaying agents, surfactants, fillers, disintegrants, binders, diluents, lubricants, glidants, pH adjusting agents, buffering agents, enhancers, wetting agents, solubilizing agents, surfactants, antioxidants the like, that are compatible with pharmaceutical administration. The use of such media and agents for pharmaceutically active substances is well known in the art. The compositions may contain other active compounds providing supplemental, additional, or enhanced therapeutic functions, solid carriers or excipients such as, for example, lactose, starch or talcum or liquid carriers such as, for example, water, fatty oils or liquid paraffins.

Solutions or suspensions used for parenteral, intradermal, or subcutaneous application typically include the following components: a sterile diluent such as water for injection, saline solution, fixed oils, polyethylene glycols, glycerine, propylene glycol (or other synthetic solvents), antibacterial agents (e.g., benzyl alcohol, methyl parabens), antioxidants (e.g., ascorbic acid, sodium bisulfite), chelating agents (e.g., ethylenediaminetetraacetic acid), buffers (e.g., acetates, citrates, phosphates), and agents that adjust tonicity (e.g., sodium chloride, dextrose). The pH can be adjusted with acids or bases, such as hydrochloric acid or sodium hydroxide, for example. The parenteral preparation can be enclosed in ampules, disposable syringes or multiple dose glass or plastic vials.

According to some embodiments, the present invention provides a composition comprising a monoclonal antibody or the fragment thereof or the conjugate thereof or a plurality of cells comprising the mAb or the fragment comprising a VH and VL domains each comprising three CDRs and four FRs, wherein the VH-CDR 1 and 2 comprise amino acid sequences SEQ ID NOs: 3 and 4, respectively, VH-CDR 3 comprises an amino acid sequence selected from SEQ ID NO: 5 and 9; VL-CDRs 1 and 3 comprise amino acid sequences SEQ ID NOs: 6 and 12, respectively; and VL-CDR 2 comprises an amino acid sequence selected from SEQ ID NO: 10 and SEQ ID NO: 11, and a carrier. According to some embodiments, the fragment is an scFv, comprising a VH and VL domains comprising amino acid SEQ ID NO: 17 and 18, respectively, and a carrier. According to some embodiments, composition comprises the fragment being an scFv, comprising a VH and VL domains comprising amino acid SEQ ID NO: 19 and 20, respectively, and a carrier. According to some embodiments, the composition comprises a scFv comprising or consisting of SEQ ID NO: 21 or SEQ ID NO 22 or a functional analog thereof, as defined above, and a carrier. According to some embodiments, the composition comprises humanized monoclonal antibodies or fragments thereof comprising a VH domain comprising or consisting of an amino acid sequence selected from SEQ ID NO: 23 and 25, and a VL domain comprising or consisting of amino acid sequence SEQ ID NO: 24, and a carrier. According to some embodiments, the composition comprises a humanized fragment scFv comprises or consists of an amino acid sequence selected from SEQ ID NO: 26 and 27. According to some embodiments, the composition comprises a conjugate of the above mAbs or fragments and a carrier. According to some embodiments, the composition comprises a plurality of CARs comprising the above mAbs or fragments, and a carrier. According to some embodiments, the composition comprises a plurality of cells comprising the above mAbs or fragments and a carrier. According to some embodiments, the composition comprises a plurality of cells comprising the CAR of the present invention and a carrier. According to some embodiments, the composition comprises a plurality of cells comprising a nucleic acid molecule, the construct or the vector encoding at least one amino acid comprising or consisting of an amino acid sequence selected from SEQ ID NOs: 17-27, and a carrier. According to some embodiments, the cells are T cells. According to some embodiments, the T-cells are selected from memory, regulatory, helper or natural killer T-cells. According to some embodiments, the T cell is selected are from CD4+ T-cell and a CD8+ T-cell. According to some embodiments, the T cell are CD4+ T-cell and a CD8+ T-cell. According to some embodiments, the cells are NK cells. According to some embodiments, the cells are NK T-cells. According to some embodiments, the composition comprises a plurality of cells comprising at least one nucleic acid molecule comprising or consisting of a nucleic acid sequence selected from SEQ ID NOs: 30-39, and a carrier. According to some embodiments, the composition is a pharmaceutical composition and the carrier is a pharmaceutically acceptable carrier.

According to some embodiment, the present invention provides a pharmaceutical composition comprising T cells comprising or encoding the CAR of the present invention and a pharmaceutically acceptable carrier. According to some embodiments, the present invention provides a pharmaceutical composition comprising a plurality of T cells comprising or encoding the CAR comprising a VH domain comprising amino acid SEQ ID NO: 17 and the VL comprising amino acid sequence SEQ ID NO: 18 and a pharmaceutically acceptable carrier. According to some embodiments, the T cells comprise a CAR comprising VH domain comprising amino acid SEQ ID NO: 19 and the VL comprising amino acid sequence SEQ ID NO: 20. According to some embodiments, the present invention provides a plurality of T cells comprising a CAR comprising an ABD comprising or consisting of SEQ ID NO: 21 or SEQ ID NO 22, and a pharmaceutically acceptable carrier. According to some embodiments, the present invention provides a plurality of T cells comprising a CAR comprising a VH domain comprising or consisting of amino acid sequence selected from SEQ ID NO: 23 and 25, and a VL domain comprising or consisting of amino acid sequence SEQ ID NO: 24, and a pharmaceutically acceptable carrier. According to some embodiments, the present invention provides a plurality of T cells comprising a CAR comprising an ABD comprising or consisting of an amino acid sequence selected from SEQ ID NO: 26 and 27. According to some embodiments, the pharmaceutical composition comprises a plurality of T cells comprising a nucleic acid molecule comprising or consisting of a nucleic acid sequence selected from SEQ ID NOs: 30-39, and a pharmaceutically acceptable carrier. According to some embodiments, the T-cells are selected from memory, regulatory, helper or natural killer T-cells. According to some embodiments, the T cell is selected are from CD4+ T-cell and a CD8+ T-cell. According to some embodiments, the T cell are CD4+ T-cell and a CD8+ T-cell. According to some embodiments, the cells are NK cells. According to some embodiments, the cells are NK T-cells.

According to some embodiment, the present invention provides a pharmaceutical composition comprising an isolated monoclonal antibodies or fragments thereof of the present invention. According to some embodiments, mAb or the fragment comprises (i) a VH domain comprising amino acid SEQ ID NO: 17 and a VL domain comprising amino acid sequence SEQ ID NO: 18; (ii) a VH domain comprising amino acid SEQ ID NO: 19 and the VL domain comprising amino acid sequence SEQ ID NO: 20; (iii) a scFv comprising or consisting of SEQ ID NO: 21 or SEQ ID NO 22; (iv) a VH domain comprising or consisting of an amino acid sequence selected from SEQ ID NO: 23 and 25, and a VL domain comprising or consisting of amino acid sequence SEQ ID NO: 24; or (v) a scFv comprising or consisting of an amino acid sequence selected from SEQ ID NO: 26 and 27, and a pharmaceutically acceptable carrier. According to some embodiments, the pharmaceutical composition comprises a conjugate of the mAb or fragment thereof of the present invention, e.g. of the mAb or fragments of (i)-(v) above.

The pharmaceutical composition of the present invention is for use in treating cancer. According to some embodiments, the cancer overexpresses SLeA carbohydrate. Thus, according to some embodiments, the present invention provides a pharmaceutical composition comprising the isolated monoclonal antibodies of the present invention or fragments thereof or a conjugate thereof, for use in treating cancer. According to some embodiments, the present invention provides a pharmaceutical composition comprising the T cells comprising the CAR of the present invention for use in treating cancer overexpressing SLeA carbohydrate. According to some embodiments, the present invention provides a pharmaceutical composition comprising the T cells comprising the nucleic acid encoding the CAR of the present invention, for use in treating cancer overexpressing SLeA carbohydrate. According to one embodiment, the cancer is selected from hematological, breast, ovarian, pancreatic, colorectal, stomach, head and neck, liver, lung, oropharyngeal cancer, squamous cell carcinoma and gallbladder cancer. According to one embodiment, the cancer is pancreatic cancer. According to one embodiment, the cancer is a breast cancer. According to some embodiment, the cancer is a Her-2 negative breast carcinoma. According to another embodiment, the cancer is an ovarian cancer. According to a further embodiment, the cancer is a colon cancer. According to one embodiment, the cancer is colon adenocarcinoma. According to one embodiment, the cancer is a colorectal cancer. According to another embodiment, the cancer is a stomach cancer. According to one embodiment, the cancer is a pancreatic cancer. According to one embodiment, the cancer is carcinoma. According to one embodiment, the cancer is a hematological cancer overexpressing SLeA glycan. According to another embodiment, the cancer is a pancreatic adenocarcinoma. According to yet another embodiment, the cancer is lung cancer. According to one embodiment, the cancer is lung adenocarcinoma. According to some embodiments, the cancer is squamous cell carcinoma. According to another embodiment, the cancer is pharynx squamous cell carcinoma.

The term "treating" a condition or patient refers to taking steps to obtain beneficial or desired results, including clinical results such as inhibiting, preventing or arresting the development of a pathology (disease, disorder or condition) and/or causing the reduction, remission, or regression of a pathology. Beneficial or desired clinical results include, but are not limited to, or ameliorating abrogating, substantially inhibiting, slowing or reversing the progression of a disease, condition or disorder, substantially ameliorating or alleviating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and/or (e) limiting recurrence of symptoms in patients that were previously asymptomatic for the disorder(s). As used herein, the term "subject" includes mammals, such as human beings at any age which suffer from the pathology. According to some embodiment, the subject is a human subject, according to some embodiments, this term encompasses individuals who are at risk to develop the pathology.

The term "treating cancer" as used herein should be understood to e.g. encompass treatment resulting in a decrease in tumor size; a decrease in rate of tumor growth; stasis of tumor size; a decrease in the number of metastases; a decrease in the number of additional metastasis; a decrease in invasiveness of cancer; a decrease in the rate of progression of the tumor from one stage to the next; inhibition of tumor growth in a tissue of a mammal having a malignant cancer; control of establishment of metastases; inhibition of tumor metastases formation; regression of established tumors as well as a decrease in the angiogenesis induced by the cancer, inhibition of growth and proliferation of cancer cells and so forth. The term "treating cancer" as used herein should also be understood to encompass prophylaxis such as prevention as cancer reoccurs after previous treatment (including surgical removal) and prevention of cancer in an individual prone (genetically, due to life style, chronic inflammation and so forth) to develop cancer. As used herein, "prevention of cancer" is thus to be understood to include prevention of metastases, for example after surgical procedures or after chemotherapy.

The use comprises administering the pharmaceutical composition of the present invention to a subject. According to any one of the above embodiments, the composition of the present invention is administered as known in the art. According to one embodiment, the composition is parenterally administered, e.g. IP, IV, IM, SC or intratumorally. According to some embodiments, the pharmaceutical composition of the present invention is administered via infusion, such as IV infusion. According to some embodiments, the composition is systemically administered. According to other embodiments, the composition is locally administered.

The terms "administering" or "administration of" a substance, a compound, the composition or an agent to a subject are used herein interchangeably and refer to an administration mode that can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. According to some embodiments, the composition is administered 1, 2, 3, 4, 5 or 6 times a day. According to other embodiments, the composition is administered 1, 2, 3, 4, 5 or 6 times a month. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. According to one embodiment, the pharmaceutical composition is parenterally administered. The term "parenteral" refers to subcutaneous, intracutaneous, intravenous, intramuscular, intraarticular, intraarterial, intrasynovial, intrasternal, intrathecal, intralesional, intraperitoneal and intracranial injection, as well as various infusion techniques.

According to some embodiments, the pharmaceutical composition of the present invention is co-administered with other anti-tumor therapy including but not limited to anti-cancer drugs, radiotherapy, immunotherapy and surgery. According to some embodiments, the therapeutic agents suitable for co-administration with the pharmaceutical composition of the present invention are selected from chemotherapeutic agents, radioactive isotopes, toxins, cytokines such as interferons, immunostimulating agents, immunomodulating agents and antagonistic agents targeting cytokines, cytokine receptors or antigens associated with tumor cells. In some embodiments, an anti-cancer agent is a chemotherapeutic. According to some embodiments, the treatment comprises co-administering the pharmaceutical composition of the present invention together with an additional antibody. According to some embodiment, the additional antibody is an antibody that binds CA19-9 at a different position. According to some embodiment, the additional antibody is Ab 5b1. The terms "5b1" and "HuMab-5b1" refer to a human monoclonal antibody that binds to CA19-9 (SLeA).

According to another aspect, the present invention provides a method for treating cancer in a subject in need thereof comprising administering a therapeutically effective amount of the mAb antibodies, such as humanized mAbs, or functional fragments thereof of the present invention. According to another embodiment, the method comprises administering a pharmaceutical composition comprising the mAb or fragments thereof to the subject. According to another embodiment, the method comprises administering conjugates of the mAb or fragments thereof of the present invention to the subject. According to another embodiment, the method comprises administering CAR of the present invention to the subject. According to one embodiment, the method comprises administering T-cells comprising the CAR of the present invention to the subject. According to one embodiment, the method comprises administering T-cells comprising a nucleic acid molecule encoding the CAR of the present invention to the subject. According to yet another embodiment, the method comprises administering a pharmaceutical composition comprising cells comprising or expressing the mAb or the fragments thereof or the CAR, to the subject. According to some embodiments, the mAb antibodies or functional fragments thereof are formulated with a delivery system, such as liposomes.

According to yet another aspect, the present invention provides a use of the mAb antibodies of the present invention, or fragments thereof, the humanized mAb or fragments thereof, conjugates thereof, the CAR of the present invention or the T-cells of the present invention for preparing a medicament for treating cancer.

The present invention further provides use of the mAbs, fragments and conjugates of the present invention in a method of detecting, determining, and/or quantifying expression of SLeA on cells or presence of SLeA in a biological sample of a subject. According to some embodiments, detecting, determining, and/or quantifying the expression of SLeA or presence of SLeA may be used in diagnosing conditions associated with expression of SLeA, such as cancer. Thus, the mAb, the fragment of the present invention or the conjugates of the present invention are for use in cancer diagnosis, monitoring the progression of cancer, or monitoring and estimating the effectiveness of treatment of cancer. As used herein the term "diagnosing" refers to determining the presence or absence of a pathology (e.g., a disease, disorder, condition or syndrome), classifying a pathology or a symptom, determining a severity of the pathology (i.e., staging), monitoring pathology progression, forecasting an outcome of a pathology and/or prospects of recovery and screening of a subject for a specific disease (i.e., prognosing).

According to some embodiments, the present invention provides a method of detection of SLeA in tissue culture, in a tissue or in a section obtained from a subject.

The methods of determining or quantifying the expression of the SLeA according to any one of the above embodiments comprises contacting a biological sample with an antibody or antibody fragment, or conjugate thereof, and measuring the level of complex formation. Determining and quantifying methods may be performed in-vitro or ex-vivo. The antibodies according to the present invention may be also used to configure screening methods. For example, an enzyme-linked immunosorbent assay (ELISA), or a radioimmunoassay (RIA), as well as methods such as IHC or FACS, can be constructed for measuring levels of secreted or cell-associated SLeA glycan using the antibodies of the present invention and methods known in the art. According to some embodiments, the method for detecting or quantifying the presence of SLeA expressed on cells comprises the steps of:

(i) incubating a biological sample with the antibodies or antibody fragments of the present invention comprising at least an antigen-binding portion; and (ii) detecting the bound SLeA using a detectable probe.

According to some embodiments, the method further comprises the steps of:

(iii) comparing the amount of SLeA detected in (ii) to a standard curve obtained from a reference sample containing a known amount of SLeA; and (iv) calculating the amount of the SLeA in the sample from the standard curve.

Thus, according to some embodiments, the method comprises comparing the amount of SLeA to a reference.

According to some particular embodiments, the sample is a body fluid. According to some embodiments, the method is performed in-vitro, ex vivo or ex-vivo. According to some embodiments, the sample is obtained for a subject.

According to some embodiments, the present invention provides a method for diagnosing or monitoring cancer in a subject, the method comprises contacting a biological sample of the subject with the monoclonal antibodies or antibody fragments or conjugates of the present invention and assessing the amount of SLeA in the sample, wherein the cancer overexpresses SLeA glycan. According to some embodiments, the presence of SLeA in the sample above a particular threshold is indicative of the CA19-9+ malignancy. According to some embodiments, contacting a biological sample of the subject with the monoclonal antibodies or antibody fragments or conjugates of the present invention is performed under conditions that allow immunocomplexes formation.

The term "monitoring cancer" encompasses the term monitoring the progression of cancer and monitoring the effectiveness of treatment of cancer. In some embodiments, the present invention provides a method of diagnosing, assessing the severity or staging of a proliferative disease such as cancer in a subject, the method comprises detecting the presence or expression of SLeA in a biological sample of the subject using at least one antibody or antibody fragment of the present invention or the composition comprising same. According to some embodiments, the antibody or fragment thereof is conjugated or labeled. Thus, in the methods of detecting SLeA, diagnosing cancer and/or monitoring cancer, the conjugates of the present invention are used. According to some embodiments, the method comprises quantitatively comparing the level of expression of the SLeA glycan in a sample to a reference expression level of SLeA e.g. in corresponding sample of healthy subjects. According to any one of the above embodiments, the cancer is cancer in which SLeA is overexpressed.

The term "biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived therefrom and the progeny thereof. According to some embodiments, the biological sample is blood or serum. Additionally, the term may encompass circulating tumors or other cells. The term specifically encompasses a clinical sample, and further includes cells in cell culture, cell supernatants, cell lysates, serum, plasma, urine, amniotic fluid, biological fluids including aqueous humour and vitreous for eyes samples, and tissue samples. The term also encompasses samples that have been manipulated in any way after procurement, such as treatment with reagents, solubilisation, or enrichment for certain components.

According to any one of the above embodiments, the method of detecting SLeA, diagnosing or monitoring cancer comprises detecting SLeA in the sample, e.g. biological sample. According to some embodiments, the method comprises contacting the biological sample with the antibody or the fragment of the present invention. According to some embodiments, the method comprises contacting the biological sample with the conjugates of the present invention. According to some embodiments, the antibody or the fragment are marked, tagged or labeled. According to other embodiments, secondary antibodies may be used to determine the level of binging of the antibody of the present invention or the fragment to the biological sample of its components. According to some embodiments, any known methods for determining and quantifying the binding of an antibody or a fragment thereof to its target may be used. According to some embodiments, detecting comprises quantifying the amount of the SLeA.

According to some embodiment, the present invention provided a method of diagnosing cancer. According to some embodiment, the method comprises an assessment of the amount of SLeA in the biological sample of a subject and comparing it to a reference. According to some embodiments, the reference is the amount of SLeA in corresponding biological samples of healthy subjects. According to another embodiment, the method comprises comparing the measured amount of SLeA in the biological sample of the subject to a threshold. According to some embodiments, a change in expression of SLeA in comparison to expression in healthy subjects indicates the presence of cancer. According to some embodiments, overexpression of the SLeA correlates with cancer. Thus, in some embodiments, detecting SLeA expression level above the reference value or a threshold correlates with the presence of cancer. According to one embodiment, the present invention provides a method for diagnosing cancer in a subject, the method comprises contacting a biological sample of the subject with the monoclonal antibodies or antibody fragments or conjugates of the present invention, preferably under conditions which allow immunocomplexes formation, and assessing the amount of SLeA in the sample, wherein the cancer overexpresses SLeA glycan, wherein method comprises comparing the assessed amount of SLeA in the sample to a threshold or to a reference, wherein the reference is the level of SLeA in the sample of healthy subjects, and wherein the amount of the SLeA in the sample above the reference of the threshold is indicative of the CA19-9+ malignancy. According to some embodiments, the cancer is selected from pancreatic, breast, lung, ovarian, colon, stomach, oropharyngeal cancer, squamous cell carcinoma, head and neck and gallbladder cancer.

According to some embodiments, the present invention provides a method for monitoring cancer. According to one embodiment, monitoring cancer comprises monitoring the progression of cancer. According to other embodiments, monitoring cancer comprises monitoring the efficiency of treatment of cancer. According to some embodiments, monitoring comprises comparing SLeA content in a sample obtained from a subject at different times and assessing the propagation (i.e. monitoring) of the disease and/or effectiveness of treatment. According to some embodiments, monitoring cancer comprises comparing the amount of SLeA in the sample to the reference being the level of SLeA in the previous sample(s) of the subject, and a decrease in the amount of SLeA in comparison to the reference is indicative of amelioration of cancer. According to one embodiment, the present invention provides a method for diagnosing cancer in a subject, the method comprises contacting a biological sample of the subject with the monoclonal antibodies or antibody fragments of conjugates of the present invention, preferably under conditions that allow immunocomplexes formation, and assessing the amount of SLeA in the sample, wherein the cancer overexpresses SLeA glycan, wherein method comprises comparing the amount of SLeA in the sample to the reference being the level of SLeA in the previous sample of the subject, and a decrease in the amount of SLeA in comparison to the reference is indicative of amelioration of cancer.

According to any one of the above embodiments, the method further comprises consulting or providing recommendations regarding the treatment of the disease or condition or providing the treatment of the disease, such as cancer. According to any one of the above embodiments, the method further comprises treating cancer. Thus, according to some embodiment, the present invention provides a method of treating a CA19-9+ malignancy in a subject in need thereof, the method comprising: (a) diagnosing the CA19-9+ malignancy in the subject by the methods of the present invention, and (b) treating the CA19-9+ malignancy when the malignancy is indicated.

According to some embodiments, the present invention provides a method of monitoring treatment of a CA19-9+ malignancy cancer treatment, the method comprises determining a level of CA19-9 in a subject in need thereof as described above before and after treating the CA19-9+ malignancy, wherein a decrease in said level following said treating is indicative of efficacious treatment.

According to another aspect, the present invention provides a kit for measuring the level or amount of SLeA in a sample, the kit comprising the isolated monoclonal antibodies, fragments thereof or conjugates of the present invention. According to one embodiment, the sample is a biological sample. According to some embodiment, the kit comprises means for quantifying the amount or the level of the isolated mAbs, fragments or conjugates of the present invention bound to SLeA present in the sample. According to some embodiments, the means is ELISA kit. According to some embodiments, the means are means for performing ELISA. According to some embodiments, the means are means for performing immunoassay test. According to some embodiments, the kit comprises instructions for measuring the amount of SLeA in the sample. According to some embodiments, the kit comprises instructions for assessment or detecting the amount of the level of SLeA using the kit. According to some embodiments, the kit is an assay kit. According to any one of the above embodiments, the kit is a diagnostic kit. Thus, according to some embodiments, the present invention provides a kit comprising at least one ELISA kit for determining the level of at SLeA in a biological sample, and instructions for use.

Any one of the above embodiments and aspects apply and are encompassed herein as well. According to some embodiments, the isolated mAb, fragment or conjugate used in the kit comprises a VH and VL comprising amino acid sequences SEQ ID NO: 17 and 18, respectively. According to some embodiments, the isolated mAb, fragment or conjugate used in the kit comprises a VH and VL comprising amino acid sequences SEQ ID NO: 19 and 20, respectively. According to some embodiments, the isolated mAb, fragment or conjugate used in the kit comprises a VH and VL comprising amino acid sequences SEQ ID NO: 23 and 24, respectively. According to some embodiments, the isolated mAb, fragment or conjugate used in the kit comprises. According to some embodiments, the isolated mAb, fragment or conjugate used in the kit comprises a VH and VL comprising amino acid sequences SEQ ID NO: 25 and 24, respectively. According to some embodiments, the isolated mAb, fragment or conjugate used in the kit comprises a single chain variable fragment (scFv) comprising an amino acid sequence selected from SEQ ID NO: 21 and 22. According to some embodiments, the isolated mAb, fragment or conjugate used in the kit comprises a humanized scFv comprising an amino acid sequence selected from SEQ ID NO: 26 and 27. According to some embodiments, the isolated mAb, fragment or conjugate used in the kit comprises an analog of the above defined isolated mAb, fragment and conjugate having at least 90% sequence identity to the sequence and no substitution is introduced into CDRs, into positions 99 and 100 of VH and into positions 43 and 87 of VL.

According to some embodiments, the kit is for diagnosing a cancer in a subject. Thus, according to some embodiments, the kit comprises means for comparing the amount or the level of SLeA in the sample and in a reference. According to some embodiments, the kit further comprises reference levels of the SLeA in healthy subjects. According to some embodiments, the kit comprises means for performing analysis in a plurality of times and means for comparison of the results obtained in the measurement.

By using the kit, a person skilled in the art may measure the amount of SLeA present in the biological sample and compare it to a reference. According to some embodiments, the kit is for monitoring the treatment or development of the cancer, and the kit comprises means for measurement of the amount of SLeA in biological samples two or or more times. In case of monitoring the treatment of development of the cancer the reference may be the previously taken biological sample of the subject or the results obtained in the previous measurement.

According to some embodiments, the isolated monoclonal antibody, the humanized isolated monoclonal antibody or a fragment thereof or the conjugate thereof is immobilized to a solid support. According to some embodiments, the humanized isolated monoclonal antibody or a fragment thereof or the conjugate thereof is is attached to a detectable moiety.

According to some embodiments, the Abs, fragments or conjugates are immobilized on a solid surface. Any solid surface may be used such as chip or microarray. According to some embodiments, the solid phase is a membrane. According to another embodiment, the solid phase is a polymers. Non limiting examples of solid phases are nitrocellulose, polyvinylidene fluoride (PVDF); hydrophobic (Charge-modified) nylon and polyethersulfone (PESU). Alternatively, the solid phase may be a woven meshes, synthetic nonwovens, cellulose and glass fiber.

According to alternative embodiments, the Abs, fragments or conjugates are dissolved in a solvent. According to some embodiments, the Abs, fragments or conjugates are linked to beads.

According to some embodiments, the kit comprises means for quantifying the amount of antibodies bound SLeA.

According to some embodiments, the monoclonal Abs of the present invention, the fragments thereof, the conjugates or the CAR T cells are for use in preventing or treating a laminin-associated disease or condition in a subject in need thereof, including cancer.

According to some aspect, the present invention provides an article of manufacture comprising the antibody, fragment thereof, conjugate, CAR or T cell of the present invention being packaged in a packaging material and identified in print, in or on said packaging material. According to some embodiments, an article of manufacture is for use in the treatment of a CA19-9+ malignancy. According to some embodiments, the article of manufacture further comprising a chemotherapeutic agent and/or another antibody, which binds CA19-9 at a different position than said antibody. Once antibodies are obtained, they may be tested for activity, for example via ELISA. According to some embodiments, the CA19-9+ malignancy comprises pancreatic cancer.

According to some embodiments, the present invention provides a method of producing an antibody to CA19-9, the method comprising: (a) culturing cells of claim comprising a nucleic acid encoding for the mAb of the present invention under conditions which allow for expression of said vH and/or vL chains; and (b) recovering the vH and/or vL chains from the cells. According to some embodiment, the cells are HEK 293 cells. According to some embodiment, the method further comprising subjecting said vH and vL chains to refolding.

As used herein the term "about" refers to +10%.

The terms "comprising", "comprise(s)", "include(s)", "having", "has" and "contain(s)," are used herein interchangeably and have the meaning of "consisting at least in part of". When interpreting each statement in this specification that includes the term "comprising", features other than that or those prefaced by the term may also be present. Related terms such as "comprise" and "comprises" are to be interpreted in the same manner. The terms "have", "has", having" and "comprising" may also encompass the meaning of "consisting of" and "consisting essentially of", and may be substituted by these terms. The term "consisting of" excludes any component, step or procedure not specifically delineated or listed. The term "consisting essentially of" means that the composition or component may include additional ingredients, but only if the additional ingredients do not materially alter the basic and novel characteristics of the claimed compositions or methods.

As used herein, the singular form "a", "an" and "the" include plural references unless the context clearly dictates otherwise. For example, the term "a compound" or "at least one compound" may include a plurality of compounds, including mixtures thereof. The term "and/or" is used to indicate one or both stated cases may occur, for example A and/or B includes, (A and B) and (A or B).

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition.

Having now generally described the invention, the same will be more readily understood through reference to the following examples, which are provided by way of illustration and are not intended to be limiting of the present invention.

EXAMPLES

Reference is now made to the following examples, which together with the above descriptions illustrate some embodiments of the invention in a non limiting fashion.

Materials and Methods

Cloning of RA9 and 5b1 Antibodies.

RA9 Native was cloned as published (Amon et al., 2020). Sequences of 1116NS19.9 (referred as RA9 Native or Native) VH and VL were obtained from the IMGT database (Giudicelli et al., 2006) (accession number S65761 and S65921, respectively, confirm SEQ ID NOs: 7 and 8). 5b1 were obtained from Sawada et al., 2011 (Clinecal cancer research, 6, 17, 1024-1032). Then, scFv of N'-VH and C'-VL of RA9 and 5b1 antibodies with GGGGSGGGGSGGGGS linker was synthesized by Integrated DNA Technologies Inc. (IDT, Israel). The scFv DNA sequence was optimized for codon usage compatible with expression in human cells, without altering the amino acid sequence. In addition, the scFv sequence was flanked by plasmid homology regions at the 5' and 3' ends (36 and 45 nucleotides, respectively). The flanking regions contained 5'-NdeI and 3'-BamHI restriction enzyme cloning site in-frame with the scFv. pETCON2 plasmid contain HA and c-Myc tags to label the scFv. The N-terminal HA tag starts 30 amino acids upstream to VH, the C-terminal c-Myc tag starts 5 amino acids downstream to VL, and there is a GGGS linker in between the end of VL to the start of c-Myc tag. pETCON2 plasmid was digested with NdeI and BamHI (Fermentas). Digested vector was extracted from 0.9% agarose gel using Wizard SV GEL & PCR clean-up system (Promega). EBY100 yeast cells were transformed with native scFv by LiAc/SS Carrier DNA/peg method. EBY100 yeast cells were transformed with 500 ng of synthesized native scFv and 167 ng digested plasmid for in vivo ligation by LiAc/SS Carrier DNA/peg method, as described (Gietz and Schiestl, 2007, Nat Protoc 2, 1-4). Cloned Native scFv-pETCON2 plasmid were extracted from transformed yeast and scFv sequence validated at Tel Aviv University sequencing core facility.

Induction of scFv Expression on YSD System

Transformed yeast cells were individually cultured in synthetic defined media (SD) lacking Tryptophan (Trp) [SD-Trp; 2% glucose (Sigma), 0.67% yeast nitrogen base w/o amino acids (BD), 0.54% $Na_2HPO_4$ (Sigma), 0.86% $NaH_2PO_4$ (Sigma) and 0.192% yeast synthetic drop-out medium supplements without Trp (Sigma)] at 30° C., passaged 1:10 each day for three days, then scFv surface expression induced by changing the media to synthetic galactose (SG) based media [SG-Trp; 2% galactose (Sigma), 0.2% glucose, 0.67% yeast nitrogen base w/o amino acids, 0.54% $Na_2HPO_4$, 0.86% $NaH_2PO_4$, and 0.192% yeast synthetic drop-out medium supplements without Trp] and the temperature to 20° C., and cells were grown overnight to obtain Native scFv-YSD cells.

Assessment of scFv Functional Reactivity by Fluorescence-Activated Cell Sorting (FACS)

Induced Native scFv-YSD cells were functionally analyzed for antigen binding by FACS as published (Amon et al., 2020). Target antigens in a nanoparticle polymer expression mode resembling its presentation on cancer cells with multivalent expression on polyacrylamide polymers carrying biotin tags (7-9 glycans per ~30 kDa PAA-Bio; biotin at approximately every 5th amide group) was used. Thus, nanoparticles multivalent-glycans in the form of polyvalent $SLe^a$-PAA-biotin was used. The non-specific target antigen $Le^a$-PAA-biotin was used as a negative control. $5\times10^6$ Native scFv-YSD cells were washed with 1 ml assay buffer (PBS, 0.5% ovalbumin) then incubated with 1 μM $SLe^a$-PAA-biotin or 1 μM $Le^a$-PAA-biotin antigens and 1:50 diluted mouse-anti-c-Myc (4 μg/ml), both in assay buffer for 1 h at room temperature (RT) with rotation. Cells were washed with 1 ml ice cold assay buffer, then incubated for 40 min on ice with APC-streptavidin and Alexa-Fluor-488-goat-anti-mouse IgG1 diluted 1:50 (10 μg/ml) and 1:200 (10 μg/ml) respectively in assay buffer. Cells were washed with 1 ml ice cold PBS, then resuspended in 500 μl PBS. Cell fluorescence was measured by CytoFLEX flow cytometry (Beckman Coulter) and analyzed with Kaluza analysis software.

Cloning and Expression of RA9 Full Length Antibody.

Cloning was done by Gibson assembly. Variable heavy and light fragments of native RA9 clone was amplified by PCR. Reaction was made in Q5 reaction buffer, with 1 μL of plasmid DNA template (65-98 ng), 200 μM each dNTP, 1 U Q5 hot start high fidelity DNA polymerase (New England Biolabs), 500 nM each primer complete volume to 50 μL with PCR grade water. PCR conditions were 95° C. for 2 min followed by 30 cycles of 95° C. for 30 s, 61° C. for 60 s, 72° C. for 60 s, and final incubation of 72° C. for 5 min. To remove template segments, the PCR product was supplemented with 6 μL of 10× CutSmart Buffer, 20 U DpnI (New England Biolabs), and completed the volume to 60 μL with PCR grade water, then incubated at 37° C. for 1 h. PCR digested fragments were purified from agarose gel by Zymoclean Gel DNA Recovery Kit (Zymo Research). Heavy and light chain full IgG p3BNC expression plasmids were divided to three parts for PCR amplification, variable region, left and right arm. Left and right arms of heavy and light p3BNC plasmids were amplified, digested and purified as described for variable regions using appropriate primers. Of each fragment, variable region, right and left arms, 25 ng were taken for Gibson assembly. Reaction was made in isothermal reaction buffer containing 5% PEG 8000, 100 mM Tris-HCl pH 7.5, 10 mM $MgCl_2$, 10 mM DTT, 0.2 mM of each dNTP and 10 mM NAD. To this buffer we added 0.04 U T5 exonuclease (NEB), 0.25 U Phusion polymerase (NEB) and 40 U Taq DNA ligase (NEB), and ligation was made at 50° C. for 1 h. Plasmids were electroporated into XL1 *Escherichia coli*, to validate the sequence and producing high amount of p3BNC expression plasmids. Human embryonic kidney 293A cells were then used to produce full length whole native RA9 antibody from the RA9-p3BNC expression plasmids template transfected with polyethylenimine reagent (PEI; Polysciences). Antibodies were purified using protein A (GE healthcare) and concentrations determined by BCA assay (Pierce). Functionality of cloned antibody was tested by ELISA against antigen-coated plates, and by FACS against biotinylated antigen and against antigen-positive cancer cells.

Protein Expression and Purification.

To produce larger amounts of recombinant Abs, HEK293F cells maintained in FreeSyle medium (Gibco) were transfected with the p3BNC plasmids encoding the heavy and the light chains of Abs (SEQ ID NOs: 1 and 2; 17 and 18; 19 and 20, respectively). As transfection reagent, 40 kDa polyethyleneimine (Polysciences) with DNA/polyethyleneimine ratio of 1 μg/3 μl was used. Cells were maintained for 5-7 days in suspension before harvesting the supernatants. After clarifying the supernatants by centrifugation, Abs were captured using protein-A affinity chromatography (GE lifesciences). Abs were eluted using 0.1 M citric acid pH3 buffer which was adjusted to pH 8.0 using Tris-HCl. For obtaining the Fab portions, papain enzyme (Sigma-Aldrich) was used to digest Abs in 1:1 buffer-protein sample ratio with enzyme and protein ratio being ~1:80. Cutting buffer contained 20 mM Cystein-HCl (Sigma-Aldrich) and 10 mM EDTA tittered to pH7 with Tris buffer pH8. Cutting was performed for 90 minutes in 37° C. Negative protein-A was performed to remove Fc fragments followed by SEC on a Superdex 200 column.

Crystallization.

For protein crystallization, a mosquito crystallization robot (TTP Labtech) was used to set vapor diffusion in sitting drop experiments using 96-well iQ plates (TTP Labtech), for each well, we tested three ratios of protein (80, 120 and 160 nl) to reservoir (120 nl). PEGrx-HT screen (Hampton Research) was used to identify initial hits which were obtained for apo-Ab 1116NS19.9 for the condition containing 0.10% w/v n-Octyl-b-D-glucoside, 0.1 M Sodium citrate tribasic dihydrate pH 5.5 and 22% w/v Polyethylene glycol 3,350. Further optimization was done by growing the crystals in 7.5% ethylene glycol for cryo-preservation. Protein with ligand CA19-9 (Neu5Ac-α2,3-$Le^a$ βProNH2) was mixed in a ratio of 1:1.2 protein to ligand, protein samples gave crystals when grown on a 24 well sitting plate with a 1:1 ratio of protein-ligand and reservoir. Ab 5b1 apo- and halo-protein crystals came from the same drop with 0.1M NaCl, 0.1M bis-tris propane pH9, 18% poly ethylene glycol 1,500 and 5% glycerol. Protein to glycan ratio was 1:1 and protein to reservoir 1.75:1. All crystals were grown in 20° C.

Data Collection, Structure Solution and Refinement.

X-ray diffraction data was collected at the European Synchrotron Radiation Facility (ESRF) using a ADSC. Q315R detector at 100° K. Data up to 1.5 Å at beamline ID23-1 was collected for the apo and halo Fab 1116NS19.9 belonging to the tetragonal and orthorhombic space groups respectively. Data was indexed, integrated, and scaled using XDS. The present inventors used Phaser to obtain molecular replacement solution with the structure of NIH45-46 (PDB: 3u7w) and used the solved structure for molecular replacement of Fab 5b1 halo- and apo-proteins. Data for halo- and apo-Ab 5b1 (representing bound an unbound to antigen, respectively) was collected at beamline ID23-2 and data resolution extended to 2.4 Å for the apo and halo structures which belong to the hexagonal space group with 3 and 6 molecules in the asymmetric unit respectively. All models were manually traced into electron density maps using Coot 17 and refined using Phenix Refine in an iterative fashion.

Surface Plasmon Resonance (SPR) Measurements.

All measurements were performed using a Biacore T200 (GE Healthcare) at 25° C. Abs were immobilized to a protein-A chip from a stock of 20 μg/ml to a similar surface density. CA19-9 glycan in TBS buffer with azide 0.02% was used as analyte in a series of increasing concentrations from 0 until 500 μM with 14 steps total. Affinity constants were calculated from measuring binding at steady states. Regeneration was preformed using 10 mM glycine-HCl, pH 1.5. Sensorgrams were analyzed with the Biacore T200 evaluation software.

Example 1. Determining the Structure of CA19-9 in Complex with Two mAbs

Figure 2:
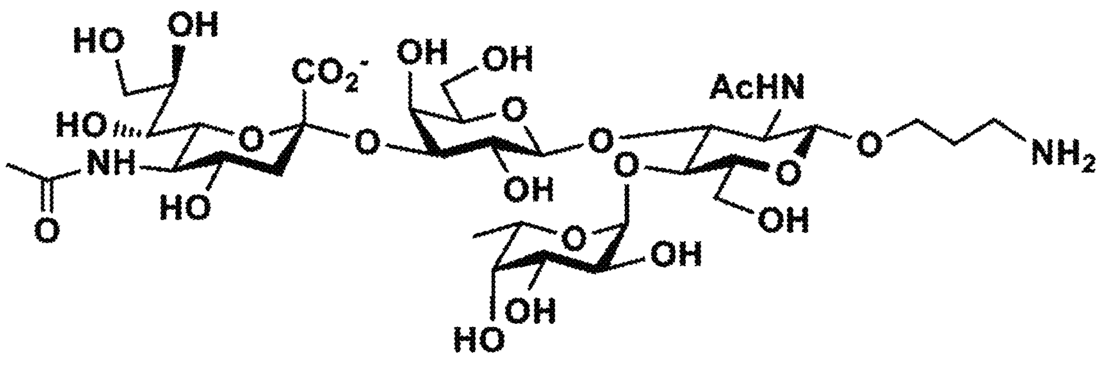
FIG. 2. shows the structure of SLeAβProNH used as a ligand for crystallization.

To reveal how Abs recognize CA19-9, two of the most prevalent mAbs: Ab 1116NS19.9 and Ab 5b1 that are currently utilized in diagnostic kits and are evaluated in clinical trials, respectively, were selected for structural studies. Sequences encoding the variable regions of the two mAbs were cloned into a human IgG1 scaffold (SEQ ID NOs: 28-33). The mAbs were produced in HEK293F cells and purified using protein-A affinity chromatography. Fab fragments were obtained using papain digest of the IgGs followed by separation of the Fabs from the Fc fragments using protein-A affinity, and size exclusion chromatography. SleAβProNH was used as a ligand for crystallization (FIG. 2). Both the apo and the CA19-9-holo states of Fab 1116NS19.9 as well as Fab 5b1 were crystalized. These crystals were subjected to X-ray analyses at the European Synchrotron Radiation Facility. Complete data sets were obtained at 1.6 Å and 1.5 Å resolutions for the CA19-9-bound and the apo-state of mAb 1116NS19.9, respectively (Table 1). Further collected were complete data sets at 2.4 Å resolutions for the CA19-9-bound and the apo-Fab of Ab 5b1 (Table 1). All structures were solved using molecular replacement, for the apo mAb 1116NS19.9 a human-derived Fab (PDB: 3U7W) was used as a research model and subsequently used the 1116NS19.9 structure as a search model for solving the rest of the structures through molecular replacement. In the holo structures of both 1116NS19.9 and 5b1, clear electron density for CA19-9 was observed, allowing to accurately model it.

GAL, all hydroxyl groups facing the protein are engaged in bonds were found for Ab 5b1.

Carbon 6 of the NAG ring is the connecting position to the second SIA moiety in the version of CA19-9 appearing in healthy subject, i.e. di Sialyl Lewis-A (FIG. 1). Focusing on this position in the structure of Ab 1116NS19.9, it is evident that the hydroxyl extending from carbon 6 is facing the Ab, leaving no room for accommodating the extra SIA and hence providing an explanation for the selectivity of this Ab towards CA19-9. Moreover, the binding of CA19-9 to Ab 1116NS19.9 is in part facilitated by several polar interactions that the free hydroxyl extending from carbon 6 is forming with the heavy chain Asn52A and Asn53, providing an additional structural explanation for the selectivity of this Ab. As for Ab 5b1, the hydroxyl extension from carbon 6 of NAG is not buried at the interface with the protein. Yet, this hydroxyl is also engaged in a water-mediated interaction with Asp93 of the light chain, providing at least a partial explanation for the inability of Ab 5b1 to efficiently cross react with di Sialyl Lewis-A (data not shown).

For Ab 1116NS19.9, all CDRs are involved in ligand binding aside from CDRL1; CDR L3 acts as the main contributor. CDR contact analysis for Ab 5b1 indicates that CDR-H1 and CDR-H2 are not involved in binding while

TABLE 1

Data collection and refinement statistics for holo- and apo- Ab 1116NS19.9 and Ab5b1.

| Parameter | Holo-Ab 1116NS19.9 | Apo-Ab 1116NS19.9 | Holo-Ab 5b1 | Apo-Ab 5b1 |
|---|---|---|---|---|
| Wavelength (Å) | 0.97242 | 0.97242 | 0.87313 | 0.87313 |
| Space group | $P\ 2_1\ 2_1\ 2$ | $P\ 4\ 2_1\ 2$ | $P\ 3_1$ | $P\ 3_2$ |
| | | Cell dimensions | | |
| a, b, c (Å) | 89.17 60.20 84.44 | 64.92, 64.92, 242.60 | 152.5 152.5 60.9 | 155, 155, 122 |
| α, β, γ ° | 90 90 90 | 90 90 90 | 90 90 120 | 90 90 120 |
| Resolution (Å) | 44.58-1.55 (1.6-1.55)$^a$ | 45.9-1.51 (1.564-1.51) | 47.58-2.41 (2.49-2.41)$^a$ | 47.88-2.41 |
| $R_{meas}$ (%) | 5.9 (158)$^{ab}$ | 13.4 (103.1) | 15.7 (119.8)$^a$ | 8.1 (100.1)$^a$ |
| $R_{pim}$ | 2.5 (65.1)$^{ab}$ | 4.4 (32.9) | 9.4 (71.6)$^a$ | 4.3 (52.1)$^a$ |
| $CC_{1/2}$ | 99.9 (56.8)$^{ab}$ | 99.6 (79.2) | 99.5 (50.8)$^a$ | 99.5 (54.1)$^a$ |
| I/I | 13 (1.1)$^{ab}$ | 9.4 (2.3) | 9.3 (1.4)$^a$ | 5.9 (1.4)$^a$ |
| Completeness (%) | 95 (95.2)$^{ab}$ | 99.9 (100) | 99.8 (98.1)$^a$ | 99.4 (98.4)$^a$ |
| Multiplicity | 2.9 (3)$^{ab}$ | 9.1 (9.4) | 5.1 | 3.6 |
| Reflections | 359539 | 753716 | 314162 | 537864 |
| Unique reflections | 64876 | 82652 | 61056 | 150444 |
| | | Refinement | | |
| Resolution (Å) | 44.58-1.55 | 45.1-1.51 | 47.58-2.41 | 46.84-2.41 |
| No. of reflections | 64837 | 82524 | 61028 | 126005 |
| $R_{work}/R_{free}$ (%) | 17.44/20.08 | 16.18/18.31 | 16.63/21.41 | 17.26/21.83 |
| | | No. of atoms | | |
| Protein | 3356 | 3357 | 9995 | 20129 |
| Ligand/ion | 57 | — | 192 | — |
| Water | 382 | 677 | 770 | 1543 |
| | | B factors | | |
| Protein | 38.67 | 21.51 | 43.86 | 47.66 |
| Ligand/ion | 33.85 | — | 43.86 | — |
| Water | 45.09 | 35.20 | 46.37 | 48.68 |
| | | Ramachandran | | |
| Favored (%) | 98.12 | 98.36 | 97.75 | 96.46 |
| Allowed (%) | 1.88 | 1.64 | 2.25 | 3.35 |
| Outlier (%) | 0.0 | 0.0 | 0.0 | 0.19 |
| | | RMSD | | |
| Bond length (Å) | 0.007 | 1.35 | 0.005 | 0.009 |
| Bond angles ° | 1.11 | 0.009 | 0.769 | 0.987 |

[a]Values in parentheses are for the highest resolution-shell

Example 2. Molecular Basis for Recognition of CA19-9 by Ab 1116NS19.9 and Ab 5b1

Figure 3A:
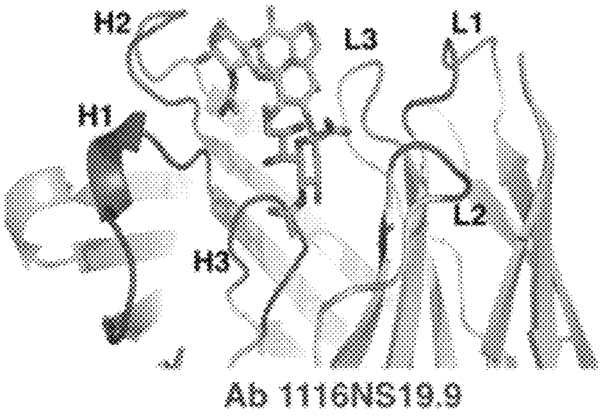
FIG. 3 shows the Fabs and CDR regions for Ab 1116NS19.9 (FIG. 3A) and Ab 5b1 (FIG. 3B), and their involvement in binding CA19-9.
Figure 3B:
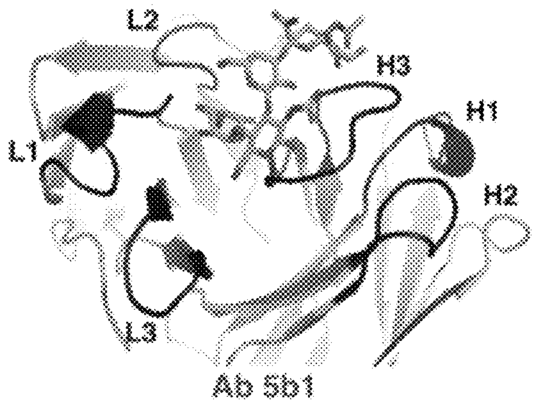
Figure 4A:
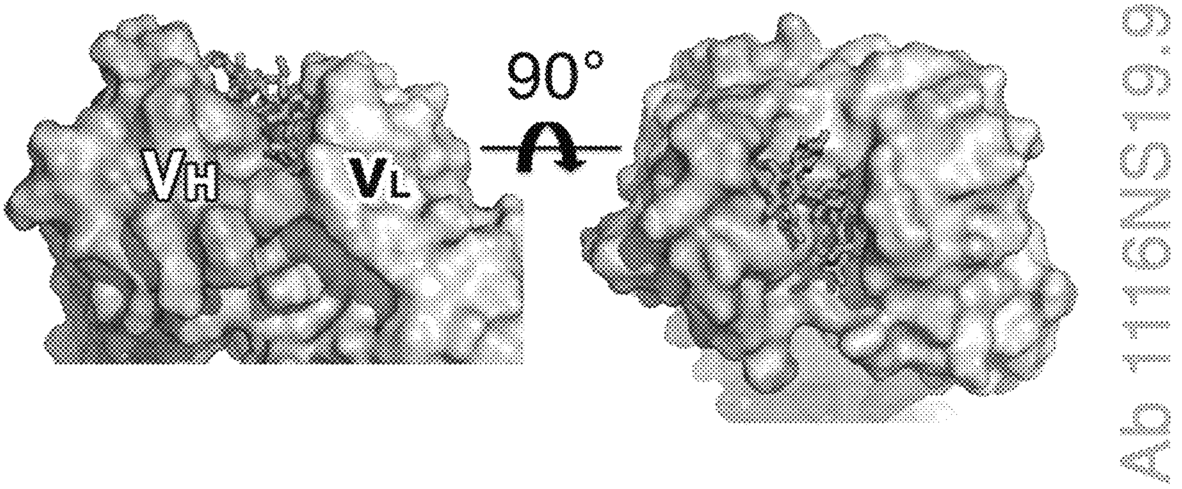
FIG. 4. shows a surface representation of the variable regions of Ab 1116NS19.9 (also referred to as "RA9"; "Native" or "WT") (FIG. 4A) and Ab 5b1 (FIG. 4B) with CA19-9.
Figure 4B:
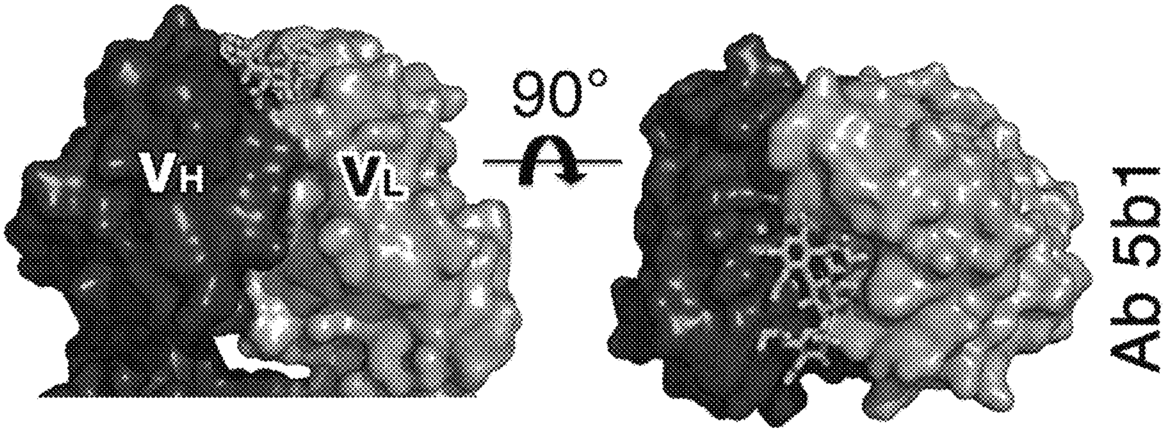

Considering the relatively small size of CA19-9 (819 Dalton) and its hydrophilic nature as a glycan, CA19-9 is regarded as a non-optimal immunogen. Therefore, it was anticipated that the Abs should be engaged in few bonds with CA19-9. In contrast, the refined models of bound Fab 1116NS19.9 and Fab 5b1 display an overall extended network of bonds between CA19-9 and the Abs CDR (FIG. 3A and FIG. 3B). For Ab 1116NS19.9, aside from oxygen 7 of the sialic acid hydroxyl, all hydroxyl groups facing the protein form direct or solvent-mediated bonds with Ab 1116NS19.9. A saturated network aside from oxygen 4 of CDR H3 and CDR L1 are the major contributors for binding. Ab 1116NS19.9 binds CA19-9 in a relatively deep groove (FIG. 4A) in comparison to Ab 5b1, which displays a more superficial binding of CA19-9 (FIG. 4B). The buried surface area for the complex of CA19-9 and Fab 1116NS19.9 is 973 $Å^2$ (549 $Å^2$ on CA19-9 and 424 $Å^2$ on the Fab). Measurements for Fab 5b1 were calculated as 859 $Å^2$ (487 $Å^2$ on CA19-9 and 372 $Å^2$ on the Fab). Calculations were performed using CCP4 AreaMol tool.

Figure 5:
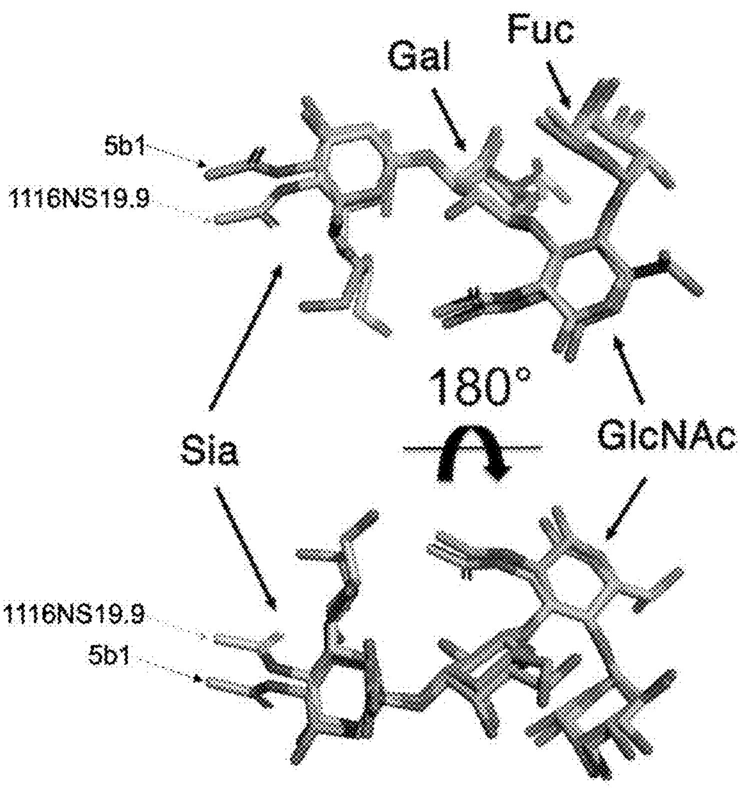
FIG. 5 shows a superposition of CA19-9 from Ab 1116NS19.9 (light gray) and Ab 5b1 (dark gray) structures.

Example 3. Low Energy Conformer for CA19-9 with Different Recognition Modes by Abs Oligosaccharides are flexible in solution and as a result can display an ensemble of conformations. Surprisingly, CA19-9 bound to both Ab 1116NS19.9 and to Ab 5b1 assumes a highly similar conformation (FIG. 5). Of note, these two Abs, were isolated from different species (i.e. mouse vs. human, respectively) and were elicited against CA19-9 that was displayed in two very distinct contexts (i.e. on carcinoma cells and as KLH-conjugated ligand). This relatively similar structure for CA19-9 indicates, according to one non-limiting estimation, for an energetically preferred conformer for CA19-9. Placing the Abs into the superposed CA19-9 overlay in their binding compatible orientation, positioned the Abs approximately in a 45° angle relative to one another (not shown). Different recognition solutions observed here for the Abs in binding CA19-9 may suggest an advantageous benefit for combining the two Abs to produce an optimal therapeutic outcome involving a synergistic effect.

Example 4. Optimization of Ab 1116NS19.9 in Targeting CA19-9 Using the AbLIFT Method Increasing sensitivity of CA19-9 recognition is of great interest for advancing diagnosis and management of CA19-9 positive malignancies such as pancreatic cancer. Focusing on Ab 1116NS19.9, which is currently in use for diagnostic applications, the Ab was further modified using AbLIFT method, which allows stabilizing binding conformation (Warszawski et al., PLOS Comput. Biol. 2019, 15 (8), e1007207). The structural data of Ab 1116NS19.9 bound to CA19-9 reveals an extensive network of bonds situating CA19-9 in a deep groove where nearly all hydroxyl groups facing the protein are involved in hydrogen bonds. The server designed for performing the calculation according to the method (http://AbLIFT.weizmann.ac.il) was provided with coordinates of Ab 1116NS19.9 bound to CA19-9, and a ranked list of 20 energetically favored mutations in the VH and VL interface (Table 2) was obtained.

TABLE 2

AbLIFT designs with selective mutations for heavy and light chains of Ab 1116NS19.9 as provided by the AbLIFT server and ranked by free energy. The amino acids are numbered according to KABAT numbering system. The two Ab designs superior to the WT, design 2 and 15 are marked in bold italic font. Designs obtained by AbLIFT methods are referred as AbLIFT designs.

| Design | Δ G | 43L | 56L | 87L | 98L | 35H | 93H | 94H | 98H |
|---|---|---|---|---|---|---|---|---|---|
| **Native** | | **S** | **D** | **Y** | **F** | **D** | **T** | **T** | **Y** |
| Des1 | −460.882 | P | P | W | W | T | V | T | Y |
| ***Des2*** | ***−459.148*** | ***P*** | ***V*** | ***W*** | ***W*** | ***D*** | ***V*** | ***V*** | ***Y*** |
| Des3 | −459.019 | S | K | Y | W | K | V | T | F |
| Des4 | −458.975 | P | E | W | W | L | V | V | F |
| Des5 | −458.945 | P | P | Y | W | L | V | V | Y |
| Des6 | −458.9 | P | D | W | W | L | V | S | Y |
| Des7 | −458.891 | P | H | W | W | Q | V | T | F |
| Des8 | −458.79 | P | P | W | F | K | A | V | Y |
| Des9 | −458.762 | S | A | W | W | Q | V | T | Y |
| Des10 | −458.65 | P | K | W | W | Q | A | T | Y |
| Des11 | −458.636 | P | Q | W | W | L | A | T | F |
| Des12 | −458.375 | S | P | W | W | K | A | T | Y |
| Des13 | −458.358 | P | A | W | W | K | V | M | Y |
| Des14 | −458.32 | P | V | Y | W | G | V | T | F |
| ***Des15*** | ***−458.231*** | ***P*** | ***P*** | ***W*** | ***W*** | ***D*** | ***A*** | ***V*** | ***F*** |
| Des16 | −458.219 | P | S | W | W | N | V | A | F |
| Des17 | −458.169 | P | P | W | W | E | I | T | F |
| Des18 | −458.139 | P | P | W | F | Q | T | V | F |
| Des19 | −458.125 | P | T | W | W | Q | T | V | Y |
| Des20 | −458.1 | S | P | W | W | L | T | T | F |

This region (VH and VL interface) is prone to suboptimal packing giving room for conformational sampling affecting the antigen binding site availability. Deep complementary mutations in the interface region have the potential to fixate the antigen binding site in a binding-competent conformation by that enabling a lower kon rate. Priming the Ab in a binding compatible conformation prior to antigen binding allows minimizing the entropic cost of binding the antigen by eliminating conformational sampling of the unbound Ab. 17 designs were calculated to have the most significant favorable change in Rosetta free energy (ΔΔG) of the variable domain and were different by at least three mutations from the parental antibody and from other designs. In order to produce the AbLIFT designs, multiple-primer PCRs were performed so as to successfully clone and express these selected 17 designs in HEK293F cells. A preliminary screen of the binders was performed for 17 expressed designs using single cycle SPR experiments with five concentration points of CA19-9 ranging from 125 μM to 0.488 μM. For that, the unpurified designed Abs from crude media samples were captured directly on a protein-A sensor chip. Out of 17 cloned variants, 15 designed Abs either did not bind CA19-9 at all, or bound but displayed affinities that were weaker or similar to that of 1116NS19.9. Two designs termed Ablift2 and Ablift15 were detected as stronger binders compared to the WT Ab (multiple sequence alignment of these designs to the original sequence is presented in FIG. 20A and FIG. 20B). To measure the $K_d$, protein-A purified Abs were run on the SPR using 14-concentration series ranging from 500 μM to 0 in 2-fold dilutions.

Figure 6:
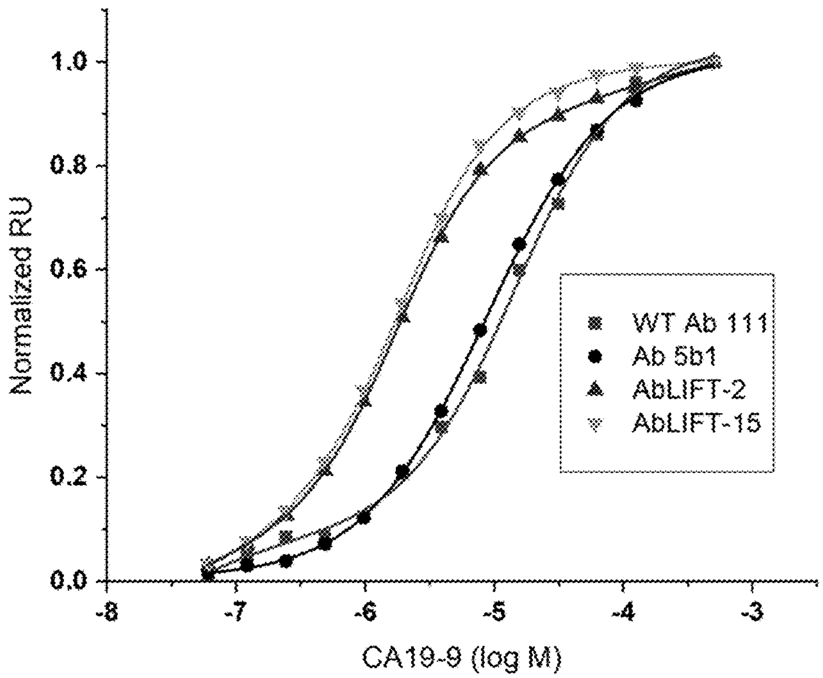
FIG. 6 shows a surface plasmon resonance (SPR) analysis for CA19-9 Ab binders. Single-cycle SPR was performed by capturing Abs on a protein-A chip and using monomeric CA19-9 as an analyte in a concentration range of 0 to 500 μM. Normalized capture values at steady-state were used to generate a binding curve. Fits were calculated using the origin program, and $K_d$ values measured as 14.7, 13, 1.8 and 1.7 μM for Abs 1116NS19.9, 5b1, Ablift2 and Ablift15, respectively.

$K_d$ values for Ablift2 and Ablift15 were subsequently determined from steady-state analyses as 1.81 μM and 1.69 μM respectively (FIG. 6). These $K_d$ values obtained are avidity free, i.e. obtained for Fab only since the CA19-9 used is in these experiments was monomeric, and hence they reflect the real affinities. The two improved designs show a ten-fold increase in affinity relative to the WT Ab 1116NS19.9 for which a $K_d$ of 14.7 μM was measured. As clearly follows from this example, even using precise structural data substantial inventive thinking was required to obtain designs that have higher affinity than the original Ab 1116NS19.9.

Example 5. Characterizing the Mode of Binding of the Improved Antibodies

To evaluate the mode of the improved binding of Ablift15, the Ab-CA19-9 interface was analyzed. For that, the Fabs of Ablift15 were produced and crystallized with CA19-9 as described above. Crystals diffracted to a resolution of 1.4 Å and data for the refined modal can be found in Table 3.

TABLE 3

Data collection and refinement statistics for holo Ab AbLIFT-15

| Parameter | Halo-AbLIFT-15 |
|---|---|
| Wavelength (Å) | 0.97371 |
| Space group | P $4_32_12$ |
| Cell dimensions | |
| a, b, c (Å) | 64.9 64.9 244.1 |
| α, β, γ ° | 90 90 90 |
| Resolution (Å) | 62.75-1.42 (1.471-1.42)[a] |
| $R_{meas}$ (%) | 10.85 (111.8)[a] |
| $R_{pim}$ | 4.3 (45.65)[a] |
| $CC_{1/2}$ | 99.6 (57.7)[a] |
| I/σI | 7.89 (1.14)[a] |
| Completeness (%) | 99.89 (99.6)[a] |
| Multiplicity | 6.1 (5.6)[a] |
| Reflections | 610565 |
| Unique reflections | 99646 |
| Resolution (Å) | 62.75-1.42 |
| No. of reflections | 99619 |
| $R_{work}/R_{free}$ (%) | 14.60/18.39 |
| Refinement | |
| No. of atoms | |
| Protein | 3305 |
| Ligand/ion | 68 |
| Water | 660 |
| B factors | |
| Protein | 20.14 |
| Ligand/ion | 24.62 |
| Water | 34.32 |
| Ramachandran | |
| Favored (%) | 98.35 |
| Allowed (%) | 1.65 |
| Outlier (%) | 0.0 |
| Root mean square deviations | |
| Bond length (Å) | 0.010 |
| Bond angles ° | 1.4 |

[a]Values in parentheses are for the highest resolution-shell

Comparing WT Ab 1116NS19.9 to Ablift15 by superimposing the structures shows that the binding region of CA19-9 was indeed preserved in Ablift15, as well as the overall structure, manifested by an RMSD of 0.22 Å for 220 Cα atoms of the variable regions. The structure of Ablift15 illuminates the mechanisms by which the various mutations stabilized the Ab. Zooming in on the mutated regions of the light chain, it was found that Y87W and F98W alterations result with tighter packing by tryptophan providing a more optimal space filler. S43P and D56P are both found on loops for which proline residues can contribute to a rigidifying effect (the numbering is according to KABAT). For the heavy chain, it is not clear how T93A and T94V contribute to stabilization, taking into account that Thr93 contributes to a hydrogen bond that no longer exists when replaced with alanine. As for Y98F, the missing hydroxyl in phenylalanine which does not engage in a bond can provide extra flexibility to the residue. In total, these seven core mutations retain the WT structure along with superior affinity.

Example 6. Functional Characterization of scFv-Ablift (Ablift15)

Materials and Methods

Cloning of Ablift Antibodies into Yeast Surface Display (YSD) System

To obtain yeast cells with surface expression of Ablift15 scFv fragments, Corresponding scFv fragments with flanking regions homologous to pETCON2 VH/VL plasmids were synthesized (Integrated DNA Technologies Inc.; IDT, Israel), then cloned into YSD system as described above for RA9 and 5B1.

Ablift scFv-YSD antibodies were cloned into YSD system as described above for RA9 and 5B1.

Ablift scFv-YSD clones specificity was measured as described above for RA9 and 5B1 scFv-YSD, with glycan antigens at concentration of 0.5 μM.

Measurement of Apparent $K_D$ of scFv-Ablift-YSD

Cloned scFv-Ablift15-YSD were induced to express surface expression of scFv, then examined by FACS against serial dilutions of antigen, and apparent $K_D$ calculated from saturation curves. scFv-Ablift15-YSD cells were cultured in SD-Trp at 30° C., passaged 1:10 each day for three days, then scFv expressed by replacing to SG-Trp media at 20° C. for overnight growth. For staining, $5\times10^6$ scFv-Ablift15-YSD induced cells were washed with 1 ml assay buffer (PBS, 0.5% ovalbumin) then incubated at ten serial dilutions of $SLe^a$-PAA-biotin antigen ranging at 3333-0.16 nM with 1:50 diluted mouse-anti-c-Myc (4 μg/ml), both in assay buffer for 1 h at RT with rotation. Cells were washed with 1 ml ice cold assay buffer, then incubated for 40 min on ice with APC-streptavidin and Alexa-Fluor-488-goat-anti-mouse IgG1 diluted 1:50 (10 μg/ml) and 1:200 (10 μg/ml) respectively in assay buffer. Cells were washed with 1 mL ice cold PBS, then resuspended in 500 μl PBS. Fluorescence was measured by CytoFLEX flow cytometry (Beckman Coulter) and analyzed with Kaluza analysis software. Cells expressing surface scFv were gated, and the geometric mean of antigen binding was calculated. Geometric mean was plotted versus antigen concentration and apparent $K_D$ calculated according to non-linear fit with one-site specific binding using GraphPad Prism 8.0, as described (Amon et al., 2020).

Ablift mutant clones were cloned as described above for human IgG1.

Antibody Specificity by ELISA

Specificity was examined by binding of full-length Ablift15 IgG antibody to various glycans by ELISA inhibition assay. 96-well plate was coated with $SLe^a$-PAA-biotin (GlycoTech) in triplicates at 0.25 μg/well overnight at 4° C. Wells were blocked with blocking buffer (PBS pH7.4, 1% ovalbumin). Ablift15 antibody at 0.16 μg/ml was pre-incubated with either specific or non-specific target antigens ($SLe^a$-PAA-biotin and $Le^a$-PAA-biotin or $SLe^x$-PAA-biotin glycans, respectively) at 300-0.3 nM in blocking buffer. Antibody-glycan mixtures were incubated at 4° C. for two hours. Blocking buffer was removed, and antibody-glycan mixtures added to respective wells at 100 μl/well in triplicates, then incubated for two hours at RT. Plates were washed three times with PBST (PBS pH 7.4, 0.1% Tween), then incubated for 1 h at RT with HRP-goat-anti-human IgG 0.11 μg/ml in PBS. After washing three times with PBST, wells were developed with 140 μl of O-phenylenediamine in 100 mM citrate-$PO_4$ buffer, pH 5.5, and the reaction stopped with 40 μl of $H_2SO_4$ (4 M). Absorbance was measured at 490 nm on SpectraMax M3 (Molecular Devices). Specific binding was defined by subtracting the background readings obtained with the secondary antibody only.

Sialoglycan Microarray Nanoprinting

Arrays were fabricated with NanoPrint LM-60 Microarray Printer (Arrayit) on epoxide-derivatized slides (Corning 40044) with 16 sub-array blocks on each slide. Glycoconjugates were distributed into one 384-well source plates using 4 replicate wells per sample and 8 μl per well (Versions 13.1). Each glycoconjugate (Table 4) was prepared at 100 μM in an optimized print buffer (300 mM phosphate buffer, pH 8.4). To monitor printing quality, replicate-wells of human IgG (80, 40, 20, 10, 5, 0.25 ng/μl in PBS+10% glycerol) and AlexaFlour-555-Hydraside (Invitrogen A20501MP, at 1 ng/μl in 178 mM phosphate buffer, pH 5.5) were used for each printing run. The arrays were printed with four 946MP3 pins (5 μm tip, 0.25 μl sample channel, ~100 μm spot diameter; Arrayit). Each block (subarray) has 20 spots/row, 20 columns with spot to spot spacing of 275 μm. The humidity level in the arraying chamber was maintained at about 70% during printing. Printed slides were left on arrayer deck over-night, allowing humidity to drop to ambient levels (40-45%). Next, slides were packed, vacuum-sealed and stored at RT until used.

TABLE 4

List of glycans printed on sialoglycan microarray

| Glycan ID | Structure |
|---|---|
| 1 | Neu5,9Ac2α3Galβ4GlcNAcβO(CH2)2CH2NH2 |
| 2 | Neu5Gc9Acα3Galβ4GlcNAcβO(CH2)2CH2NH2 |
| 3 | Neu5,9Ac2α6Galβ4GlcNAcβO(CH2)2CH2NH2 |
| 4 | Neu5Gc9Acα6Galβ4GlcNAcβO(CH2)2CH2NH2 |
| 5 | Neu5Acα6GalNAcαO(CH2)2CH2NH2 |
| 6 | Neu5Gcα6GalNAcαO(CH2)2CH2NH2 |
| 7 | Neu5,9Ac2α3Galβ3GlcNAcβO(CH2)2CH2NH2 |
| 8 | Neu5Gc9Acα3Galβ3GlcNAcβO(CH2)2CH2NH2 |
| 9 | Neu5,9Ac2α3Galβ3GalNAcαO(CH2)2CH2NH2 |
| 10 | Neu5Gc9Acα3Galβ3GalNAcαO(CH2)2CH2NH2 |
| 11 | Neu5Acα3Galβ4GlcNAcβO(CH2)2CH2NH2 |
| 12 | Neu5Gcα3Galβ4GlcNAcβO(CH2)2CH2NH2 |
| 13 | Neu5Acα3Galβ3GlcNAcβO(CH2)2CH2NH2 |
| 14 | Neu5Gcα3Galβ3GlcNAcβO(CH2)2CH2NH2 |
| 15 | Neu5Acα3Galβ3GalNAcαO(CH2)2CH2NH2 |
| 16 | Neu5Gcα3Galβ3GalNAcαO(CH2)2CH2NH2 |
| 17 | Neu5Acα6Galβ4GlcNAcβO(CH2)2CH2NH2 |
| 18 | Neu5Gcα6Galβ4GlcNAcβO(CH2)2CH2NH2 |
| 19 | Neu5Acα6Galβ4GlcβO(CH2)2CH2NH2 |
| 20 | Neu5Gcα6Galβ4GlcβO(CH2)2CH2NH2 |
| 21 | Neu5Acα3Galβ4GlcβO(CH2)2CH2NH2 |
| 22 | Neu5Gcα3Galβ4GlcβO(CH2)2CH2NH2 |
| 23 | Neu5,9Ac2α6GalNAcαO(CH2)2CH2NH2 |
| 24 | Neu5Gc9Acα6GalNAcαO(CH2)2CH2NH2 |
| 25 | Neu5Acα3GalβO(CH2)2CH2NH2 |
| 26 | Neu5Gcα3GalβO(CH2)2CH2NH2 |
| 27 | Neu5Acα6GalβO(CH2)2CH2NH2 |
| 28 | Neu5Gcα6GalβO(CH2)2CH2NH2 |
| 29 | Neu5,9Ac2α3GalβO(CH2)2CH2NH2 |
| 30 | Neu5Gc9Acα3GalβO(CH2)2CH2NH2 |

TABLE 4-continued

List of glycans printed on sialoglycan microarray

| Glycan ID | Structure |
|---|---|
| 31 | Neu5,9Ac2α6GalβO(CH2)2CH2NH2 |
| 32 | Neu5Gc9Acα6GalβO(CH2)2CH2NH2 |
| 33 | Neu5Acα3Galβ3GalNAcβO(CH2)2CH2NH2 |
| 34 | Neu5Gcα3Galβ3GalNAcβO(CH2)2CH2NH2 |
| 35 | Neu5,9Ac2α3Galβ3GalNAcβO(CH2)2CH2NH2 |
| 36 | Neu5Gc9Acα3Galβ3GalNAcβO(CH2)2CH2NH2 |
| 37 | Neu5,9Ac2α6Galβ4GlcβO(CH2)2CH2NH2 |
| 38 | Neu5Gc9Ac6Galβ4GlcβO(CH2)2CH2NH2 |
| 39 | Neu5,9Ac2α3Galβ4GlcβO(CH2)2CH2NH2 |
| 40 | Neu5Gc9Ac3Galβ4GlcβO(CH2)2CH2NH2 |
| 41 | Neu5Acα8Neu5Acα3Galβ4GlcβO(CH2)2CH2NH2 |
| 42 | Neu5Acα8Neu5Acα8Neu5Acα3Galβ4GlcβO(CH2)2CH2NH2 |
| 43 | Galβ4GlcβO(CH2)2CH2NH2 |
| 44 | Galβ4GlcβNH2 |
| 45 | Galβ4GlcNAcβO(CH2)2CH2NH2 |
| 51 | Galβ3GalNAcβO(CH2)2CH2NH2 |
| 52 | Galβ3GalNAcαO(CH2)2CH2NH2 |
| 53 | Galβ3GlcNAcβO(CH2)2CH2NH2 |
| 54 | Galβ4GlcNAc6SβO(CH2)2CH2NH2 |
| 55 | Neu5Acα3Galβ4(Fucα3)GlcNAcβO(CH2)2CH2NH2 |
| 56 | Neu5Gcα3Galβ4(Fucα3)GlcNAcβO(CH2)2CH2NH2 |
| 57 | Neu5Acα3Galβ4(Fucα3)GlcNAc6SβO(CH2)2CH2NH2 |
| 58 | Neu5Gcα3Galβ4(Fucα3)GlcNAc6SβO(CH2)2CH2NH2 |
| 59 | Galβ3GlcNAcβ3Galβ4GlcβO(CH2)2CH2NH2 |
| 60 | Neu5Acα3Galβ3GlcNAcβ3Galβ4GlcβO(CH2)2CH2NH2 |
| 61 | Neu5Gcα3Galβ3GlcNAcβ3Galβ4GlcβO(CH2)2CH2NH2 |
| 62 | Neu5Acα3Galβ4GlcNAc6SβO(CH2)2CH2NH2 |
| 63 | Neu5Gcα3Galβ4GlcNAc6SβO(CH2)2CH2NH2 |
| 64 | Neu5Acα8Neu5Acα3Galβ4GlcβO(CH2)3NHCOCH2(OCH2CH2)6NH2 |
| 65 | Neu5Acα8Neu5Acα8Neu5Acα3Galβ4GlcβO(CH2)3NHCOCH2(OCH2CH2)6NH2 |
| 66 | Neu5Acα6(Neu5Acα3)Galβ4GlcβO(CH2)2CH2NH2 |
| 67 | Neu5Acα6(Neu5Gcα3)Galβ4GlcβO(CH2)2CH2NH2 |
| 68 | Neu5Acα6(Kdnα3)Galβ4GlcβO(CH2)2CH2NH2 |
| 69 | Neu5Gcα8Neu5Acα3Galβ4GlcβO(CH2)2CH2NH2 |
| 70 | Kdnα8Neu5Acα3Galβ4GlcβO(CH2)2CH2NH2 |
| 71 | Neu5Acα8Kdnα6Galβ4GlcβO(CH2)2CH2NH2 |
| 72 | Neu5Acα8Neu5Gcα3Galβ4GlcβO(CH2)2CH2NH2 |
| 73 | Neu5Acα8Neu5Gcα6Galβ4GlcβO(CH2)2CH2NH2 |
| 74 | Kdnα8Neu5Gcα3Galβ4GlcβO(CH2)2CH2NH2 |
| 75 | Neu5Gcα8Neu5Gcα3Galβ4GlcβO(CH2)2CH2NH2 |
| 76 | Neu5Acα8Neu5Acα6Galβ4GlcβO(CH2)2CH2NH2 |
| 77 | Neu5GcMeα8Neu5Acα3Galβ4GlcβO(CH2)2CH2NH2 |
| 78 | Galα3Galβ4GlcNAcβO(CH2)2CH2NH2 |
| 79 | Galβ3GalNAcαO(CH2)2CH2NH2 |
| 80 | Galβ4(Fucα3)GlcNAcβO(CH2)2CH2NH2 (Galβ4GlcNAc(Fucα3)β3GalβProNH2) |
| 81 | Neu5Acα8Neu5Acα3Galβ4GlcO(CH2)2CH2NH2 (GD3) |
| 82 | Neu5Acα8Neu5Acα3(GalNAcβ4)Galβ4GlcO(CH2)2CH2NH2 (GD2) |
| 83 | Neu5Ac-α2,3-Galβ3GlcNAc(Fucα4)β3GalβProNH2 |
| 84 | Galβ3GlcNAc(Fucα4)β3GalβProNH2 |
| 85 | Gal(Fucα2)β3GlcNAc(Fucα4)β3GalβProNH2 |
| 86 | Neu5Gc-α2,3-Galβ3GlcNAc(Fucα4)β3GalβProNH2 |
| 87 | Neu5,9Ac2-α2,3-Galβ3GlcNAc(Fucα4)β3GalβProNH2 |
| 88 | Neu9Ac5Gc-α2,3-Galβ3GlcNAc(Fucα4)β3GalβProNH2 |

Sialoglycan Microarray Binding Assay

Slides were developed and analyzed as previously described (Padler-Karavani et al., 2012, *J Biol Chem,* 287: 22593-22608), with some modifications. Slides were rehydrated with $dH_2O$ and incubated for 30 min in a staining dish with 50° C. pre-warmed ethanolamine (0.05 M) in Tris-HCl (0.1 M, pH 9.0) to block the remaining reactive epoxy groups on the slide surface, then washed with 50° C. pre-warmed $dH_2O$. Slides were centrifuged at 200×g for 5 min then fitted with ProPlateTM Multi-Array 16-well slide module (Invitrogen) to divide into the sub-arrays (blocks). Slides were washed with PBST (0.1% Tween 20), aspirated, and blocked with 200 μL/sub-array of blocking buffer (PBS/OVA, 1% w/v ovalbumin, in PBS, pH 7.3) for 1 h at RT with gentle shaking. Next, the blocking solution was aspirated and 100 μL/block of purified antibodies in $1.92\times10^{-2}$-$4.81\times10^{-3}$ μg/mL diluted in PBS/OVA were incubated with gentle shaking for 2 h at RT. Slides were washed four times with PBST, then with PBS for 2 min. Bound antibodies were detected by incubating with secondary detection diluted in PBS, 200 μL/block at RT for 1 h, Cy3-anti-human IgG 0.4 μg/mL (Jackson ImmunoResearch). Slides were washed four times with PBST then with PBS for 10 min followed by removal from ProPlate™ Multi-Array slide module and immediately dipping in a staining dish with $dH_2O$ for 10 min with shaking, then centrifuged at 200×g for 5 min. Dry slides immediately scanned.

Array Slide Processing

Processed slides were scanned and analyzed as described (Padler-Karavani et al., 2012) at 10 μm resolution with a GenePix 4000B microarray scanner (Molecular Devices) using 350 gain. Image analysis was carried out with GenePix Pro 6.0 analysis software (Molecular Devices). Spots were defined as circular features with a variable radius as determined by the GenePix scanning software. Local background subtraction was performed.

Cancer Cells Binding Assays

WiDr cells were obtained from American Type Culture collection (ATCC), cells were grown in Dulbecco's Modified Eagle Medium (DMEM; biological industries) supplemented with 10% heat inactivated fetal bovine serum (FBS), 2 mM L-glutamine, 100 units/ml penicillin and 0.1 mg/ml streptomycin. For binding assays, cells were collected from plates using 10 mM EDTA. $4\times10^5$ cells were incubated with 10-0.156 ng/μl of cloned full-length Native or Ablift15 IgGs diluted in FACS buffer (PBS with 0.5% fish gelatin) for 1 h on ice, followed by incubation with Cy3-AffiniPure goat-anti-human IgG diluted 1:100 (15 μg/ml) in FACS buffer for 40 min on ice. Fluorescence was measured by CytoFLEX flow cytometry. To confirm cancer cells binding specificity, sialidase FACS assay was performed, in which WiDr cells were collected from plates using 10 mM EDTA. $2\times10^5$ cells were divided into Eppendorf tubes and incubated for four hours at 37° C. with either PBS, 100 mU active *Arthrobacter ureafaciens* Sialidase (AUS) (EY Laboratories, San Mateo, CA, USA) or 100 mU inactive AUS (pre-incubated in 90° C. for 30 min) in PBS. Then, cells were washed with FACS buffer, stained with 1 μg/ml Ablift15 full-length IgG antibodies, followed by washing, secondary antibody labeling and fluorescence measurement, as described above.

Antibodies In Vivo Cytotoxicity Against Cancer Cells

Nude mice were obtained from Envigo and experiment conducted according to Animal Care and Use Committee protocol approved by Tel Aviv University. $2\times10^6$ WiDr cells in 100 μl were injected subcutaneously in the right flank of 15 nude mice. Five days post injection, mice were immunized intraperitoneally (i.p.) with 15 μg/g of either Native or Ablift15 IgG antibodies, or PBS only as a control, in total volume of 500 μl. Tumor volume was monitored and measured with caliper every 2-3 days, mice were sacrificed 21 days after tumor inoculation.

Statistical Analysis

Statistical analysis conducted with Prism 8 with the specific methods as indicated in figure legends.

Results

Figure 7A:
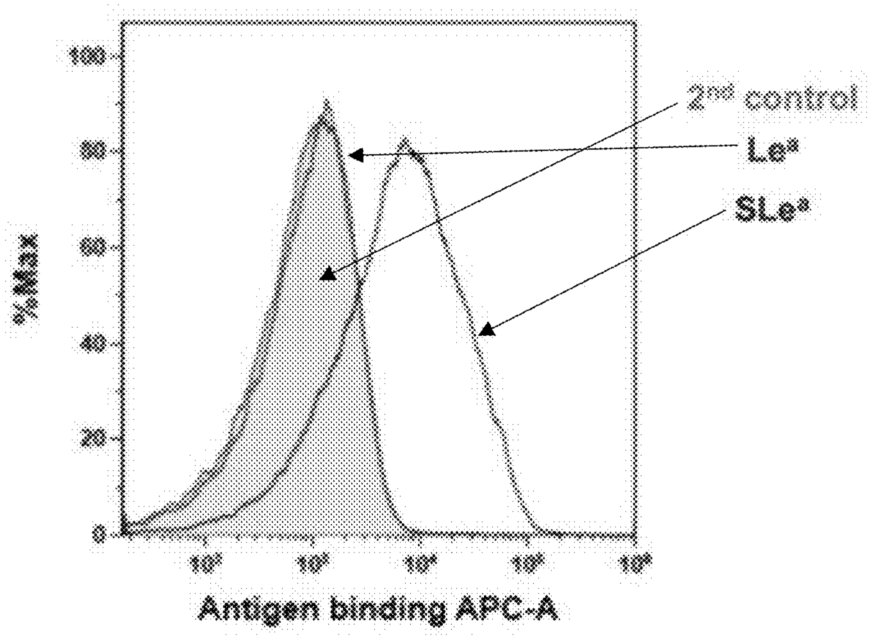
FIG. 7A shows specificity of scFv-Ablift-YSD yeast cells as measured against either 0.5 μM $SLe^a$-PAA-biotin, 0.5 μM $Le^a$-PAA-biotin, or FACS buffer as a negative control.
Figure 7B:
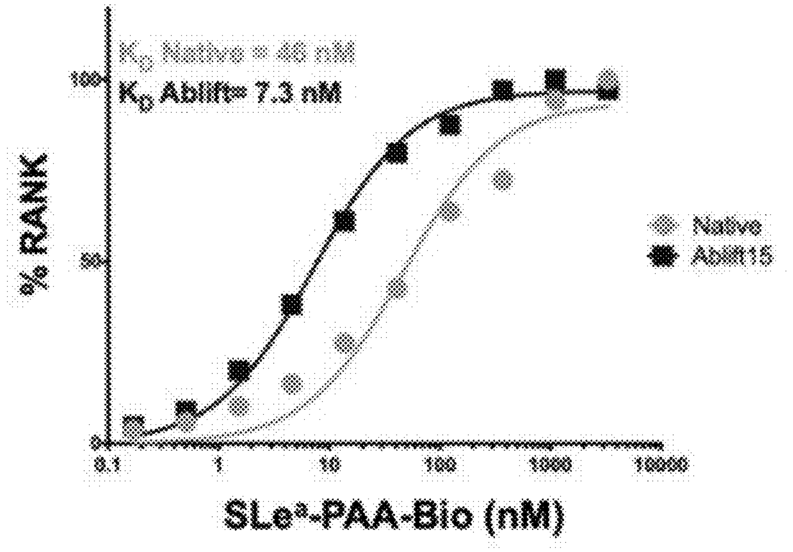
FIG. 7B shows apparent $K_D$ of scFv-Ablift-YSD and scFv-Native-YSD yeast cells that were examined at 10 serial dilutions of $SLe^a$-PAA-biotin (3333-0.16 nM). Cells were gated on scFv-expressing cells and geometric mean fluorescence intensity of antigen binding measured. $K_D$ was calculated according to non-linear fit with one-site specific binding using GraphPad Prism 8.0. Representative of two independent experiments.

The scFv fragment of Ablift15 was cloned into YSD system, then cells were induced to express surface scFv, and binding to antigens examined by FACS. Ablift15 yeast variants showed strong binding to the specific $SLe^a$ antigen, while no binding at all to the non-specific $Le^a$ antigen that lacks terminal sialic acid, similar to the negative control staining (FIG. 7A). To further evaluate binding affinity, the apparent $K_D$ values of scFv-yeast cells were measured by binding saturation curves against increasing nanoparticle antigen concentrations (ten serial dilutions ranging 3333-0.16 nM) revealing much higher affinity in scFv-Ablift15 mutant compared to the scFv-Native clone (FIG. 7B).

Figure 8:
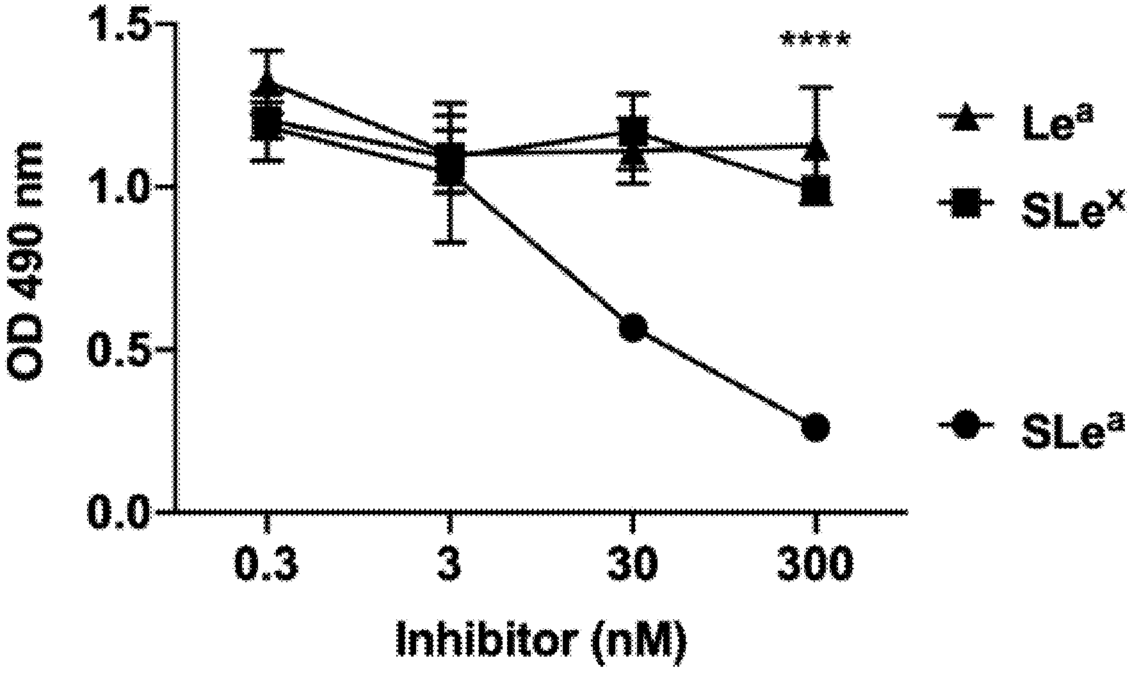
FIG. 8 shows the specificity of Ablift IgG (Ablift15) antibody by ELISA inhibition assay. Specificity of the full-length Ablift15 IgG was examined by ELISA inhibition assay against coated $SLe^a$-PAA-biotin, after pre-incubation of the antibody with specific ($SLe^a$) or non-specific glycans ($SLe^x$ and $Le^a$). 2-way ANOVA ****p<0.001.

The scFv fragments were next cloned and expressed as full-length IgG antibodies (Wrammert et al., Nature, 2008, 453, 667-671) for further characterization of their potency in terms of specificity, cancer cell binding and cytotoxicity using an IgG1 scaffold as in Examples 1-5. Gibson assembly was used to clone the VH and VL variable regions into corresponding p3BNC vectors that carry the constant regions. For each antibody variable fragment (heavy and light), a separate vector containing a suitable constant region of hIgG1 or human kappa light chain was used. 293A cells (a sub clone of the human embryonic kidney cell line) were transfected with the plasmids and full-length antibodies purified by Protein-A through binding to antibody Fc region. Functional properties were then carefully analyzed by FACS, ELISA and by the powerful glycan microarray technology (Karavani et al., 2012). The cloned full length antibody was tested by ELISA inhibition assay, in which binding of Ablift15 IgG to $SLe^a$ was inhibited only with the specific glycan $SLe^a$, but not with the closely-related glycans $SLe^x$ or $Le^a$, demonstrating the specificity of this mutant clone (FIG. 8).

Figure 15A:
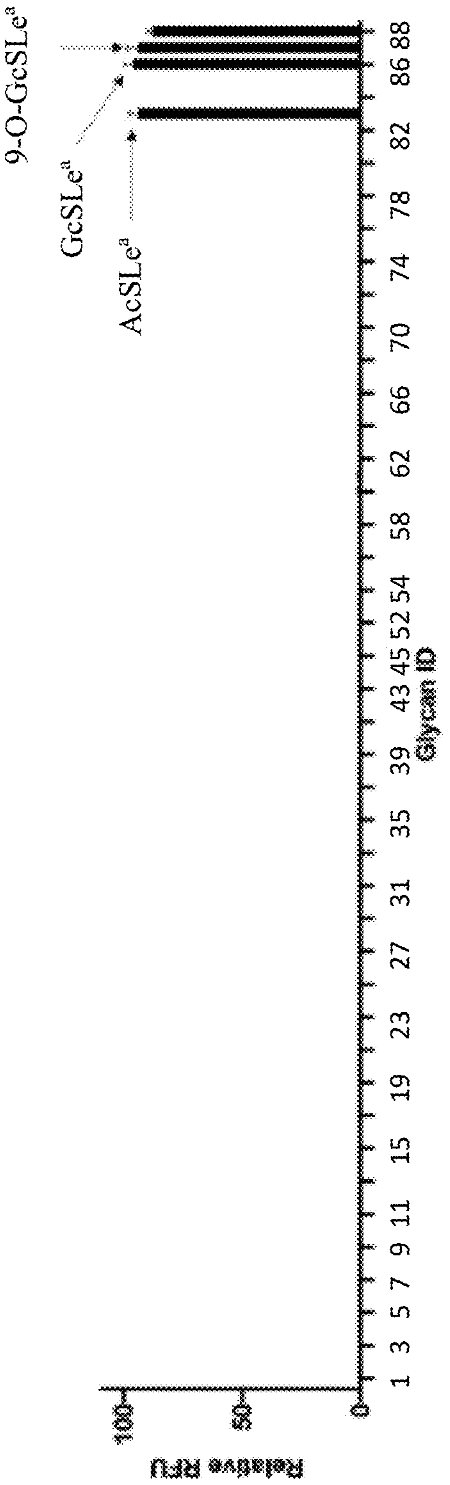
FIG. 15A shows the specificity of cloned Ablift15 IgG antibody against multiple glycan antigens.

The nano-printed glycan microarrays were used to further examine the specificity of Ablift15 IgG in a more detailed high-throughput assay against 88 different glycans, containing non-sialylated glycans or sialylated glycans that contain different types of sialic acids, including Neu5Ac (Ac), its hydroxylated form Neu5Gc (Gc) and their 9-O-acetylated derivatives (9-O-Ac/9-O-Gc) (Table 4). Array analysis of Ablift15 IgG showed that it is highly specific to $AcSLe^a$ (glycan #83), $GcSLe^a$ (glycan #86) and their corresponding 9-O-acetylated derivatives (glycan #87 and #88, respectively) (FIG. 15A). In fact, both $Le^a$ (glycan #84) and non-fucosylated-$SLe^a$ (glycan #13; Neu5Acα2-3Galβ1-3GlcNAcβProNH2) showed no binding at all, demonstrating the importance of the sialic acid and fucose residues for antibody recognition.

Figure 9:
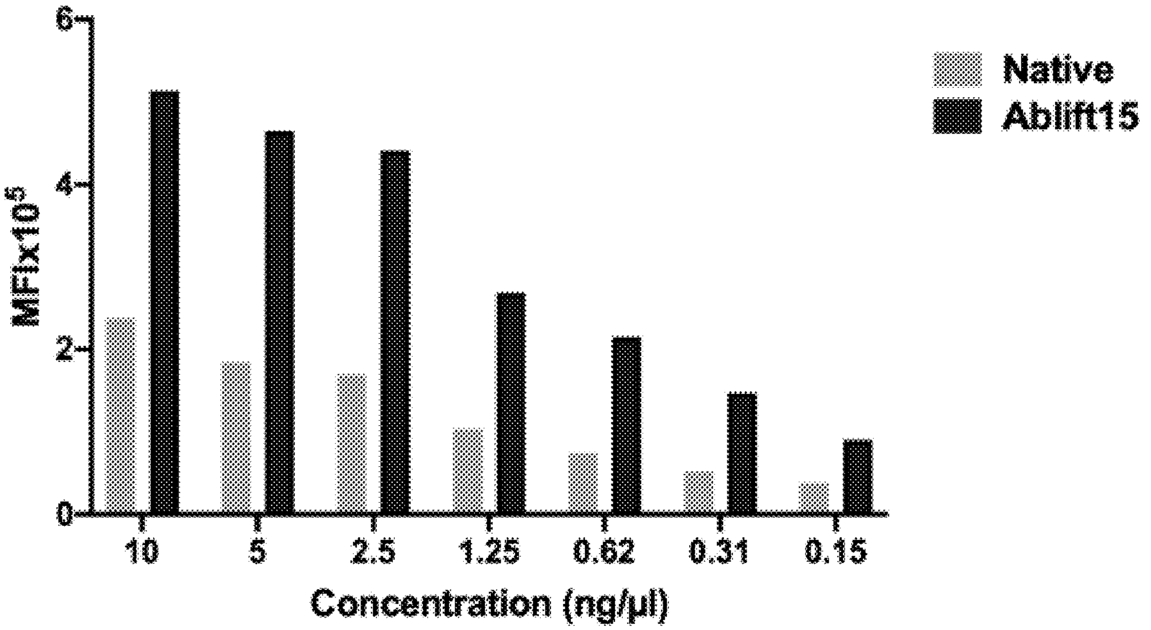
FIG. 9 shows antibody binding to antigen-expressing cancer cells. The binding of Native and Ablift15 IgG antibodies was examined by FACS against WiDr colorectal cancer cells that express $SLe^a$ at various dilutions (10-0.15 ng/μl) demonstrating superior binding of Ablift15 compared to Native IgG.
Figure 10A:
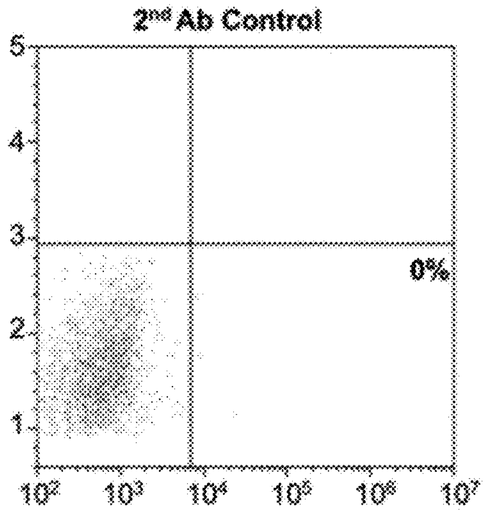
FIG. 10 shows sialoglycan specificity of Ablift15 IgG antibody binding to cancer cells. Specificity of binding to cells was demonstrated by treatment of cells with *Arthrobacter ureafaciens* Sialidase (AUS) (FIG. 10D) that abrogated binding of Ablift15 IgG to $SLe^a$-expressing WiDr cells, in comparison to control (FIG. 10A), direct binding of the antibody (FIG. 10B) or its binding to cells treated with heat-inactivated AUS (FIG. 10C).
Figure 10B:
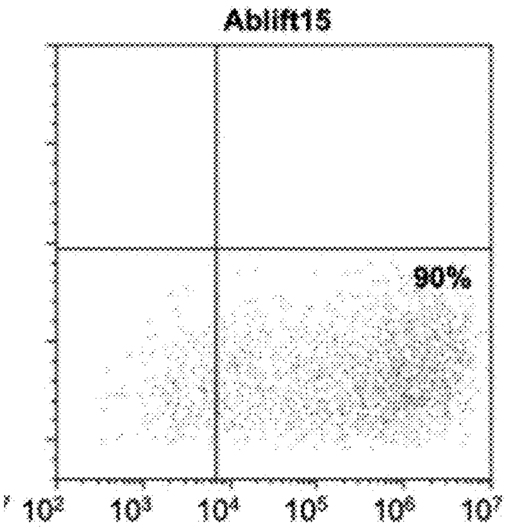
Figure 10C:
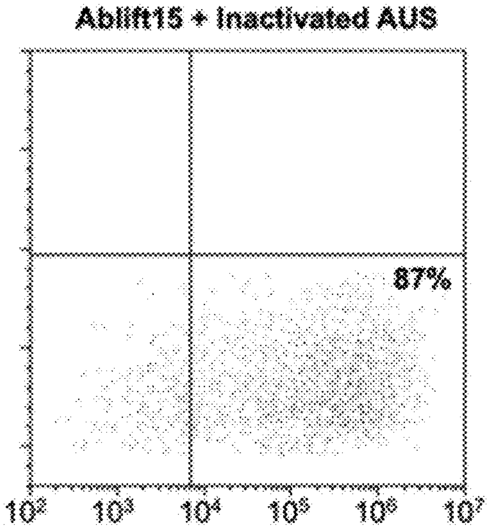
Figure 10D:
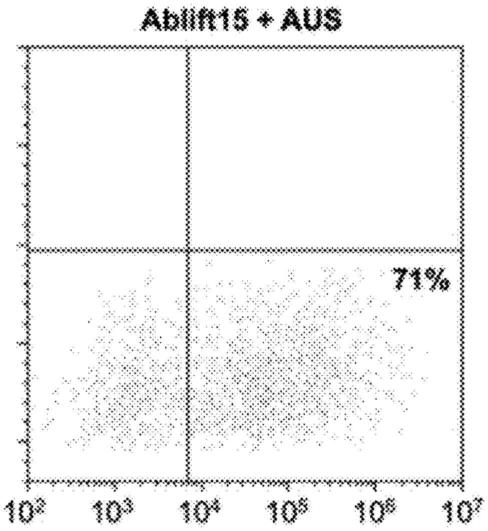

The potential of antibodies to be used in cancer therapeutic settings, generally requires recognition of the target antigen in the natural context of cancer cells. Therefore, the binding of Ablift15 IgG clone to cancer cells is assessed in comparison to the wild-type (native) antibody. Ablift15 IgG clone showed higher binding efficiency compared to the Native IgG, at all the examined concentrations (FIG. 9). Ablift15 IgG binding to these cancer cells was highly specific against the sialoglycan antigen, also in the natural context, since the binding was dramatically reduced after removal of sialic acids from the cell surface by a sialidase treatment (FIG. 10).

Figure 11:
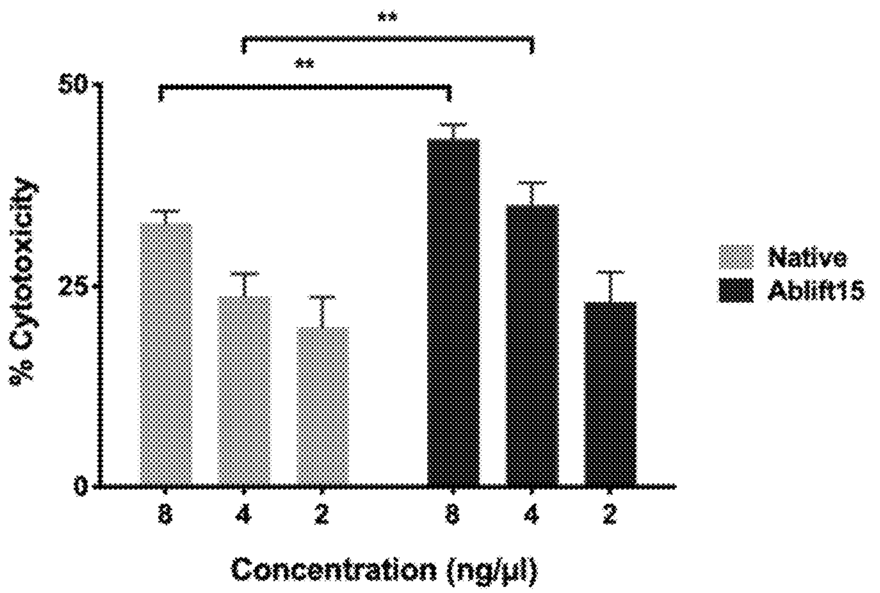
FIG. 11 shows antibodies in vitro cytotoxicity against cancer cells. Complement-dependent cytotoxicity (CDC) of Native versus Ablift15 IgGs was examined. WiDr target cells were incubated with antibodies at 8 ng/μl, 4 ng/μl or 2 ng/μl concentrations, then rabbit complement was added. Cytotoxicity was determined by LDH detection kit (mean±SD; representative of two independent experiments; 2-way ANOVA, **, P<0.01).

In order to test whether this improved cancer cell binding is also reflected in improved cancer cell killing, e.g. by complement recruitment, complement-dependent cytotoxicity (CDC) was evaluated. Ablift15 IgG shows higher cytotoxicity of WiDr cancer cells compared to the Native clone (FIG. 11). These data show that the Ablift15 IgG clone seem to have superior functionality over the Native IgG clone at in vitro settings.

To further evaluate the therapeutic potential of Ablift15 antibodies also in vivo, immuno-deficient nude mice are subcutaneously inoculated with WiDr cells. Five days later, mice are i.p.—treated with 15 μg/g, and tumor volumes recorded until day 21 post inoculation.

Example 7. Humanization of mAblift15 Antibodies with Functional Reactivity and Reduced Immunogenicity Material and Methods Humanization of Ablift15

Figure 12A:
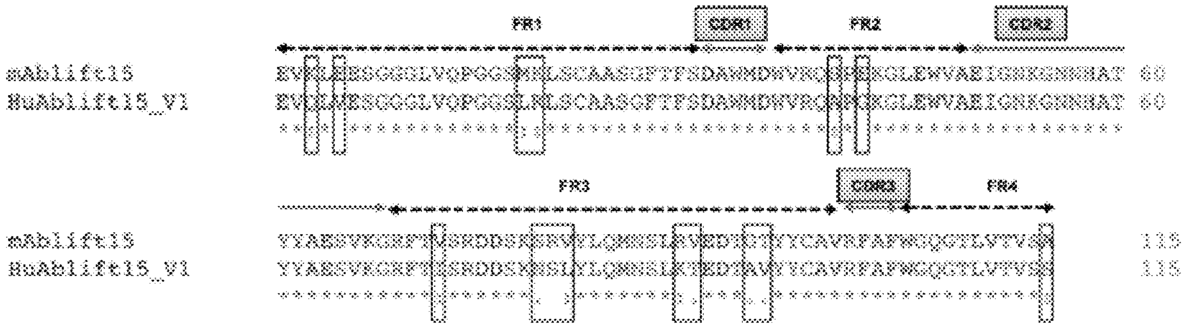
FIG. 12A shows MSA for Ablift 15 VH and HuAblift15: V1.
Figure 12B:
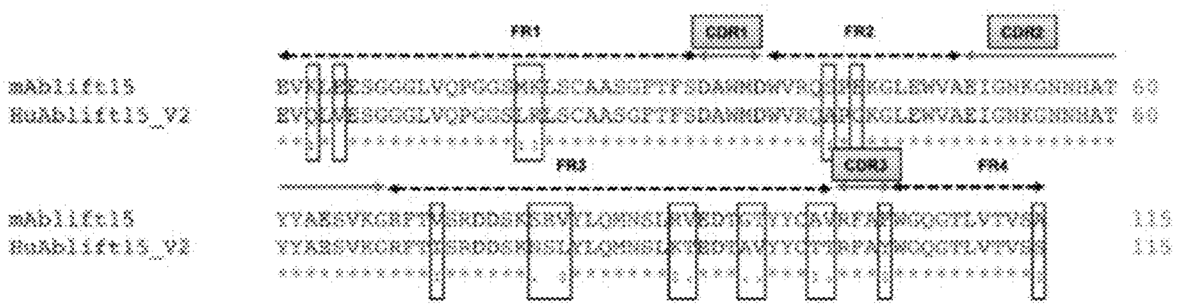
FIG. 12B shows MSA for Ablift 15 VH and HuAblift15: V2.
Figure 12C:
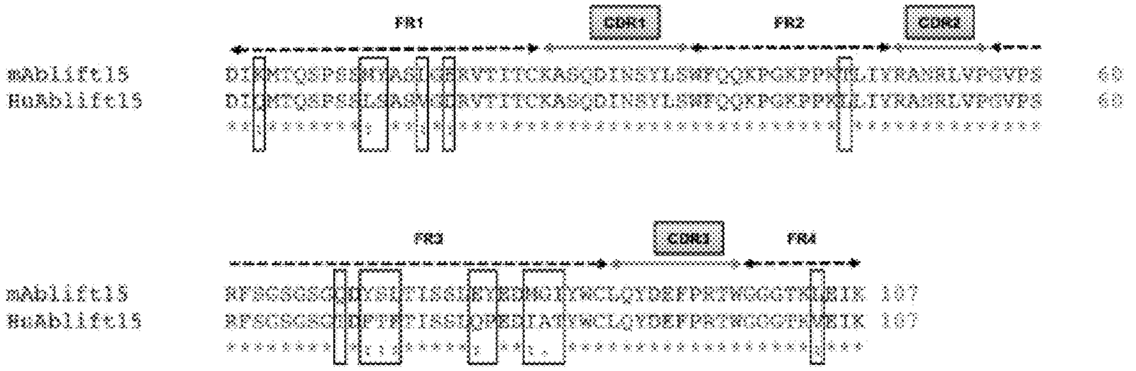
FIG. 12C shows MSA for Ablift 15 VL and HuAblift15: VL.

The DNA sequences of the variable heavy (VH) and the variable light (VL) regions of the mouse-derived Ablift15 antibody (mAblift15) were compared to human germline sequences in the human immunoglobulin database by the IgBlast tool (https://www.ncbi.nlm.nih.gov/igblast/), resulting in the best fit for VH to IGHV3-72*01 (65.9% identity), and for VL to IGKV1-33*01 (65.9% identity), that served as the basis for antibodies humanization. This germline sequences database does not cover the framework 4 (FR4) regions, therefore the present inventors screened the IGHJ sequences in IMGT database (http://www.imgt.org/) for common human VH FR4 with sequence similarity to the VH FR4 of mAblift15 antibody. Out of the three different alleles of the highest sequence similarity, IGHJ4*01 sequence was selected as the basis for VH FR4 humanization. For VL FR4 similarity analysis of mAblift15 antibody, IMGT database revealed two different alleles with the highest sequence similarity, IGKJ4*01 sequence was selected as the basis for VL FR4 humanization. For VH humanization, two variants were generated, one variant maintained the three mutations that occurred in mAblift15 VH compared to mNative VH and termed HuAblift15 VH V1: 93H, 94H, 98H (according to KABAT) (FIG. 12A). Another variant was designed without the aforementioned three mutation and termed HuAblift15 VH V2 (FIG. 12B). Regarding VL humanization FR sequences were mostly mutated based on the selected germline sequences, while two mutations occurred in FR of mAblift15 VL were maintained. CDRs were preserved based on the mAblift15 VL sequences (FIG. 12C). Both HuAblift15 VH variants were paired with HuAblift15 VL to form the HuAblift15 V1 and HuAblift15 V2.

Expression of HuAblift15 Single-Chain Fv (scFv) Fragments on Yeast Cells

To obtain yeast cells with surface expression of the humanized antibody clones, the single-chain Fv (scFv) fragments of HuAblift15 V1 and HuAblift15 V2 were cloned into the YSD pETCON2-based system. Corresponding scFv fragments with flanking regions homologous to pETCON2 VH/VL plasmids were synthesized (Integrated DNA Technologies Inc.; IDT, Israel), then cloned into YSD system as described above.

Apparent $K_D$ of of Humanized and Mouse scFv-Ablift15 was Done as Explained Above Specificity of Ablift15-YSD Variants was Measured as Described Above for Ablift15

Immunogenicity Analysis of scFv-Ablift15

Immunogenicity of humanized antibody clones was evaluated by analysis of scFv recognition by pooled human IgG obtained from thousands of human donors (IVIg; Gamma Gard). For this purpose, IVIg was first pre-cleared from anti-yeast reactivity by serial incubations with yeast cells, then binding to scFv-expressing yeast cells was examined. Uninduced HuNative yeasts cells grown in SD-Trp at 30° C. were divided into 9 different Eppendorf tubes with $5\times10^6$ cells in each. Cells were washed twice with 1 ml PBS, then supernatant was removed. For anti-yeast adsorption, yeast cells in the first tube were resuspended in 1 ml of 68 mg/ml IVIg, followed by 10 min with rotation of 30 rpm at RT. Yeast-IVIg mixture was centrifuged at 10,000×g for 1 min, and supernatant with unbound antibodies was transferred into a fresh yeast pellet tube for a second cycle of antibody adsorption as described, and this was repeated for a total of nine incubations, thus decreasing the amount of anti-yeast antibodies in the IVIg resulting in a "yeast-purified IVIg" pooled human IgG. Subsequently, Humanized and mouse Ablift15-scFv yeast variants were induced to express scFv as indicated (by transfer to SG-Trp media at 20° C.), then $5\times10^6$ yeast cells were washed with 1 ml assay buffer (PBS, 0.5% ovalbumin), then incubated with 50 ng/μl yeast-purified IVIg in assay buffer for 45 min at RT with rotation. Cells were washed with 1 ml ice cold assay buffer, then incubated for 45 min on ice with 1:50 diluted mouse-anti-c-Myc in assay buffer (4 μg/ml). Cells were washed with 1 ml ice cold assay buffer, then incubated for 40 min with Cy3-anti-human Fc specific and Alexa-Fluor-488-goat-anti-mouse IgG1 diluted 1:100 (15 μg/ml) and 1:200 (10 μg/ml) respectively in assay buffer. Cells were washed with 1 ml ice cold PBS, then resuspended in 500 μl PBS for flow cytometry analysis.

Gibson assembly of full length humanized Ablift15 antibodies expression plasmids was performed as described above for RA9 using primers having nucleic acid sequences SEQ ID NOs: 54-67.

Expression and purification of full-length HuAblift15 IgG antibodies, sialoglycan microarray nanoprinting, sialoglycan microarray binding assay, array slide processing, binding of full-length HuAblift15 IgG antibodies to cancer cells, and antibody specificity measurement by ELISA were all done as described above.

Statistical Analysis

Statistical analysis was conducted with Prism 8 with the specific methods as indicated in the figure legends.

Results

Humanization of mAblift15 Antibodies

To reduce immunogenicity of the mAblift15, mutations were introduced based on DNA sequence homology with human germline antibodies, to generate their humanized versions (HuAblift15). Initially, the FR and CDRs of mAblift15 were identified according to Kabat and these were compared to the database of human germline antibodies sequences, and those of the highest homology were selected for design of antibody humanization. In the mAblift15 antibody a total of 31 mutations were introduced to get the HuAblift15 VI antibody clone, including 15 mutations in VH region and 16 mutations in the VL region. Alternatively, 34 mutations were introduced to get the HuAblift15 V2 antibody clone, including 18 mutations in VH region and 16 mutations in the VL region. These mutations were introduced particularly in the FR regions while maintaining the CDRs sequences of Ablift 15. To allow stabilization of the CDRs, in some cases, the FR amino acids closest to the CDRs in the mouse-derived clones were preserved also in the humanized antibodies, despite the fact that these were different in the homologous germline sequences (VH: FR2 'A' alanine that precedes CDR2; VH: FR3 'V' valine that precedes CDR3 in HuAblift15 V1; VH: FR3 'TT' two threonine that precedes CDR3 in HuAblift15 V2; VL: FR2 'WF' tryptophan-phenylalanine that are found right after CDR1). Germline Ig database does not cover the FR4 region, hence the IGHJ sequences of mAblift15 were screened for homology in IMGT human monoclonal database (http://www.imgt.org/) for common human VH FR4 with sequence similarity. Of this screening, the VH sequence of IGHJ4*01, and VL sequence of IGKJ4*01 were selected as the basis for humanization mutations selection. Of note, the mAblift15 clone VH sequence differs from mNative VH by a total of 3 mutations (2 in FR3, 1 in CDR3). In HuAblift15 V1 the present inventors maintained all these 3 mutations occurred in mAblift15 VH, while in HuAblift15 V2 the three mutations in the mAblift15 clone VH was reverted back to that found in the mNative (VH 'AV' alanine and valine to VH 'TT' two threonine; and VH 'F' phenylalanine VH 'F' to VH 'Y' tyrosine FIG. 12A).

Characterization of HuAblift15 Antibodies

Figure 13A:
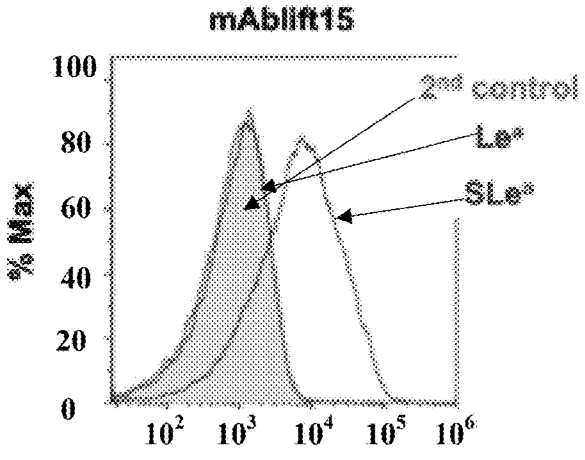
FIG. 13 shows the binding of mouse and humanized-Ablift15 variants to their specific antigen ($SLe^a$) or to a non-specific antigen ($Le^a$) as examined by FACS. For this purpose, yeast cells with surface expression of scFv fragments of mouse and humanized-Ablift15 were incubated with either 0.5 μM $SLe^a$-PAA-Biotin, 0.5 μM $Le^a$-PAA-Biotin or FACS buffer for negative control, then antibody binding was detected with secondary detection APC-streptavidin, and measured by CytoFLEX flow cytometry.
Figure 13B:
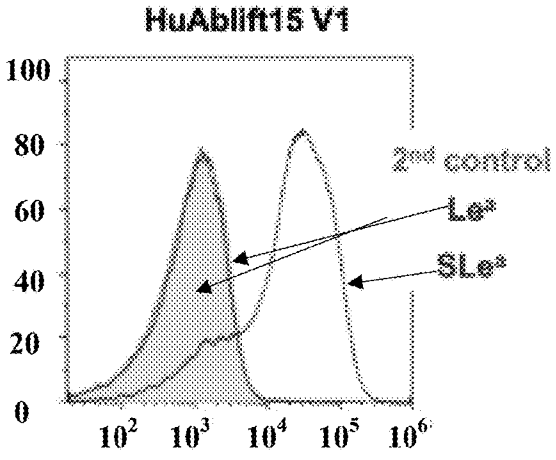
Figure 13C:
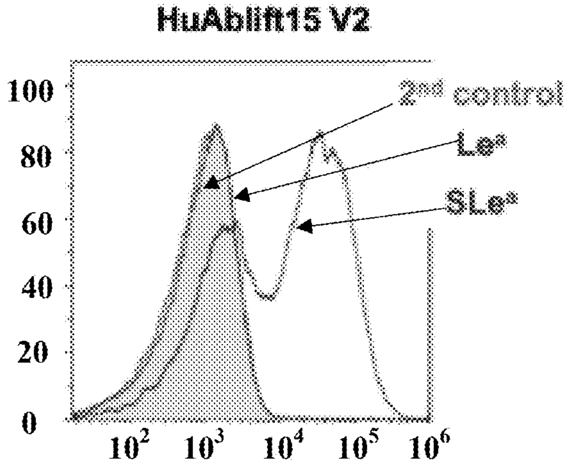
Figure 14:
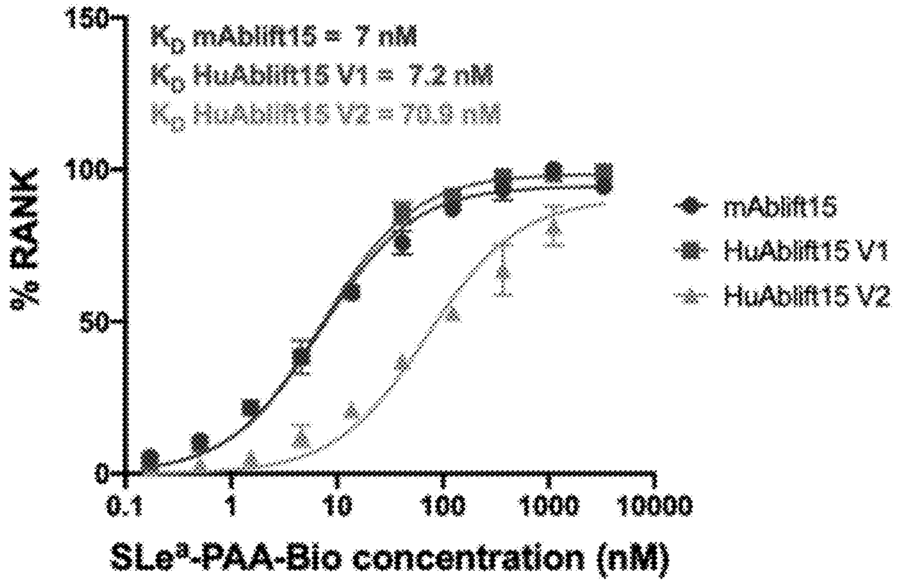
FIG. 14 shows the binding capacity and calculated affinities of mouse-derived and humanized scFv fragments (mAblift15, HuAblift15 V1, and HuAblift15 V2) as expressed on yeast cell. Binding of scFv clones to antigen was examined at 10 serial dilutions of $SLe^a$-PAA-Biotin (3333-0.16 nM). Cells were gated on scFv expressing cells and geometric mean fluorescence intensity of antigen binding measured. $K_D$ was calculated according to non-linear fit with one-site specific binding using GraphPad Prism 8.0. Average of two independent experiments (mean±SEM).

To characterize the properties of the humanized antibodies, the scFv fragments of mAblift15, HuAblift15-V1 and HuAblift15-V2 were each cloned into yeast surface display system (YSD), followed by induction of their expression on the surface of these yeast cells, then binding to antigens examined by FACS. All scFv-Ablift15 yeast variants showed strong binding to the specific antigen $SLe^a$ antigen, while no binding at all to the non-specific $Le^a$ antigen that lacks terminal sialic acid similar to the negative control staining (FIG. 13). To further evaluate the affinity of humanized scFvs, their binding was examined by FACS against serially diluted antigen concentrations. Affinity of scFv expressed on yeast cells was then calculated from binding over the range of antigen titration and apparent $K_D$ (affinity) was calculated from saturation curves (FIG. 14), according to non-linear fit with one-site specific binding using GraphPad Prism 8.0. Interestingly, the affinities of scFv-HuAblift15-V1 and scFv-mAblift15 were similar, while scFv-HuAblift15-V2 has lower affinity in an order of magnitude.

Figure 15B:
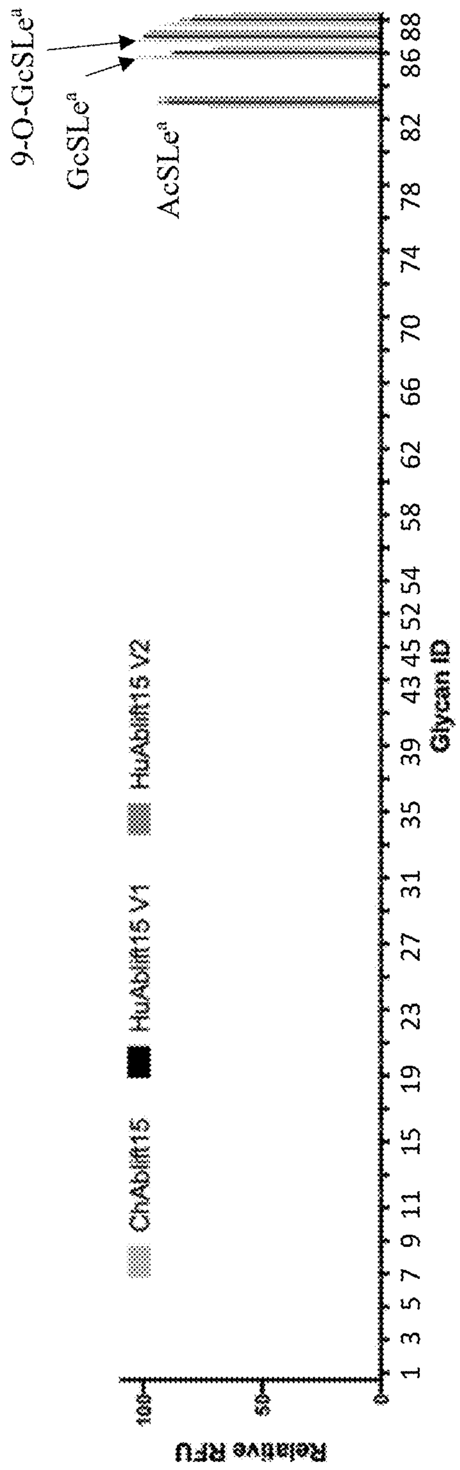
FIG. 15B shows binding of Ablift15 full-length antibodies humanized and chimeric IgGs against diverse glycans (HuAblift15 V1-hIgG and HuAblift15 V2-hIgG labeled here as HuAblift15 V1 and HuAblift15 V2, respectively; mAblift15-hIgG labeled here as ChAblift15). List of glycans in Table 4. Relative fluorescence units (RFU) were calculated as a percentage of maximal binding at each concentration, followed by averaging the relative RFU rank of the three tested antibody concentrations for each glycan (mean±SEM). Representative of two independent experiments.

To further characterize the humanized variants, VH and VL sequences were cloned into full length human IgG p3BNC expression vectors by Gibson assembly (HuAblift15 V1-hIgG and HuAblift15 V2-hlgG). Similarly, VH and VL sequences of the mouse-derived antibodies were clone into same expression vectors to form chimeric antibodies (mAblift15-hIgG; also referred as ChAblift15) Full length antibodies were produced by transfection of HEK-293A cells by polyethylenimine (PEI). Antibodies were purified by protein A and subjected to specificity and affinity measurements by high-throughput glycan microarray. Specificity assay against a variety of glycans emphasized the high selectivity of these antibodies which are highly specific to $SLe^a$ related structures. The four highly bound glycans are $SLe^a$ with either Neu5Ac ($AcSLe^a$) or Neu5Gc ($GcSLe^a$) as the terminal sialic acid (glycan #83 and #86, respectively) and the 9-O-acetylated versions 9-O-$AcSLe^a$(glycan #87), 9-O-$GcSLe^a$(glycan #88). Glycans without sialic acid, as $Le^a$ (glycan #84) or Fucose Neu5Ac/NeuGc-a-2-3-Gal-B1-3-GlcNAc-β1-3-Lac-B (glycan #60/61) were not bound at all (FIG. 15B). In addition, the humanized antibodies showed similar ability as the chimeric antibody to bind $SLe^a$-positive WiDr colon cancer cell line by FACS staining (FIG. 16).

Figure 18:
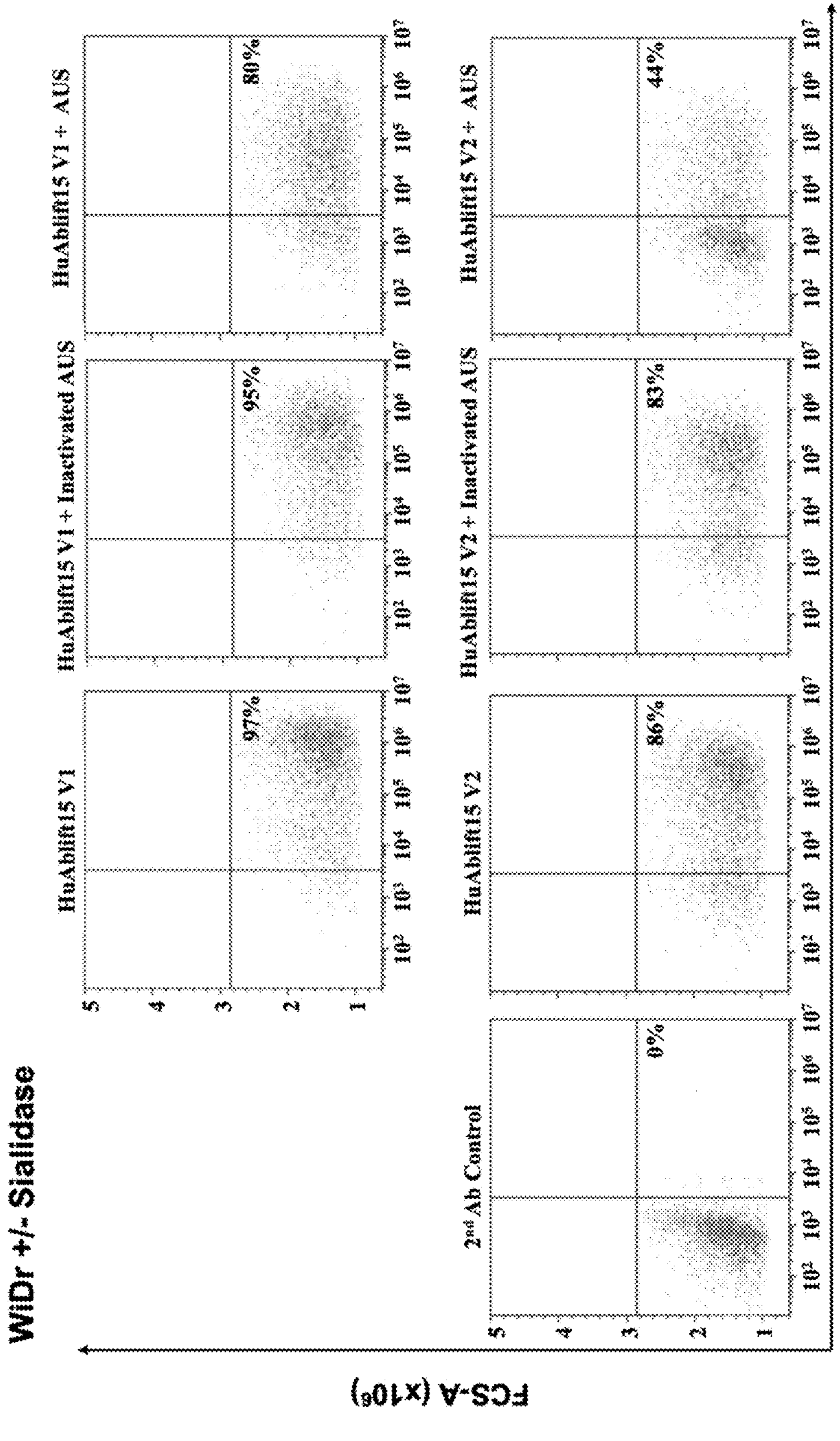
FIG. 18 shows antibodies cell binding specificity as demonstrated by treatment of cells with *Arthrobacter ureafaciens* Sialidase (AUS) that abrogated binding of HuAblift15 V1 (upper) and HuAblift15 V2 (lower) IgGs to $SLe^a$-expressing WiDr cells, in comparison to direct binding of the antibody or its binding to cells treated with heat-inactivated AUS.

Specificity of the full-length humanized antibodies was further demonstrated by ELISA inhibition assay, in which binding of HuAblift15 V1-hIgG or HuAblift15 V2-hlgG to $SLe^a$ was inhibited only with the specific glycan $SLe^a$, but not with the closely-related glycans $SLe^x$ or $Le^a$ (FIG. 17). Removal of sialic acids from the cell surface by a sialidase treatment dramatically reduced the binding of humanized antibodies to WiDr cells, thus showing the importance of sialic acid for the antibodies recognition (FIG. 18). Altogether, these data indicate that humanized antibodies maintain high specificity, affinity and cell recognition characteristics as original antibody.

Reduced Immunogenicity of Humanized Antibody Clones

Figure 19A:
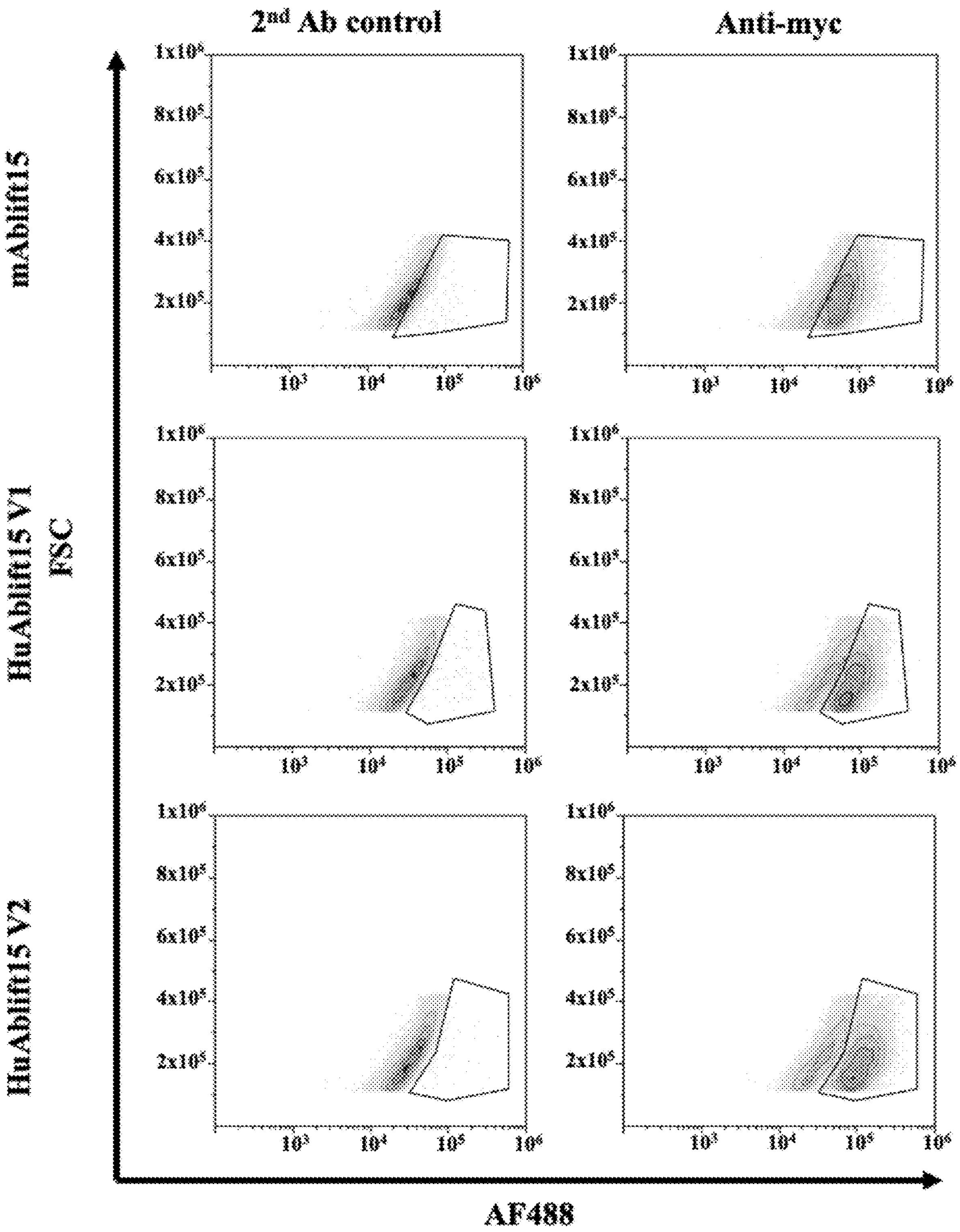
FIG. 19 shows reduced immunogenicity of humanized antibodies. Binding of pooled human IgG (pre-cleared of anti-yeast reactivity; yeast-purified IVIg) at 25, 50 and 100 ng/μl to scFv-mAblift15 (upper row), scFv-HuAblift15-V1 (middle row) and scFv-HuAblift15-V2 (lower row) yeast cells. Cells were first gated for scFv presenting cells by the AF488 fluorescence (stained by mouse-anti-c-Myc followed by Alexa-Fluor-488-goat-anti-mouse IgG1) (FIG. 19A). Positive IVIg binding on the gated scFv presenting cells was then determined by double positive signal of scFv presentation by c-myc labeling (AF488) and by binding of IVIg (Cy3; IVIg followed by Cy3-anti-human IgG Fc specific) (FIG. 19B). Then, IVIg-positive cells and IVIg-negative cells were separately gated (FIG. 19C; exemplified gating for scFv-mAblift15 cells labeled with IVIg at 25 ng/μl), and in each IVIg concentration the percent of IVIg-positive cells was divided by the percent of IVIg-negative cells. In each clone, the percentage ratio of (% IVIg-positive cells/% IVIg-negative cells) calculated for the three IVIg concentrations (25, 50 and 100 ng/μl) was averaged. Then, the ratios were normalized to scFv-mAblift15 yeast cells IVIg percent ratio, that was referred as the maximal signal (100%) (FIG. 19D). These data show a reduced immunogenicity, in which scFv-HuAblift15-V1 is about 43% of scFv-mAblift15, and scFv-HuAblift15-V2 is about 58% of scFv-mAblift15 (FIG. 19D). Representative of two independent experiments. One way ANOVA, Tukey, p<0.01, *p<0.001).
Figure 19B:
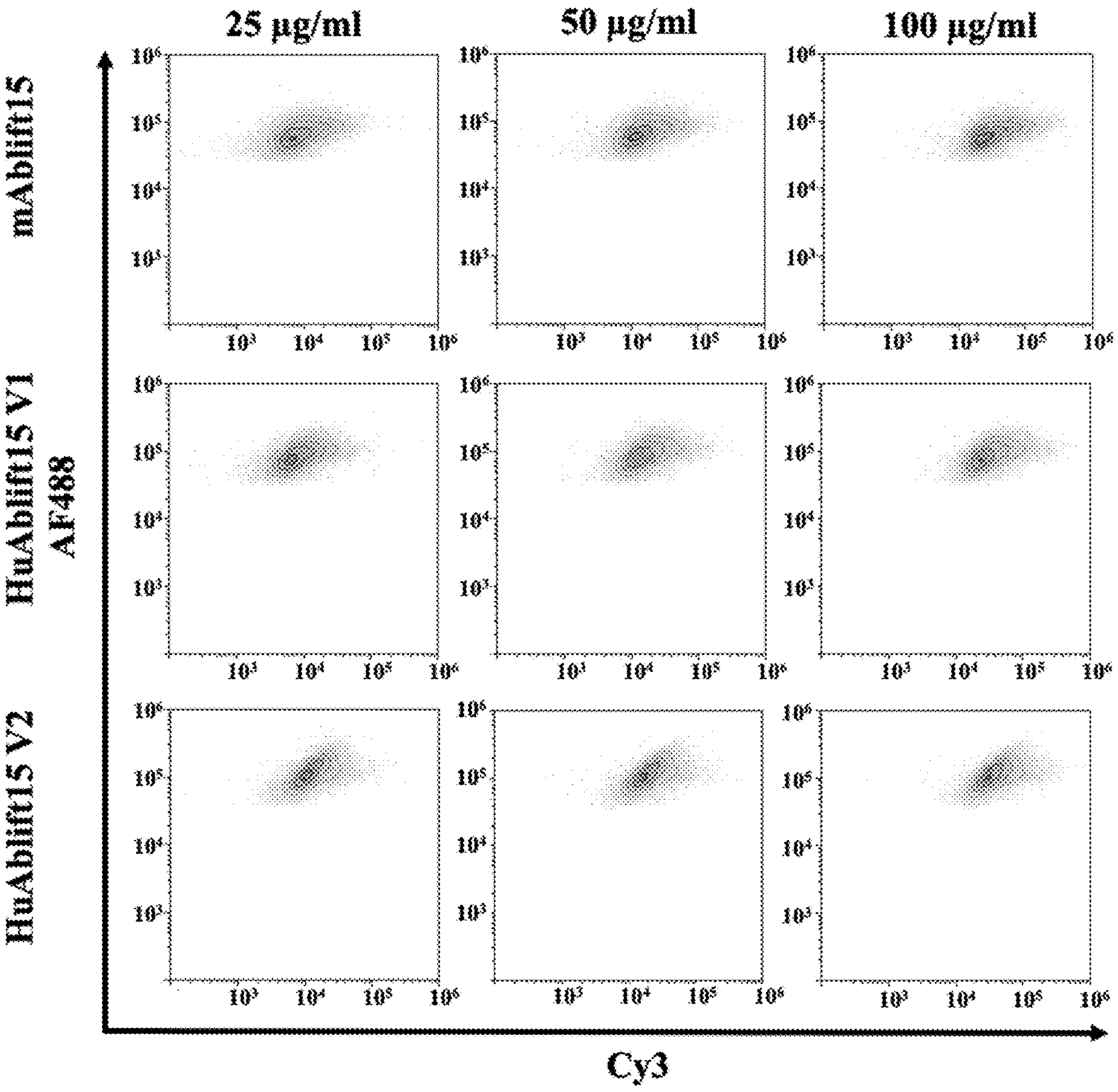

Immunogenicity of humanized antibodies clones was evaluated by analysis of scFv recognition by pooled human IgG obtained from thousands of human donors (IVIg; Gamma Gard). For this purpose, IVIg was first pre-cleared from anti-yeast reactivity by serial incubations with yeast cells, then binding to scFv-expressing yeast cells was examined by FACS. scFv-expression on yeast (Ablift15-YSD) was examined by mouse-anti-c-Myc (FIG. 19A) and pooled human IgG binding detected with anti-human IgG, and double positive labeling of scFv-expressing yeast cells was examined (FIG. 19B). The ratio of positive/negative (FIG. 19C) IVIg labeling indicate that that IVIg had reduced binding to the HuAblift15-V1 and HuAblift15-V2 compared to the mouse variants mAblift15. The HuAblift15-VI IVIg binding was 2 fold lower compared to mAblift15 IVIg binding. Similarly, the HuAblift15 V2 IVIg binding is 2.5 fold lower compared to mAblift15 IVIg binding (FIG. 19D). This analysis showed that IVIg had reduced binding to the HuAblift15 V1 and HuAblift15 V2 compared to the mouse variant mAblift15 in three different yeast-purified IVIg concentrations. The IVIg binding seems to bulge out to the right clearly showing a separate population of the IVIg bound antibodies on the yeast cells (FIG. 19B). Together, these data imply that the humanization process had decreased recognition of the antibody fragments with a large collection of pooled human IgG. In addition, it also suggests that engineered chimeric antigen receptor T cells (CAR T), in which the targeting moiety is actually expressed as scFv fragments would potentially have reduced recognition by human patient antibodies. This reduced immunogenicity of scFv is likely to support more stable CAR clones with potentially reduced risk of cytokine storm or other immunological events. Therefore, the humanized antibodies has a great potential as a therapeutic and diagnostic agents, with high specificity and affinity and potentially less side effects of immune response against mouse-derived clones.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. An isolated monoclonal antibody (mAb) or a fragment thereof that specifically binds to Sialyl Lewis A glycan (SLeA), wherein the mAb or the fragment comprises an antigen binding domain comprising a heavy-chain variable domain (VH) and a light-chain variable domain (VL) each comprising three complementarity determining regions (CDRs) and four framework domains (FR), wherein the VH-CDR 1 and 2 comprise the amino acid sequences SEQ ID NOs: 3 and 4, respectively, VH-CDR 3 comprises an amino acid sequence selected from SEQ ID NO: 5 and 9; VL-CDRs 1 and 3 comprise the amino acid sequences SEQ ID NOs: 6 and 12, respectively; and VL-CDR 2 comprises an amino acid sequence selected from SEQ ID NO: 10 and SEQ ID NO: 11.

2. The isolated mAb or the fragment according to claim 1, characterized by at least one of:

(i) the VH-FR3 comprises an amino acid sequence selected from SEQ ID NO: 13 and 14; and VL-FR2 and VL-FR3 comprise the amino acid sequences SEQ ID NOs: 15 and 16, respectively;

(ii) the VH and VL domains comprise the amino acid sequences SEQ ID NO: 1 and SEQ ID NO: 2, respectively, wherein (a) the VH comprises at least one substitution at a position selected from position 99, 100 and 104; and (b) the VL comprises a substitution at positions 56 and 98 and at least one additional amino acid substitution at a position selected from positions 43 and 87, wherein the substitution in VH at positions 99 and 100, if present, is each for Val, Ala, Leu or Ile; the substitution in VH at position 104, if present, is for Phe or Trp; the substitution in VL at position 43, if present, is for Pro, the substitution in VL at position 56 is for Val or Ala, the substitution in VL at positions 87, if present, is for Trp, and the substitution in VL at position 98 is each for Trp;

(iii) the VH comprises an amino acid sequence selected from SEQ ID NO: 17 and 19 and the VL comprises an amino acid sequence selected from SEQ ID NO: 18 and 20; and (iv) the VH comprises amino acid SEQ ID NO: 17 and the VL comprises amino acid sequence SEQ ID NO: 18.

3. The fragment according to claim 1, wherein the fragment is a single chain variable fragment (scFv).

4. The fragment according to claim 3, wherein the fragment is characterized by at least one of:

(i) the fragment comprises the amino acid sequences SEQ ID NO: 17 and SEQ ID NO: 18;

(ii) the fragment comprises the amino acid sequence SEQ ID NO: 21;

(iii) the fragment comprises the amino acid sequences SEQ ID NO: 19 and SEQ ID NO: 20, or the amino acid sequence SEQ ID NO: 22.

5. The isolated mAb or the fragment according to claim 1, wherein the isolated mAb or fragment (i) exhibit an increased affinity to CA19-9 as compared to an antibody comprising amino acid sequences SEQ ID NOs: 1 and 2, (ii) has KD of from 1 to 30 nM, or (iii) both (i) and (ii).

6. The antibody or the fragment according to claim 1, being humanized.

7. The humanized antibody or the fragment according to claim 6, characterized by at least one of:

(i) the VH domain comprises an amino acid sequence selected from SEQ ID NO: 17 and SEQ ID NO: 1 and the VL domain comprises amino acid sequence SEQ ID NO:18, wherein from 10 to 26 amino acid residues in the framework regions in the VH and VL domains are further substituted and wherein the substituted amino acids are not at positions 99 and 100 of the VH and not at positions 43 and 87 of the VL;

(ii) the VH comprises an amino acid sequence selected from SEQ ID NO: 23 and 25 and the VL comprises the amino acid sequence SEQ ID NO: 24;

(iii) the VH domain comprises amino acid sequence SEQ ID NO: 19 and the VL domain comprises amino acid sequence SEQ ID NO: 20, wherein from 10 to 26 amino acid residues in the framework regions in the VH and VL are further substituted and wherein the substituted amino acids are not at positions 99 and 100 of the VH and not at positions 43 and 87 of the VL;

(iv) the humanized antibody or the fragment thereof has KD of from 1 to 90 nM; and (v) the fragment is scFv.

8. The humanized antibody fragment according to claim 6, wherein the fragment is scFv comprising an amino acid sequence selected from SEQ ID NO: 26 and 27.

9. A conjugate comprising the mAb or the fragment according to claim 1 or humanized form thereof.

10. A chimeric antigen receptor (CAR) comprising the mAb or the fragment thereof according to claim 1 or humanized form thereof.

11. The CAR according to claim 10, wherein the CAR comprises (i) the VH and VL comprising amino acid sequences SEQ ID NO: 17 and 18, respectively; (ii) the VH and VL comprising amino acid sequences SEQ ID NO: 19 and 20, respectively; (iii) the VH and VL comprising amino acid sequences SEQ ID NO: 23 and 24, respectively; (iv) the VH and VL comprising amino acid sequences SEQ ID NO: 25 and 24, respectively; (v) a single chain variable fragment (scFv) comprising an amino acid sequence selected from SEQ ID NO: 21 and 22; or (vi) a humanized scFv comprising an amino acid sequence selected from SEQ ID NO: 26 and 27.

12. A nucleic acid molecule encoding at least one chain of the monoclonal antibody or fragment thereof according to 1, or a humanized form thereof or a CAR comprising the same or a nucleic acid construct comprising the nucleic acid molecule operably linked to a promoter or a vector comprising same.

13. The nucleic acid molecule according to claim 12, encoding at least one amino acid sequence selected from SEQ ID NOs: 17-27 or comprising the at least one nucleic acid sequence selected from SEQ ID NOs: 30-39.

14. A cell comprising at least one of:

(i) the mAb or the fragment thereof according to claim 1, (ii) a humanized form of the mAb or the fragment thereof according to claim 1, (iii) a CAR comprising the mAb or the fragment of (i) or (ii), (iv) a nucleic acid molecule encoding at least one chain of the mAb or the fragment of (i) or (ii) or the CAR of (iii), (v) a nucleic acid construct comprising the nucleic acid molecule of (iv), and (vi) a vector comprising the nucleic acid molecule of (iv) or the nucleic acid construct of (v).

15. The cell according to claim 14, wherein the cell (i) is selected from a T cell and a natural killer (NK) cell, (ii) expresses or is capable of expressing the CAR, or (iii) both (i) and (ii).

16. A composition comprising the isolated monoclonal antibodies or fragments thereof of claim 1, or conjugates or a CAR comprising same, or a plurality of cells comprising thereof and a carrier, optionally wherein the composition is a pharmaceutical composition and the carrier is a pharmaceutically acceptable carrier.

17. A method for treating cancer in a subject in need thereof comprising administering to said subject a therapeutically effective amount of isolated monoclonal antibodies or fragments thereof according claim 1, or conjugates thereof, or CAR comprising same or cells comprising same.

18. A method for diagnosing or monitoring cancer in a subject, the method comprises contacting a biological sample of the subject with the monoclonal antibodies or antibody fragments of claim 1 or conjugate thereof, under conditions which allow immunocomplexes formation, and assessing an amount of SLeA in the sample, wherein the cancer overexpresses SLeA glycan.

19. The method for diagnosing or monitoring cancer according to claim 18, characterized by at least one of:

(i) the method comprises comparing the assessed amount of SLeA in the sample to a threshold or to a reference, wherein the reference is a level of SLeA in a sample of healthy subjects, and wherein the amount of the SLeA in the sample above the reference or the threshold is indicative of the CA19-9+ malignancy, (ii) the monitoring cancer comprises monitoring progression or monitoring cancer treatment, wherein the method comprises comparing the amount of SLeA in the sample to a reference being a level of SLeA in prior sample of the subject, and a decrease in the amount of SLeA in comparison to the reference is indicative of amelioration of cancer; and (iii) the method further comprises recommendations for the treatment of cancer.

20. A kit for diagnosing or monitoring cancer in a subject, wherein the kit comprises the monoclonal antibodies or antibody fragments according to claim 1 or conjugate thereof.

* * * * *

SEQUENCE LISTING

```
<160> NUMBER OF SEQ ID NOS: 73

<210> SEQ ID NO 1
<211> LENGTH: 115
<212> TYPE: PRT
<213> ORGANISM: Mus Musculus

<400> SEQUENCE: 1

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Gly Asn Lys Gly Asn Asn His Ala Thr Tyr Tyr Ala Glu
    50                  55                  60

Ser Val Lys Gly Arg Phe Thr Val Ser Arg Asp Asp Ser Lys Ser Arg
65                  70                  75                  80
```

```
Val Tyr Leu Gln Met Asn Ser Leu Arg Val Glu Asp Thr Gly Thr Tyr
                85                  90                  95

Tyr Cys Thr Thr Arg Phe Ala Tyr Trp Gly Gln Gly Thr Leu Val Thr
            100                 105                 110

Val Ser Ala
        115


<210> SEQ ID NO 2
<211> LENGTH: 106
<212> TYPE: PRT
<213> ORGANISM: Mus Musculus

<400> SEQUENCE: 2

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Arg
                85                  90                  95

Thr Phe Gly Gly Gly Thr Lys Leu Glu Ile
            100                 105


<210> SEQ ID NO 3
<211> LENGTH: 5
<212> TYPE: PRT
<213> ORGANISM: Mus Musculus

<400> SEQUENCE: 3

Asp Ala Trp Met Asp
1               5


<210> SEQ ID NO 4
<211> LENGTH: 19
<212> TYPE: PRT
<213> ORGANISM: Mus Musculus

<400> SEQUENCE: 4

Glu Ile Gly Asn Lys Gly Asn Asn His Ala Thr Tyr Tyr Ala Glu Ser
1               5                   10                  15

Val Lys Gly


<210> SEQ ID NO 5
<211> LENGTH: 4
<212> TYPE: PRT
<213> ORGANISM: Mus Musculus

<400> SEQUENCE: 5

Arg Phe Ala Tyr
1


<210> SEQ ID NO 6
<211> LENGTH: 11
<212> TYPE: PRT
<213> ORGANISM: Mus Musculus
```

<400> SEQUENCE: 6

Lys Ala Ser Gln Asp Ile Asn Ser Tyr Leu Ser
1 5 10

<210> SEQ ID NO 7
<211> LENGTH: 7
<212> TYPE: PRT
<213> ORGANISM: Mus Musculus

<400> SEQUENCE: 7

Arg Ala Asn Arg Leu Val Asp
1 5

<210> SEQ ID NO 8
<211> LENGTH: 10
<212> TYPE: PRT
<213> ORGANISM: Mus Musculus

<400> SEQUENCE: 8

Leu Gln Tyr Asp Glu Phe Pro Arg Thr Phe
1 5 10

<210> SEQ ID NO 9
<211> LENGTH: 4
<212> TYPE: PRT
<213> ORGANISM: Artificial Sequence
<220> FEATURE:
<223> OTHER INFORMATION: Synthetic

<400> SEQUENCE: 9

Arg Phe Ala Phe
1

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Arg Ala Asn Arg Leu Val Ala
1 5

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Arg Ala Asn Arg Leu Val Pro
1 5

<210> SEQ ID NO 12
<211> LENGTH: 10
<212> TYPE: PRT
<213> ORGANISM: Artificial Sequence
<220> FEATURE:
<223> OTHER INFORMATION: Synthetic

<400> SEQUENCE: 12

Leu Gln Tyr Asp Glu Phe Pro Arg Thr Trp
1 5 10

<210> SEQ ID NO 13
<211> LENGTH: 32
<212> TYPE: PRT
<213> ORGANISM: Artificial Sequence
<220> FEATURE:
<223> OTHER INFORMATION: Synthetic

<400> SEQUENCE: 13

```
Arg Phe Thr Val Ser Arg Asp Asp Ser Lys Ser Arg Val Tyr Leu Gln
1               5                   10                  15

Met Asn Ser Leu Arg Val Glu Asp Thr Gly Thr Tyr Tyr Cys Val Val
            20                  25                  30
```

<210> SEQ ID NO 14
<211> LENGTH: 32
<212> TYPE: PRT
<213> ORGANISM: Artificial Sequence
<220> FEATURE:
<223> OTHER INFORMATION: Synthetic

<400> SEQUENCE: 14

```
Arg Phe Thr Val Ser Arg Asp Asp Ser Lys Ser Arg Val Tyr Leu Gln
1               5                   10                  15

Met Asn Ser Leu Arg Val Glu Asp Thr Gly Thr Tyr Tyr Cys Val Val
            20                  25                  30
```

<210> SEQ ID NO 15
<211> LENGTH: 15
<212> TYPE: PRT
<213> ORGANISM: Artificial Sequence
<220> FEATURE:
<223> OTHER INFORMATION: Synthetic

<400> SEQUENCE: 15

```
Trp Phe Gln Gln Lys Pro Gly Lys Pro Pro Lys Thr Leu Ile Tyr
1               5                   10                  15
```

<210> SEQ ID NO 16
<211> LENGTH: 31
<212> TYPE: PRT
<213> ORGANISM: Artificial Sequence
<220> FEATURE:
<223> OTHER INFORMATION: Synthetic

<400> SEQUENCE: 16

```
Gly Val Pro Ser Arg Phe Ser Gly Ser Gly Ser Gly Gln Asp Tyr Ser
1               5                   10                  15

Leu Thr Ile Ser Ser Leu Glu Tyr Glu Asp Met Gly Ile Tyr Trp
            20                  25                  30
```

<210> SEQ ID NO 17
<211> LENGTH: 115
<212> TYPE: PRT
<213> ORGANISM: Artificial Sequence
<220> FEATURE:
<223> OTHER INFORMATION: Synthetic

<400> SEQUENCE: 17

```
Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
```

```
        35                  40                  45

Ala Glu Ile Gly Asn Lys Gly Asn Asn His Ala Thr Tyr Tyr Ala Glu
    50                  55                  60

Ser Val Lys Gly Arg Phe Thr Val Ser Arg Asp Asp Ser Lys Ser Arg
65                  70                  75                  80

Val Tyr Leu Gln Met Asn Ser Leu Arg Val Glu Asp Thr Gly Thr Tyr
                85                  90                  95

Tyr Cys Ala Val Arg Phe Ala Phe Trp Gly Gln Gly Thr Leu Val Thr
            100                 105                 110

Val Ser Ala
        115


<210> SEQ ID NO 18
<211> LENGTH: 106
<212> TYPE: PRT
<213> ORGANISM: Artificial Sequence
<220> FEATURE:
<223> OTHER INFORMATION: Synthetic

<400> SEQUENCE: 18

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Pro Pro Lys Thr Leu Ile
        35                  40                  45

Tyr Arg Ala Asn Arg Leu Val Pro Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Trp Cys Leu Gln Tyr Asp Glu Phe Pro Arg
                85                  90                  95

Thr Trp Gly Gly Gly Thr Lys Leu Glu Ile
            100                 105


<210> SEQ ID NO 19
<211> LENGTH: 115
<212> TYPE: PRT
<213> ORGANISM: Artificial Sequence
<220> FEATURE:
<223> OTHER INFORMATION: Synthetic

<400> SEQUENCE: 19

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Gly Asn Lys Gly Asn Asn His Ala Thr Tyr Tyr Ala Glu
    50                  55                  60

Ser Val Lys Gly Arg Phe Thr Val Ser Arg Asp Asp Ser Lys Ser Arg
65                  70                  75                  80

Val Tyr Leu Gln Met Asn Ser Leu Arg Val Glu Asp Thr Gly Thr Tyr
                85                  90                  95

Tyr Cys Val Val Arg Phe Ala Tyr Trp Gly Gln Gly Thr Leu Val Thr
            100                 105                 110
```

Val Ser Ala
115

<210> SEQ ID NO 20
<211> LENGTH: 106
<212> TYPE: PRT
<213> ORGANISM: Artificial Sequence
<220> FEATURE:
<223> OTHER INFORMATION: Synthetic

<400> SEQUENCE: 20

Asp Ile Lys Met Thr Gln Ser Pro Ser Ser Met Tyr Ala Ser Leu Gly
1 5 10 15

Glu Arg Val Thr Ile Thr Cys Lys Ala Ser Gln Asp Ile Asn Ser Tyr
20 25 30

Leu Ser Trp Phe Gln Gln Lys Pro Gly Lys Pro Pro Lys Thr Leu Ile
35 40 45

Tyr Arg Ala Asn Arg Leu Val Val Gly Val Pro Ser Arg Phe Ser Gly
50 55 60

Ser Gly Ser Gly Gln Asp Tyr Ser Leu Thr Ile Ser Ser Leu Glu Tyr
65 70 75 80

Glu Asp Met Gly Ile Tyr Trp Cys Leu Gln Tyr Asp Glu Phe Pro Arg
85 90 95

Thr Trp Gly Gly Gly Thr Lys Leu Glu Ile
100 105

<210> SEQ ID NO 21
<211> LENGTH: 237
<212> TYPE: PRT
<213> ORGANISM: Artificial Sequence
<220> FEATURE:
<223> OTHER INFORMATION: Synthetic

<400> SEQUENCE: 21

Glu Val Lys Leu Glu Glu Ser Gly Gly Gly Leu Val Gln Pro Gly Gly
1 5 10 15

Ser Met Lys Leu Ser Cys Ala Ala Ser Gly Phe Thr Phe Ser Asp Ala
20 25 30

Trp Met Asp Trp Val Arg Gln Ser Pro Glu Lys Gly Leu Glu Trp Val
35 40 45

Ala Glu Ile Gly Asn Lys Gly Asn Asn His Ala Thr Tyr Tyr Ala Glu
50 55 60

Ser Val Lys Gly Arg Phe Thr Val Ser Arg Asp Asp Ser Lys Ser Arg
65 70 75 80

Val Tyr Leu Gln Met Asn Ser Leu Arg Val Glu Asp Thr Gly Thr Tyr
85 90 95

Tyr Cys Ala Val Arg Phe Ala Phe Trp Gly Gln Gly Thr Leu Val Thr
100 105 110

Val Ser Ala Gly Gly Gly Gly Ser Gly Gly Gly Gly Ser Gly Gly Gly
115 120 125

Gly Ser Asp Ile Lys Met Thr Gln Ser Pro Ser Ser Met Tyr Ala Ser
130 135 140

Leu Gly Glu Arg Val Thr Ile Thr Cys Lys Ala Ser Gln Asp Ile Asn
145 150 155 160

Ser Tyr Leu Ser Trp Phe Gln Gln Lys Pro Gly Lys Pro Pro Lys Thr
165 170 175

Leu Ile Tyr Arg Ala Asn Arg Leu Val Pro Gly Val Pro Ser Arg Phe
180 185 190

Ser Gly Ser Gly Ser Gly Gln Asp Tyr Ser Leu Thr Ile Ser Ser Leu
195 200 205

Glu Tyr Glu Asp Met Gly Ile Tyr Trp Cys Leu Gln Tyr Asp Glu Phe
210 215 220

Pro Arg Thr Trp Gly Gly Gly Thr Lys Leu Glu Ile Lys
225 230 235

<210> SEQ ID NO 22
<211> LENGTH: 236
<212> TYPE: PRT
<213> ORGANISM: Artificial Sequence
<220> FEATURE:
<223> OTHER INFORMATION: Synthetic

<400> SEQUENCE: 22

Glu Val Lys Leu Glu Glu Ser Gly Gly Gly Leu Val Gln Pro Gly Gly
1 5 10 15

Ser Met Lys Leu Ser Cys Ala Ala Ser Gly Phe Thr Phe Ser Asp Ala
20 25 30

Trp Met Asp Trp Val Arg Gln Ser Pro Glu Lys Gly Leu Glu Trp Val
35 40 45

Ala Glu Ile Gly Asn Lys Gly Asn Asn His Ala Thr Tyr Tyr Ala Glu
50 55 60

Ser Val Lys Gly Arg Phe Thr Val Ser Arg Asp Asp Ser Lys Ser Arg
65 70 75 80

Val Tyr Leu Gln Met Asn Ser Leu Arg Val Glu Asp Thr Gly Thr Tyr
85 90 95

Tyr Cys Val Val Arg Phe Ala Tyr Trp Gly Gln Gly Thr Leu Val Thr
100 105 110

Val Ser Ala Gly Gly Gly Gly Ser Gly Gly Gly Gly Ser Gly Gly Gly
115 120 125

Gly Ser Asp Ile Lys Met Thr Gln Ser Pro Ser Ser Met Tyr Ala Ser
130 135 140

Leu Gly Glu Arg Val Thr Ile Thr Cys Lys Ala Ser Gln Asp Ile Asn
145 150 155 160

Ser Tyr Leu Ser Trp Phe Gln Gln Lys Pro Gly Lys Pro Pro Lys Thr
165 170 175

Leu Ile Tyr Arg Ala Asn Arg Leu Val Val Gly Val Pro Ser Arg Phe
180 185 190

Ser Gly Ser Gly Ser Gly Gln Asp Tyr Ser Leu Thr Ile Ser Ser Leu
195 200 205

Glu Tyr Glu Asp Met Gly Ile Tyr Trp Cys Leu Gln Tyr Asp Glu Phe
210 215 220

Pro Arg Thr Trp Gly Gly Gly Thr Lys Leu Glu Ile
225 230 235

<210> SEQ ID NO 23
<211> LENGTH: 115
<212> TYPE: PRT
<213> ORGANISM: Artificial Sequence
<220> FEATURE:
<223> OTHER INFORMATION: Synthetic

<400> SEQUENCE: 23

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Ala

```
            20                  25                  30

Trp Met Asp Trp Val Arg Gln Ala Pro Gly Lys Gly Leu Glu Trp Val
        35                  40                  45

Ala Glu Ile Gly Asn Lys Gly Asn Asn His Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Val Arg Phe Ala Phe Trp Gly Gln Gly Thr Leu Val Thr
            100                 105                 110

Val Ser Ser
        115


<210> SEQ ID NO 24
<211> LENGTH: 107
<212> TYPE: PRT
<213> ORGANISM: Artificial Sequence
<220> FEATURE:
<223> OTHER INFORMATION: Synthetic

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Pro Pro Lys Leu Leu Ile
        35                  40                  45

Tyr Arg Ala Asn Arg Leu Val Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Trp Cys Leu Gln Tyr Asp Glu Phe Pro Arg
                85                  90                  95

Thr Trp Gly Gly Gly Thr Lys Val Glu Ile Lys
            100                 105


<210> SEQ ID NO 25
<211> LENGTH: 115
<212> TYPE: PRT
<213> ORGANISM: Artificial Sequence
<220> FEATURE:
<223> OTHER INFORMATION: Synthetic

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Gly Asn Lys Gly Asn Asn His Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95
```

```
Tyr Cys Thr Thr Arg Phe Ala Tyr Trp Gly Gln Gly Thr Leu Val Thr
            100                 105                 110

Val Ser Ser
        115


<210> SEQ ID NO 26
<211> LENGTH: 237
<212> TYPE: PRT
<213> ORGANISM: Artificial Sequence
<220> FEATURE:
<223> OTHER INFORMATION: Synthetic

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Gly Asn Lys Gly Asn Asn His Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Val Arg Phe Ala Phe Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Gln Met Thr Gln Ser Pro Ser Ser Leu Ser Ala Ser
    130                 135                 140

Val Gly Asp Arg Val Thr Ile Thr Cys Lys Ala Ser Gln Asp Ile Asn
145                 150                 155                 160

Ser Tyr Leu Ser Trp Phe Gln Gln Lys Pro Gly Lys Pro Pro Lys Leu
                165                 170                 175

Leu Ile Tyr Arg Ala Asn Arg Leu Val Pro Gly Val Pro Ser Arg Phe
            180                 185                 190

Ser Gly Ser Gly Ser Gly Thr Asp Phe Thr Phe Thr Ile Ser Ser Leu
        195                 200                 205

Gln Pro Glu Asp Ile Ala Thr Tyr Trp Cys Leu Gln Tyr Asp Glu Phe
    210                 215                 220

Pro Arg Thr Trp Gly Gly Gly Thr Lys Val Glu Ile Lys
225                 230                 235


<210> SEQ ID NO 27
<211> LENGTH: 237
<212> TYPE: PRT
<213> ORGANISM: Artificial Sequence
<220> FEATURE:
<223> OTHER INFORMATION: Synthetic

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45
```

```
Ala Glu Ile Gly Asn Lys Gly Asn Asn His Ala Thr Tyr Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Thr Arg Phe Ala Tyr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Asp Ile Gln Met Thr Gln Ser Pro Ser Ser Leu Ser Ala Ser
    130                 135                 140

Val Gly Asp Arg Val Thr Ile Thr Cys Lys Ala Ser Gln Asp Ile Asn
145                 150                 155                 160

Ser Tyr Leu Ser Trp Phe Gln Gln Lys Pro Gly Lys Pro Pro Lys Leu
                165                 170                 175

Leu Ile Tyr Arg Ala Asn Arg Leu Val Pro Gly Val Pro Ser Arg Phe
            180                 185                 190

Ser Gly Ser Gly Ser Gly Thr Asp Phe Thr Phe Thr Ile Ser Ser Leu
        195                 200                 205

Gln Pro Glu Asp Ile Ala Thr Tyr Trp Cys Leu Gln Tyr Asp Glu Phe
    210                 215                 220

Pro Arg Thr Trp Gly Gly Gly Thr Lys Val Glu Ile Lys
225                 230                 235
```

<210> SEQ ID NO 28
<211> LENGTH: 345
<212> TYPE: DNA
<213> ORGANISM: Mus Musculus

<400> SEQUENCE: 28

```
gaagtcaagc tagaagaaag cggtggcgga cttgttcagc ctgggggatc catgaagtta     60

tcttgcgccg catccggttt taccttttct gatgcctgga tggattgggt gagacaatct    120

ccagaaaaag gtctggaatg ggtagccgaa attggtaaca agggcaataa tcacgccacg    180

tactatgccg agtctgtaaa aggaagattc actgtttcca gagacgattc aaagtccaga    240

gtctatctac aaatgaattc attaagagtc gaagatactg gtacttacta ctgtaccact    300

aggtttgcat attggggtca aggtacactg gtgacggttt ctgcc                    345
```

<210> SEQ ID NO 29
<211> LENGTH: 318
<212> TYPE: DNA
<213> ORGANISM: Mus Musculus

<400> SEQUENCE: 29

```
gacattaaaa tgactcagag tccatcctca atgtacgctt ccttaggaga aagagtcact     60

atcacttgca aggcatccca agatatcaac tcatacttga gttggttcca acaaaaacca    120

ggtaaatctc ctaaaaccct gatttatcgt gccaataggc ttgtggatgg cgttccatcc    180

agattcagcg gatcaggtag tgggcaagat tattctttga caatttcctc attggaatac    240

gaagatatgg gcatatacta ttgcttacag tatgatgagt ttccacgtac ttttggcggt    300

ggaacaaaat tagaaatc                                                  318
```

<210> SEQ ID NO 30

<211> LENGTH: 345
<212> TYPE: DNA
<213> ORGANISM: Artificial Sequence
<220> FEATURE:
<223> OTHER INFORMATION: Synthetic

<400> SEQUENCE: 30
gaagtcaagc tagaagaaag cggtggcgga cttgttcagc ctgggggatc catgaagtta 60
tcttgcgccg catccggttt taccttttct gatgcctgga tggattgggt gagacaatct 120
ccagaaaaag gtctggaatg ggtagccgaa attggtaaca agggcaataa tcacgccacg 180
tactatgccg agtctgtaaa aggaagattc actgtttcca gagacgattc aaagtccaga 240
gtctatctac aaatgaattc attaagagtc gaagatactg gtacttacta ctgtgccgtg 300
aggtttgcat tctggggtca aggtacactg gtgacggttt ctgcc 345

<210> SEQ ID NO 31
<211> LENGTH: 318
<212> TYPE: DNA
<213> ORGANISM: Artificial Sequence
<220> FEATURE:
<223> OTHER INFORMATION: Synthetic

<400> SEQUENCE: 31
gacattaaaa tgactcagag tccatcctca atgtacgctt ccttaggaga aagagtcact 60
atcacttgca aggcatccca agatatcaac tcatacttga gttggttcca acaaaaacca 120
ggtaaacccc ctaaaaccct gatttatcgt gccaataggc ttgtgcccgg cgttccatcc 180
agattcagcg gatcaggtag tgggcaagat tattctttga caatttcctc attggaatac 240
gaagatatgg gcatatactg gtgcttacag tatgatgagt ttccacgtac ttggggcggt 300
ggaacaaaat tagaaatc 318

<210> SEQ ID NO 32
<211> LENGTH: 345
<212> TYPE: DNA
<213> ORGANISM: Artificial Sequence
<220> FEATURE:
<223> OTHER INFORMATION: Synthetic

<400> SEQUENCE: 32
gaagtcaagc tagaagaaag cggtggcgga cttgttcagc ctgggggatc catgaagtta 60
tcttgcgccg catccggttt taccttttct gatgcctgga tggattgggt gagacaatct 120
ccagaaaaag gtctggaatg ggtagccgaa attggtaaca agggcaataa tcacgccacg 180
tactatgccg agtctgtaaa aggaagattc actgtttcca gagacgattc aaagtccaga 240
gtctatctac aaatgaattc attaagagtc gaagatactg gtacttacta ctgtgtggtg 300
aggtttgcat attggggtca aggtacactg gtgacggttt ctgcc 345

<210> SEQ ID NO 33
<211> LENGTH: 318
<212> TYPE: DNA
<213> ORGANISM: Artificial Sequence
<220> FEATURE:
<223> OTHER INFORMATION: Synthetic

<400> SEQUENCE: 33
gacattaaaa tgactcagag tccatcctca atgtacgctt ccttaggaga aagagtcact 60
atcacttgca aggcatccca agatatcaac tcatacttga gttggttcca acaaaaacca 120
ggtaaacccc ctaaaaccct gatttatcgt gccaataggc ttgtggccgg cgttccatcc 180
agattcagcg gatcaggtag tgggcaagat tattctttga caatttcctc attggaatac 240
gaagatatgg gcatatactg gtgcttacag tatgatgagt ttccacgtac ttggggcggt 300
ggaacaaaat tagaaatc 318

<210> SEQ ID NO 34
<211> LENGTH: 711
<212> TYPE: DNA
<213> ORGANISM: Artificial Sequence
<220> FEATURE:
<223> OTHER INFORMATION: Synthetic

<400> SEQUENCE: 34
gaagtcaagc tagaagaaag cggtggcgga cttgttcagc ctgggggatc catgaagtta 60
tcttgcgccg catccggttt taccttttct gatgcctgga tggattgggt gagacaatct 120
ccagaaaaag gtctggaatg ggtagccgaa attggtaaca agggcaataa tcacgccacg 180
tactatgccg agtctgtaaa aggaagattc actgtttcca gagacgattc aaagtccaga 240
gtctatctac aaatgaattc attaagagtc gaagatactg gtacttacta ctgtgccgtg 300
aggtttgcat tctggggtca aggtacactg gtgacggttt ctgccggagg tggcggtagc 360
ggaggcggcg gttctggagg tggcgggagc gacattaaaa tgactcagag tccatcctca 420
atgtacgctt ccttaggaga aagagtcact atcacttgca aggcatccca agatatcaac 480
tcatacttga gttggttcca acaaaaacca ggtaaacccc ctaaaaccct gatttatcgt 540
gccaataggc ttgtgcccgg cgttccatcc agattcagcg gatcaggtag tgggcaagat 600
tattctttga caatttcctc attggaatac gaagatatgg gcatatactg gtgcttacag 660
tatgatgagt ttccacgtac ttggggcggt ggaacaaaat tagaaatcaa a 711

<210> SEQ ID NO 35
<211> LENGTH: 345
<212> TYPE: DNA
<213> ORGANISM: Artificial Sequence
<220> FEATURE:
<223> OTHER INFORMATION: Synthetic

<400> SEQUENCE: 35
gaggtgcagc tggtggagtc tgggggaggc ttggtccagc ctggagggtc cctgagactc 60
tcctgtgcag cctctggatt caccttcagt gatgcctgga tggattgggt ccgccaggct 120
ccagggaagg ggctggagtg ggttgccgaa attggtaaca agggcaataa tcacgccacg 180
tactatgccg agtctgtaaa aggaagattc accatctcaa gagatgattc aaagaactca 240
ctgtatctgc aaatgaacag cctgaaaacc gaggacacgg ccgtgtatta ctgtgccgtg 300
aggtttgcat tctggggcca aggaaccctg gtcaccgtct cctca 345

<210> SEQ ID NO 36
<211> LENGTH: 321
<212> TYPE: DNA
<213> ORGANISM: Artificial Sequence
<220> FEATURE:
<223> OTHER INFORMATION: Synthetic

<400> SEQUENCE: 36
gacatccaga tgacccagtc tccatcctcc ctgtctgcat ctgtaggaga cagagtcacc 60
atcacttgca aggcatccca agatatcaac tcatacttga gttggttcca gcagaaacca 120
gggaaacccc ctaagctcct gatctaccgt gccaataggc ttgtgcccgg ggtcccatca 180
aggttcagtg gaagtggatc tgggacagat tttactttca ccatcagcag cctgcagcct 240
gaagatattg caacatattg gtgtttacag tatgatgagt ttccacgtac ttggggcgga 300
gggaccaagg tggagatcaa a 321

<210> SEQ ID NO 37
<211> LENGTH: 345
<212> TYPE: DNA
<213> ORGANISM: Artificial Sequence
<220> FEATURE:
<223> OTHER INFORMATION: Synthetic

<400> SEQUENCE: 37
gaggtgcagc tggtggagtc tgggggaggc ttggtccagc ctggagggtc cctgagactc 60
tcctgtgcag cctctggatt caccttcagt gatgcctgga tggattgggt ccgccaggct 120
ccagggaagg ggctggagtg ggttgccgaa attggtaaca agggcaataa tcacgccacg 180
tactatgccg agtctgtaaa aggaagattc accatctcaa gagatgattc aaagaactca 240
ctgtatctgc aaatgaacag cctgaaaacc gaggacacgg ccgtgtatta ctgtaccact 300
aggtttgcat attggggcca aggaaccctg gtcaccgtct cctca 345

<210> SEQ ID NO 38
<211> LENGTH: 711
<212> TYPE: DNA
<213> ORGANISM: Artificial Sequence
<220> FEATURE:
<223> OTHER INFORMATION: Synthetic

<400> SEQUENCE: 38
gaggtgcagc tggtggagtc tgggggaggc ttggtccagc ctggagggtc cctgagactc 60
tcctgtgcag cctctggatt caccttcagt gatgcctgga tggattgggt ccgccaggct 120
ccagggaagg ggctggagtg ggttgccgaa attggtaaca agggcaataa tcacgccacg 180
tactatgccg agtctgtaaa aggaagattc accatctcaa gagatgattc aaagaactca 240
ctgtatctgc aaatgaacag cctgaaaacc gaggacacgg ccgtgtatta ctgtgccgtg 300
aggtttgcat tctggggcca aggaaccctg gtcaccgtct cctcaggagg tggcggtagc 360
ggaggcggcg gttctggagg tggcgggagc gacatccaga tgacccagtc tccatcctcc 420
ctgtctgcat ctgtaggaga cagagtcacc atcacttgca aggcatccca agatatcaac 480
tcatacttga gttggttcca gcagaaacca gggaaacccc ctaagctcct gatctaccgt 540
gccaataggc ttgtgcccgg ggtcccatca aggttcagtg gaagtggatc tgggacagat 600
tttactttca ccatcagcag cctgcagcct gaagatattg caacatattg gtgtttacag 660
tatgatgagt ttccacgtac ttggggcgga gggaccaagg tggagatcaa a 711

<210> SEQ ID NO 39
<211> LENGTH: 711
<212> TYPE: DNA
<213> ORGANISM: Artificial Sequence
<220> FEATURE:
<223> OTHER INFORMATION: Synthetic

<400> SEQUENCE: 39
gaggtgcagc tggtggagtc tgggggaggc ttggtccagc ctggagggtc cctgagactc 60
tcctgtgcag cctctggatt caccttcagt gatgcctgga tggattgggt ccgccaggct 120
ccagggaagg ggctggagtg ggttgccgaa attggtaaca agggcaataa tcacgccacg 180
tactatgccg agtctgtaaa aggaagattc accatctcaa gagatgattc aaagaactca 240
ctgtatctgc aaatgaacag cctgaaaacc gaggacacgg ccgtgtatta ctgtaccact 300
aggtttgcat attggggcca aggaaccctg gtcaccgtct cctcaggagg tggcggtagc 360
ggaggcggcg gttctggagg tggcgggagc gacatccaga tgacccagtc tccatcctcc 420
ctgtctgcat ctgtaggaga cagagtcacc atcacttgca aggcatccca agatatcaac 480
tcatacttga gttggttcca gcagaaacca gggaaacccc ctaagctcct gatctaccgt 540
gccaataggc ttgtgcccgg ggtcccatca aggttcagtg gaagtggatc tgggacagat 600
tttactttca ccatcagcag cctgcagcct gaagatattg caacatattg gtgtttacag 660
tatgatgagt ttccacgtac ttggggcgga gggaccaagg tggagatcaa a 711

<210> SEQ ID NO 40
<211> LENGTH: 35
<212> TYPE: DNA
<213> ORGANISM: Artificial Sequence
<220> FEATURE:
<223> OTHER INFORMATION: Synthetic

<400> SEQUENCE: 40
tctggtggag gcggtagcgg aggcggaggg tcggc 35

<210> SEQ ID NO 41
<211> LENGTH: 45
<212> TYPE: DNA
<213> ORGANISM: Artificial Sequence
<220> FEATURE:
<223> OTHER INFORMATION: Synthetic

<400> SEQUENCE: 41
ttacaagtcc tcttcagaaa taagcttttg ttcggatccg ccccc 45

<210> SEQ ID NO 42
<211> LENGTH: 53
<212> TYPE: DNA
<213> ORGANISM: Artificial Sequence
<220> FEATURE:
<223> OTHER INFORMATION: Synthetic

<400> SEQUENCE: 42
gtagcaactg caaccggtgt acattcagac attaaaatga ctcagagtcc atc 53

<210> SEQ ID NO 43
<211> LENGTH: 43
<212> TYPE: DNA
<213> ORGANISM: Artificial Sequence
<220> FEATURE:
<223> OTHER INFORMATION: Synthetic

<400> SEQUENCE: 43
ggtgcagcca ccgtacgttt gatttctaat tttgttccac cgc 43

<210> SEQ ID NO 44
<211> LENGTH: 49
<212> TYPE: DNA
<213> ORGANISM: Artificial Sequence
<220> FEATURE:
<223> OTHER INFORMATION: Synthetic

<400> SEQUENCE: 44
gtagcaactg caaccggtgt acattgcgaa gtcaagctag aagaaagcg 49

<210> SEQ ID NO 45

<211> LENGTH: 38
<212> TYPE: DNA
<213> ORGANISM: Artificial Sequence
<220> FEATURE:
<223> OTHER INFORMATION: Synthetic

<400> SEQUENCE: 45
gatgggccct tggtcgacgc ggcagaaacc gtcaccag 38

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
gcgtcgacca agggcccatc 20

<210> SEQ ID NO 47
<211> LENGTH: 23
<212> TYPE: DNA
<213> ORGANISM: Artificial Sequence
<220> FEATURE:
<223> OTHER INFORMATION: Synthetic

<400> SEQUENCE: 47
caaccaagtc attctgagaa tag 23

<210> SEQ ID NO 48
<211> LENGTH: 23
<212> TYPE: DNA
<213> ORGANISM: Artificial Sequence
<220> FEATURE:
<223> OTHER INFORMATION: Synthetic

<400> SEQUENCE: 48
ctattctcag aatgacttgg ttg 23

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
gcaatgtaca ccggttgcag 20

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
cgtacggtgg ctgcaccatc 20

<210> SEQ ID NO 51
<211> LENGTH: 23
<212> TYPE: DNA
<213> ORGANISM: Artificial Sequence
<220> FEATURE:
<223> OTHER INFORMATION: Synthetic

<400> SEQUENCE: 51

-continued tgaatgtaca ccggttgcag ttg 23

<210> SEQ ID NO 52
<211> LENGTH: 35
<212> TYPE: DNA
<213> ORGANISM: Artificial Sequence
<220> FEATURE:
<223> OTHER INFORMATION: Synthetic

<400> SEQUENCE: 52
tctggtggag gcggtagcgg aggcggaggg tcggc 35

<210> SEQ ID NO 53
<211> LENGTH: 45
<212> TYPE: DNA
<213> ORGANISM: Artificial Sequence
<220> FEATURE:
<223> OTHER INFORMATION: Synthetic

<400> SEQUENCE: 53
ttacaagtcc tcttcagaaa taagcttttg ttcggatccg ccccc 45

<210> SEQ ID NO 54
<211> LENGTH: 49
<212> TYPE: DNA
<213> ORGANISM: Artificial Sequence
<220> FEATURE:
<223> OTHER INFORMATION: Synthetic

<400> SEQUENCE: 54
gtagcaactg caaccggtgt acattcagac atccagatga cccagtctc 49

<210> SEQ ID NO 55
<211> LENGTH: 40
<212> TYPE: DNA
<213> ORGANISM: Artificial Sequence
<220> FEATURE:
<223> OTHER INFORMATION: Synthetic

<400> SEQUENCE: 55
ggtgcagcca ccgtacgttt gatctccacc ttggtccctc 40

<210> SEQ ID NO 56
<211> LENGTH: 47
<212> TYPE: DNA
<213> ORGANISM: Artificial Sequence
<220> FEATURE:
<223> OTHER INFORMATION: Synthetic

<400> SEQUENCE: 56
gtagcaactg caaccggtgt acattgcgag gtgcagctgg tggagtc 47

<210> SEQ ID NO 57
<211> LENGTH: 38
<212> TYPE: DNA
<213> ORGANISM: Artificial Sequence
<220> FEATURE:
<223> OTHER INFORMATION: Synthetic

<400> SEQUENCE: 57
gatgggccct tggtcgacgc tgaggagacg gtgaccag 38

<210> SEQ ID NO 58
<211> LENGTH: 53
<212> TYPE: DNA

<213> ORGANISM: Artificial Sequence
<220> FEATURE:
<223> OTHER INFORMATION: Synthetic

<400> SEQUENCE: 58
gtagcaactg caaccggtgt acattcagac attaaaatga ctcagagtcc atc 53

<210> SEQ ID NO 59
<211> LENGTH: 43
<212> TYPE: DNA
<213> ORGANISM: Artificial Sequence
<220> FEATURE:
<223> OTHER INFORMATION: Synthetic

<400> SEQUENCE: 59
ggtgcagcca ccgtacgttt gatttctaat tttgttccac cgc 43

<210> SEQ ID NO 60
<211> LENGTH: 49
<212> TYPE: DNA
<213> ORGANISM: Artificial Sequence
<220> FEATURE:
<223> OTHER INFORMATION: Synthetic

<400> SEQUENCE: 60
gtagcaactg caaccggtgt acattgcgaa gtcaagctag aagaaagcg 49

<210> SEQ ID NO 61
<211> LENGTH: 38
<212> TYPE: DNA
<213> ORGANISM: Artificial Sequence
<220> FEATURE:
<223> OTHER INFORMATION: Synthetic

<400> SEQUENCE: 61
gatgggccct tggtcgacgc ggcagaaacc gtcaccag 38

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
gcgtcgacca agggcccatc 20

<210> SEQ ID NO 63
<211> LENGTH: 23
<212> TYPE: DNA
<213> ORGANISM: Artificial Sequence
<220> FEATURE:
<223> OTHER INFORMATION: Synthetic

<400> SEQUENCE: 63
caaccaagtc attctgagaa tag 23

<210> SEQ ID NO 64
<211> LENGTH: 23
<212> TYPE: DNA
<213> ORGANISM: Artificial Sequence
<220> FEATURE:
<223> OTHER INFORMATION: Synthetic

<400> SEQUENCE: 64
ctattctcag aatgacttgg ttg 23

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
gcaatgtaca ccggttgcag 20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
cgtacggtgg ctgcaccatc 20

<210> SEQ ID NO 67
<211> LENGTH: 23
<212> TYPE: DNA
<213> ORGANISM: Artificial Sequence
<220> FEATURE:
<223> OTHER INFORMATION: Synthetic

<400> SEQUENCE: 67
tgaatgtaca ccggttgcag ttg 23

<210> SEQ ID NO 68
<211> LENGTH: 4
<212> TYPE: PRT
<213> ORGANISM: Artificial Sequence
<220> FEATURE:
<223> OTHER INFORMATION: Synthetic

<400> SEQUENCE: 68

Gly Gly Gly Ser
1

<210> SEQ ID NO 69
<211> LENGTH: 15
<212> TYPE: PRT
<213> ORGANISM: Artificial Sequence
<220> FEATURE:
<223> OTHER INFORMATION: Synthetic

<400> SEQUENCE: 69

Gly Gly Gly Gly Ser Gly Gly Gly Gly Ser Gly Gly Gly Gly Ser
1 5 10 15

<210> SEQ ID NO 70
<211> LENGTH: 107
<212> TYPE: PRT
<213> ORGANISM: Artificial Sequence
<220> FEATURE:
<223> OTHER INFORMATION: Synthetic

<400> SEQUENCE: 70

Asp Ile Lys Met Thr Gln Ser Pro Ser Ser Met Tyr Ala Ser Leu Gly
1 5 10 15

Glu Arg Val Thr Ile Thr Cys Lys Ala Ser Gln Asp Ile Asn Ser Tyr
20 25 30

-continued

```
Leu Ser Trp Phe Gln Gln Lys Pro Gly Lys Pro Pro Lys Thr Leu Ile
        35                  40                  45

Tyr Arg Ala Asn Arg Leu Val Pro Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Trp Cys Leu Gln Tyr Asp Glu Phe Pro Arg
                85                  90                  95

Thr Trp Gly Gly Gly Thr Lys Leu Glu Ile Lys
            100                 105


<210> SEQ ID NO 71
<211> LENGTH: 107
<212> TYPE: PRT
<213> ORGANISM: Artificial Sequence
<220> FEATURE:
<223> OTHER INFORMATION: Synthetic

<400> SEQUENCE: 71

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Arg
                85                  90                  95

Thr Phe Gly Gly Gly Thr Lys Leu Glu Ile Lys
            100                 105


<210> SEQ ID NO 72
<211> LENGTH: 107
<212> TYPE: PRT
<213> ORGANISM: Artificial Sequence
<220> FEATURE:
<223> OTHER INFORMATION: Synthetic

<400> SEQUENCE: 72

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Pro Pro Lys Thr Leu Ile
        35                  40                  45

Tyr Arg Ala Asn Arg Leu Val Ala Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Trp Cys Leu Gln Tyr Asp Glu Phe Pro Arg
                85                  90                  95

Thr Trp Gly Gly Gly Thr Lys Leu Glu Ile Lys
            100                 105


<210> SEQ ID NO 73
```

-continued

```
<211> LENGTH: 107
<212> TYPE: PRT
<213> ORGANISM: Artificial Sequence
<220> FEATURE:
<223> OTHER INFORMATION: Synthetic

<400> SEQUENCE: 73

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Pro Pro Lys Thr Leu Ile
        35                  40                  45

Tyr Arg Ala Asn Arg Leu Val Pro Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Trp Cys Leu Gln Tyr Asp Glu Phe Pro Arg
                85                  90                  95

Thr Trp Gly Gly Gly Thr Lys Leu Glu Ile Lys
            100                 105
```